(12) United States Patent
Ertle et al.

(10) Patent No.: US 11,690,848 B2
(45) Date of Patent: Jul. 4, 2023

(54) ALKOXY PYRAZOLES AS SOLUBLE GUANYLATE CYCLASE ACTIVATORS

(71) Applicant: Boehringer Ingelheim International GmbH, Ingelheim am Rhein (DE)

(72) Inventors: Judith Ertle, Ingelheim am Rhein (DE); Jochen Huber, Mittelbiberach (DE); Ruediger Streicher, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 176 days.

(21) Appl. No.: 17/258,759

(22) PCT Filed: Jul. 9, 2019

(86) PCT No.: PCT/EP2019/068448
§ 371 (c)(1),
(2) Date: Jan. 8, 2021

(87) PCT Pub. No.: WO2020/011804
PCT Pub. Date: Jan. 16, 2020

(65) Prior Publication Data
US 2021/0121473 A1  Apr. 29, 2021

Related U.S. Application Data

(60) Provisional application No. 62/696,887, filed on Jul. 12, 2018.

(51) Int. Cl.
| | |
|---|---|
| *A61K 31/5395* | (2006.01) |
| *A61K 31/44* | (2006.01) |
| *A61K 31/4725* | (2006.01) |
| *A61K 31/55* | (2006.01) |

(52) U.S. Cl.
CPC .......... *A61K 31/5395* (2013.01); *A61K 31/44* (2013.01); *A61K 31/4725* (2013.01); *A61K 31/55* (2013.01)

(58) Field of Classification Search
CPC .. A61K 31/44; A61K 31/444; A61K 31/4725; A61K 31/505; A61K 31/5395; A61K 31/55; A61K 31/553; A61P 1/16
See application file for complete search history.

(56) References Cited

U.S. PATENT DOCUMENTS

2014/0073629 A1*  3/2014  Brenneman ............... A61P 7/02
                                                                        514/211.09

FOREIGN PATENT DOCUMENTS

| WO | 2014039434 A1 | 3/2014 |
| WO | 2017200857 A1 | 11/2017 |

OTHER PUBLICATIONS

International Search Report for PCT/EP2019/068448 dated Jan. 21, 2021.

* cited by examiner

*Primary Examiner* — Savitha M Rao
(74) *Attorney, Agent, or Firm* — David L. Kershner

(57) ABSTRACT

The present invention relates to compounds of formula (I) and pharmaceutically acceptable salts thereof, wherein $R^1$, $R^2$, $R^3$, $R^4$, $R^5$, $R^6$ and $R^7$ are as defined herein, for use in the treatment of diseases or disorders that can be alleviated by sGC activation or potentiation, selected from chronic liver diseases, Non-Alcoholic Steatohepatitis (NASH), cirrhosis and portal hypertension.

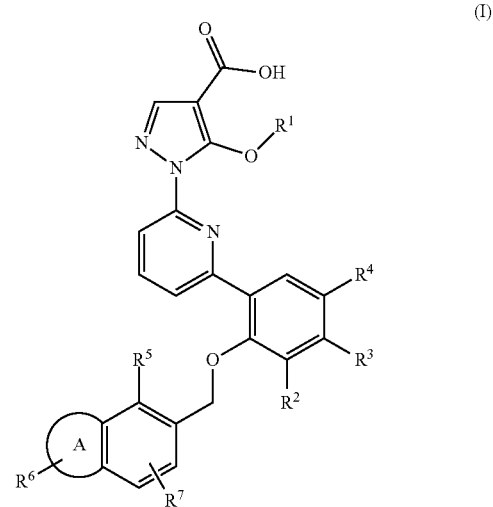

13 Claims, No Drawings

ALKOXY PYRAZOLES AS SOLUBLE GUANYLATE CYCLASE ACTIVATORS

FIELD OF THE INVENTION

This invention relates to heterocyclic compounds which are useful as activators of soluble guanylate cyclase and are thus useful for treating a variety of diseases that are mediated or sustained by decreased or diminished soluble guanylate cyclase activity, such as chronic liver diseases, Non-Alcoholic Steatohepatitis (NASH), cirrhosis, portal hypertension, and related disorders.

BACKGROUND

Soluble guanylate cyclase (sGC) is a receptor for nitric oxide (NO) which is found in the cytoplasm of many cell types. In humans, functional sGC is a heterodimer composed of either an alpha 1 or alpha 2 subunit combined with the beta 1 subunit which has a heme prosthetic group. Under non-pathophysiological conditions, NO binding to the heme of sGC activates the enzyme to catalyze the conversion of guanosine-5'-triphosphate (GTP) to cyclic guanosine monophosphate (cGMP). cGMP is a second messenger which exerts effects by modulating cGMP dependent protein kinase (PKG) isoforms, phosphodiesterases, and cGMP gated ion channels. In doing so, sGC has been demonstrated to modulate numerous pathways associated with diseases including arterial hypertension, pulmonary hypertension, atherosclerosis, heart failure, liver cirrhosis, renal fibrosis, and erectile dysfunction (O. Evgenov et al., Nature Reviews, 2006, 5, 755-768 and Y. Wang-Rosenke et al., Curr. Med. Chem., 2008, 15, 1396-1406).

Under normal conditions, the iron in sGC exists in the ferrous state which is capable of binding to NO and carbon monoxide (CO). However, under conditions of oxidative stress which can occur in various diseases, published reports indicate that the heme iron becomes oxidized to the ferric state which is incapable of being activated by NO or CO. The inability of NO to signal through sGC with an oxidized heme iron has been hypothesized to contribute to disease processes. Recently, two novel classes of compounds have been described which potentiate sGC activity in a heme dependent (sGC stimulators) and heme independent (sGC activators) manner.

The activity of sGC stimulators synergizes with NO to increase cGMP production while sGC activators are only additive with NO to augment cGMP levels (O. Evgenov et al., Nature Reviews, 2006, 5, 755-768). Both stimulators and activators of sGC have demonstrated benefit in animal models of disease. Activators of sGC provide the advantage of being able to preferentially target the diseased, non-functional form of the enzyme. sGC activators include BAY 58-2667 (cinaciguat) (J-P Stasch et al., Brit J. Pharmacol., 2002, 136, 773-783) and HMR-1766 (ataciguat) (U. Schindler et al., 2006, Mol. Pharmacol., 69, 1260-1268).

NO has an important role in maintaining normal cellular and tissue function. However, adequate signaling in the NO pathway can be disrupted at a number of steps. NO signaling can be impaired by reduced levels of nitric oxide synthase (NOS) enzymes, NOS activity, NO bioavailability, sGC levels, and sGC activity. sGC activators have the potential to bypass the functional impediment produced by all of these impairments. Since sGC activation occurs downstream of NO synthesis or NO availability, these deficiencies will not impact the activity of sGC activators. As described above, the activity of sGC in which function is disrupted by heme iron oxidation will be corrected by sGC activators. Thus, sGC activators have the potential to provide benefit in many diseases caused by defective signaling in the NO pathway.

There is evidence that sGC activation may be useful in preventing tissue fibrosis, including that of the lung, liver, skin and kidney. The processes of epithelial to mesenchyal transition (EMT) and fibroblast to myofibroblast conversion are believed to contribute to tissue fibrosis. When either cincaciguat or BAY 41-2272 was combined with sildenafil, lung fibroblast to myofibroblast conversion was inhibited (T. Dunkern et al., Eur. J. Pharm., 2007, 572, 12-22). NO is capable of inhibiting EMT of alveolar epithelial cells (S. Vyas-Read et al., Am. J. Physiol. Lung Cell Mol. Physiol., 2007, 293, 1212-1221), suggesting that sGC activation is involved in this process. NO has also been shown to inhibit glomerular TGF beta signaling (E. Dreieicher et al., J. Am. Soc. Nephrol., 2009, 20, 1963-1974) which indicates that sGC activation may be able to inhibit glomerular sclerosis. In a pig serum model and carbon tetrachloride model of liver fibrosis, an sGC activator (BAY 60-2260) was effective at inhibiting fibrosis (A. Knorr et al., Arzneimittel-Forschung, 2008, 58, 71-80) which suggests that increasing sGC activity may be used to treat nonalcoholic steatohepatitis (NASH). In the bleomycin-induced dermal fibrosis and the Tsk-1 mouse skin fibrosis models the sGC stimulator BAY 41-2272 was able to inhibit dermal thickening and myofibroblast differentiation (C. Beyer et al., Ann. Rheum. Dis., 2012, 71, 1019-1026) thus indicating that activating sGC may be useful for the treatment of systemic sclerosis.

Pharmacologically, sGC activity can be increased using sGC modulators, which comprises sGC stimulators and sGC activators. The sGC stimulators bind to the heme-containing sGC and act heme-dependently, while the sGC activators preferentially bind to oxidized sGC and act heme-independently (Sandner and Stasch, 2017). Both mechanisms of sGC stimulation lead to substantial elevation of cGMP in low endogenous NO and low-cGMP environments. Riociguat (BAY 63-2521, Adempas®) is the first sGC modulator (stimulator) that has made a successful transition from animal experiments to patients for the treatment of pulmonary hypertension. Because cGMP elevation has been associated with anti-fibrotic, anti-proliferative, and anti-inflammatory effects, sGC modulators may possess treatment potential beyond vasorelaxation in fibrotic disorders (Sandner and Stasch, 2017). Two experimental studies investigated the effects of the sGC activator BAY 60-2770 in experimental cirrhosis: Knorr et. al. demonstrated first, that BAY 60-2770 exhibits anti-fibrotic effects in rat models of CCl4-fibrosis and pig-serum induced liver injury (Knorr et al., 2008). Xie et al. confirmed these findings in a thioacetamide rat model and also observed an amelioration of sinusoidal architecture after BAY 60-2770 treatment (Xie et al., 2012). In the bile duct ligation (BDL) rat model of liver fibrosis, treatment with the sGC stimulator BAY 41-2272 caused a significant decrease in portal pressure and hepatic fibrosis as measured by hydroxyproline content and Sirius-Red staining (Nowatzky et al., 2011).

Portal hypertension (PHT), one of the major complications of liver cirrhosis is defined by an elevation of portal pressure above 10 mmHg, and it is responsible for a variety of complications such as esophageal varices, splenomegaly, hepatic encephalopathy, and ascites (Garcia-Tsao, 2006). In most cases, patients with portal hypertension show increased intrahepatic resistance due to cirrhosis as well as increased portal blood inflow through a hyperdynamic splanchnic system (Fiorucci et al., 2004).

Non-selective beta-blockers (which reduce hepatic inflow; Reiberger et al., 2017) and nitrates (nowadays rarely used due to systemic side effects; Villanueva et al., 2001) are the only available medical treatments for PHT. However, the ideal drug for portal hypertension should decrease portal pressure through the reduction of intrahepatic resistance, and if possible, maintain normal liver function by alleviation or prevention of hepatic fibrosis (Bosch et al., 2001).

Intrahepatic vascular resistance in cirrhosis is determined by both structural (i.e. fibrosis, vascular remodeling) and functional abnormalities (i.e. sinusoidal vaso-constriction, endothelial dysfunction; Fernandez, 2015). Endothelial dysfunction and sinusoidal vasoconstriction are driven by inflammation, oxidative stress and by an imbalance of vasodilators and vasoconstrictors. Nitric oxide (NO) represents the most important biogenic vasodilator, while in cirrhotic livers, both the production of and the response to NO are severely dysregulated (Wiest & Groszmann, 2002). The NO down-stream signaling target soluble guanylate cyclase (sGC) mediates vasodilation by catalyzing the reaction from GTP to cGMP (Zhao et al., 1999). The enzyme activity is predominantly regulated by a heme/Fe(II) group, which senses NO (Capece et al., 2015).

The above studies provide evidence for the use of sGC activators to patients with chronic liver diseases, NASH, and cirrhosis portal hypertension.

SUMMARY OF THE INVENTION

The present invention provides methods of using compounds of formula (I) which activate or potentiate sGC for treating diseases and disorders that can be alleviated by sGC activation or potentiation.

The compounds of the invention may be prepared by the methods and examples described in WO 2014/039434.

In a first embodiment, the invention relates to methods of treating a disease or disorder that can be alleviated by sGC activation or potentiation, the method comprising, administering to a patient in need thereof a pharmaceutically effective amount of a compound of formula I

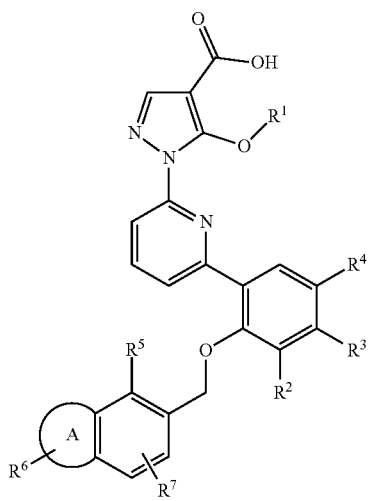

I wherein:
A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;

$R^1$ is $C_{1-4}$ alkyl optionally substituted with a methoxy group;

$R^2$ is selected from H, F, Cl, $C_{1-3}$alkyl, —CN, —OMe and —CF$_3$;

$R^3$ is selected from H and —CH$_3$;

$R^4$ is selected from H, F, —CH$_3$ and —OMe;

$R^5$ is selected from H, Cl, —CH$_3$, —CH$_2$CH$_3$, —CF$_3$, F, and —OMe;

$R^6$ is bonded to the nitrogen on A and is selected from H, $C_{1-6}$alkyl, —(CH$_2$)$_n$C$_{3-6}$cycloalkyl, —C(O)C$_{1-6}$alkyl, —(CH$_2$)$_n$ heterocyclyl, —(CH$_2$)$_n$ aryl —(CH$_2$)$_n$ heteroaryl, —SO$_2$aryl, SO$_2$C$_{1-6}$alkyl wherein said C$_{1-6}$alkyl, —(CH$_2$)$_n$ heterocyclyl, —(CH$_2$)$_n$ cycloalkyl, —(CH$_2$)$_n$ aryl and —(CH$_2$)$_n$ heteroaryl are optionally substituted with one to four groups independently selected from $C_{1-3}$alkyl, halogen, $C_{1-3}$alkoxy, —CF$_3$, —OH, oxo, —(CH$_2$)$_{1-3}$O(CH$_2$)$_{2-3}$OH, and —SO$_2$CH$_3$;

$R^7$ is absent or selected from the group consisting of —CH$_3$, —CH$_2$CH$_3$, —CF$_3$, F, and —CN;

n is 0, 1 or 2,
or a salt thereof, wherein the disease or disorder is selected from the group consisting of chronic liver diseases, NASH, cirrhosis and portal hypertension.

In a second embodiment (embodiment two), the invention relates to the method of embodiment 1 wherein the disease or disorder is NASH.

In a third embodiment (embodiment three), the invention relates to the method of any one of embodiments one or two, wherein:

A is a 5-7 membered saturated heterocyclyl group containing one nitrogen, wherein one carbon of said heterocyclyl group is optionally substituted with one or two $C_{1-3}$alkyl groups;

$R^1$ is $C_{1-3}$alkyl;

$R^2$ is selected from H, F, Cl, $C_{1-3}$alkyl, —CN, —OMe and —CF$_3$;

$R^3$ is selected from H and —CH$_3$;

$R^4$ is selected from H and F;

$R^5$ is selected from H, Cl and —CH$_3$;

$R^6$ is bonded to the nitrogen on A and is selected from H, $C_{1-6}$alkyl, —(CH$_2$)$_n$C$_{3-6}$cycloalkyl, —C(O)C$_{1-6}$alkyl, —(CH$_2$)$_n$ heterocyclyl, —(CH$_2$)$_n$ aryl and —(CH$_2$)$_n$ heteroaryl, wherein said C$_{1-6}$alkyl, —(CH$_2$)$_n$ heterocyclyl, —(CH$_2$)$_n$ cycloalkyl, —(CH$_2$)$_n$ aryl and —(CH$_2$)$_n$ heteroaryl are optionally substituted with one to four groups independently selected from C$_{1-3}$alkyl, halogen, C$_{1-3}$alkoxy, —CF$_3$, —OH and —SO$_2$CH$_3$;

$R^7$ is H;
and
n is 0, 1 or 2;
or a salt thereof.

In a fourth embodiment (embodiment four), the invention relates to the method of any one of embodiments one to three, wherein:

$R^1$ is methyl, ethyl or isopropyl; and
the group

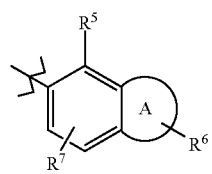

is selected from:

[Four chemical structures shown: a tetrahydroisoquinoline with R⁵ and R⁷ substituents and N—R⁶; a 4,4-dimethyl tetrahydroisoquinoline with R⁷ and N—R⁶; an isoindoline with R⁷ and N—R⁶; and a benzazepine with R⁷ and N—R⁶]

or a salt thereof.

In a fifth embodiment (embodiment five), the invention relates to the method of any one of embodiments one to four, wherein:

R² is selected from —CH₃, F, Cl, and —CF₃; and

R⁶ is selected from H, $C_{1-6}$alkyl, —(CH₂)ₙC₃₋₆cycloalkyl, —C(O)$C_{1-6}$alkyl and —(CH₂)ₙ heterocyclyl, wherein said $C_{1-6}$alkyl, —(CH₂)ₙ cycloalkyl and —(CH₂)ₙ heterocyclyl are optionally substituted with one to four groups independently selected from $C_{1-3}$alkyl, halogen, $C_{1-3}$alkoxy, —CF₃, —OH and —SO₂CH₃;

or a salt thereof.

In a sixth embodiment (embodiment six), the invention relates to the method of any one of embodiments one to five, wherein each heterocyclyl referred to in R⁶ is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl, 1-oxaspiro[4.5]decanyl and pyrrolidin-2-one; each heteroaryl referred to in R⁶ is selected from imidazolyl, isoxazolyl, pyrazinyl, pyrazolyl, pyridinyl, pyrimidinyl, thiazolyl and 4,5,6,7-tetrahydrobenzothiazolyl;

and each aryl referred to in R⁶ is phenyl;

or a salt thereof.

In a seventh embodiment (embodiment seven), the invention relates to the method of any one of embodiments one to six, wherein:

R⁶ is —(CH₂)ₙ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a salt thereof.

In an eight embodiment (embodiment eight), the invention relates to the method of any one of embodiments one to seven, wherein: R² is —CH₃;

R³ is H;

R⁴ is H or —CH₃;

R⁵ is H, or —CH₃;

R⁷ is in the position para to R and is H, —CH₃ or —CH₂CH₃;

or a salt thereof.

In a ninth embodiment (embodiment nine), the invention relates to the method of any one of embodiments one to eight, wherein:

the group

[Two chemical structures: a benzene ring with R⁵, R⁷ and fused ring A with R⁶; and a tetrahydroisoquinoline with R⁵, R⁷ and N—R⁶]   is or a salt thereof.

In a tenth embodiment (embodiment ten), the invention relates to the method of any one of embodiments one to nine, wherein:

R³ is H; and

R⁴ is H;

or a salt thereof.

DETAILED DESCRIPTION OF THE INVENTION

As discussed above, the invention relates to methods of using compounds of formula (I) treating diseases and disorders that can be alleviated by sGC activation or potentiation ("methods of the invention" or "invention").

In another embodiment, the invention relates to the method of embodiment (I) described above, wherein the compound of formula (I) is selected from any one of the compounds in Table 1, and the pharmaceutically acceptable salts thereof.

TABLE 1

| Cpd No. | Structure |
|---|---|
| 1 | [Chemical structure of compound 1: a pyrazole carboxylic acid fused system connected to a pyridine, phenyl ether, tetrahydroisoquinoline bearing a tetrahydropyran substituent] |

TABLE 1-continued

| Cpd No. | Structure |
|---|---|
| 2 | *(chemical structure)* |
| 3 | *(chemical structure)* |
| 4 | *(chemical structure)* |
| 5 | *(chemical structure)* |
| 6 | *(chemical structure)* |
| 7 | *(chemical structure)* |

TABLE 1-continued
| Cpd No. | Structure |
|---|---|
| 8 | 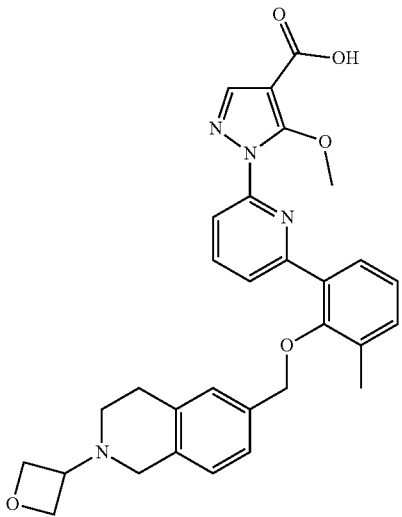 [SMILES: COc1c(C(=O)O)cnn1-c1cccc(-c2cccc(C)c2OCc2ccc3c(c2)CCN(C2COC2)C3)n1] |
| 9 | 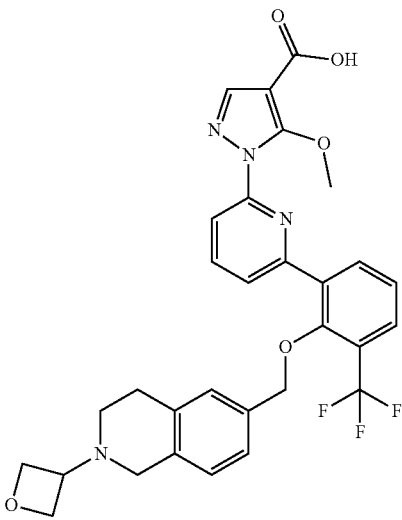 [SMILES: COc1c(C(=O)O)cnn1-c1cccc(-c2cccc(C(F)(F)F)c2OCc2ccc3c(c2)CCN(C2COC2)C3)n1] |
| 10 | 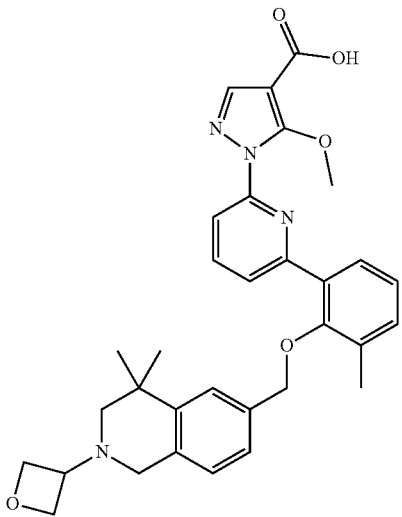 [SMILES: COc1c(C(=O)O)cnn1-c1cccc(-c2cccc(C)c2OCc2ccc3c(c2)C(C)(C)CN(C2COC2)C3)n1] |
TABLE 1-continued
| Cpd No. | Structure |
|---|---|
| 11 | 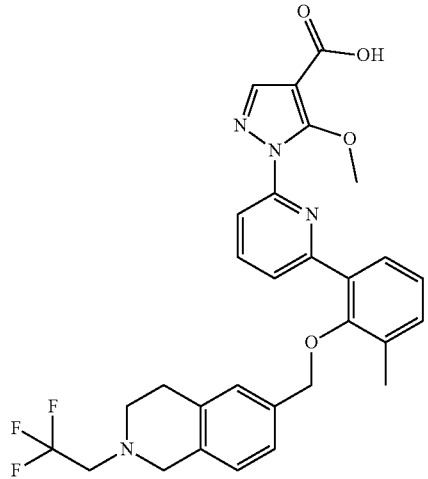 [SMILES: COc1c(C(=O)O)cnn1-c1cccc(-c2cccc(C)c2OCc2ccc3c(c2)CCN(CC(F)(F)F)C3)n1] |
| 12 | 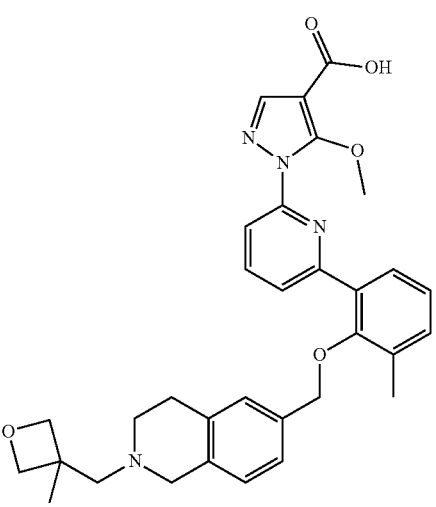 [SMILES: COc1c(C(=O)O)cnn1-c1cccc(-c2cccc(C)c2OCc2ccc3c(c2)CCN(CC2(C)COC2)C3)n1] |
| 13 | 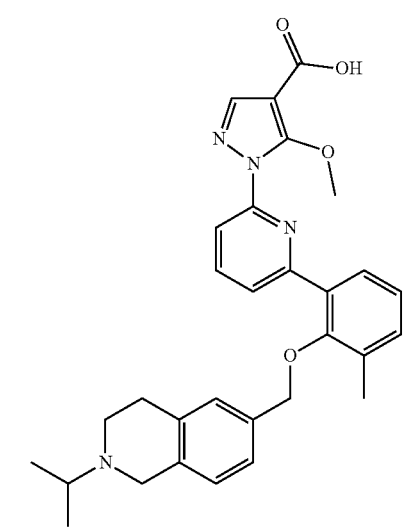 [SMILES: COc1c(C(=O)O)cnn1-c1cccc(-c2cccc(C)c2OCc2ccc3c(c2)CCN(C(C)C)C3)n1] |

TABLE 1-continued

| Cpd No. | Structure |
|---|---|
| 14 | (structure) |
| 15 | (structure) |
| 16 | (structure) |
| 17 | (structure) |
| 18 | (structure) |
| 19 | (structure) |

TABLE 1-continued
| Cpd No. | Structure |
|---|---|
| 20 | 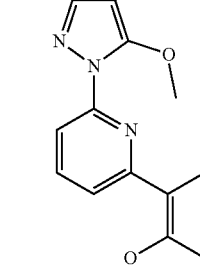 |
| 21 | 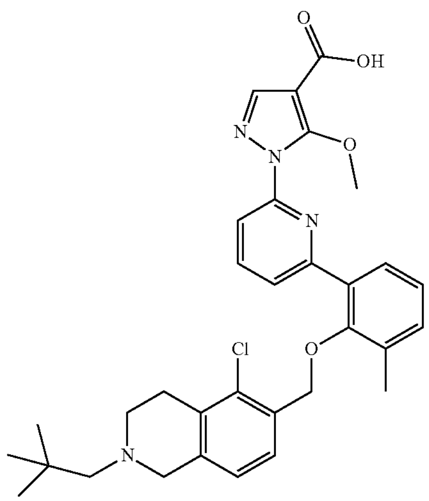 [SMILES: COc1c(C(=O)O)cnn1-c1cccc(-c2cccc(C)c2OCc2ccc3c(c2Cl)CCN(CC(C)(C)C)C3)n1] |
| 22 | 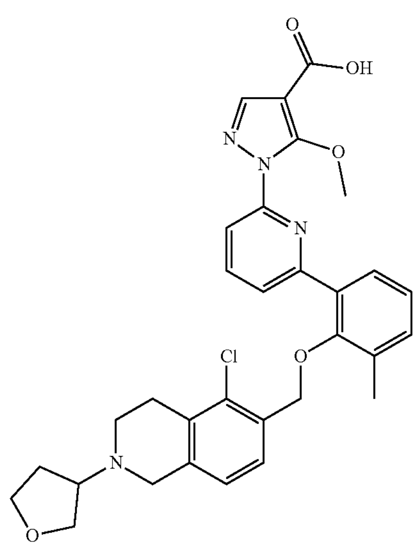 |
| 23 | 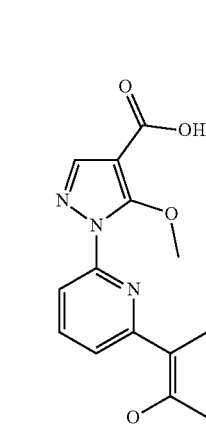 |
| 24 | |
| 25 | |

TABLE 1-continued
| Cpd No. | Structure |
|---|---|
| 26 | 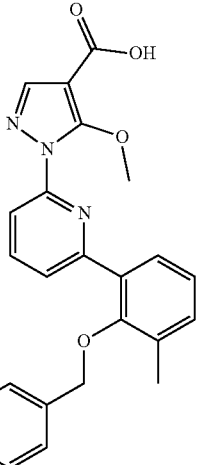 |
| 27 | 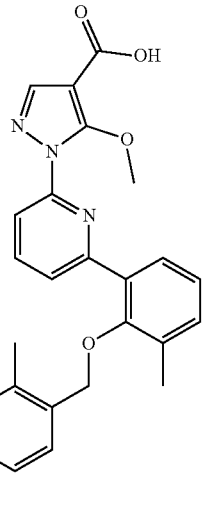 |
| 28 | 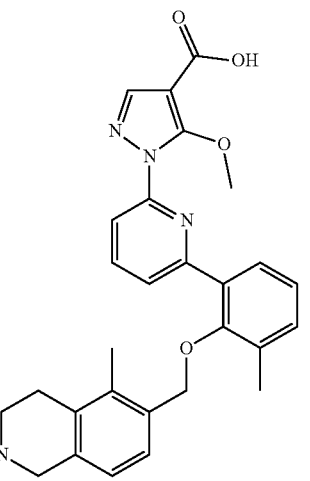 |
| 29 | 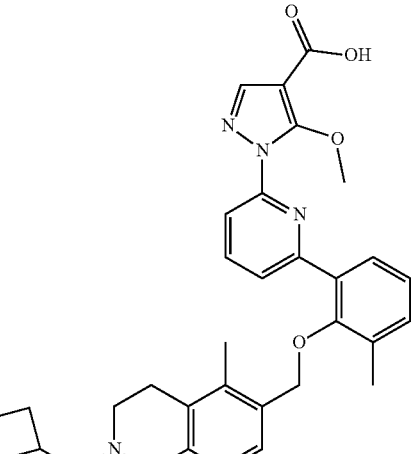 |
| 30 | 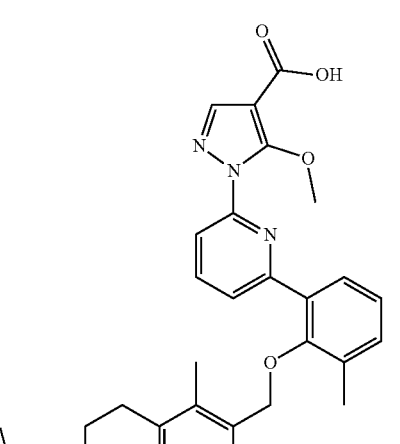 |
| 31 | 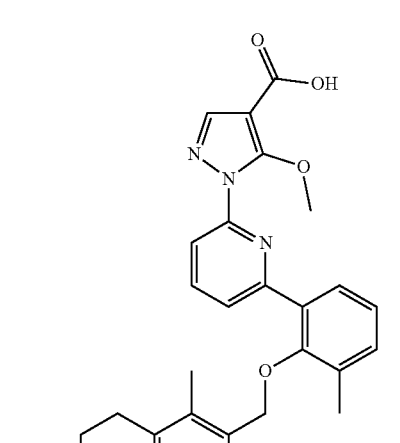 |

TABLE 1-continued
| Cpd No. | Structure |
|---|---|
| 32 | 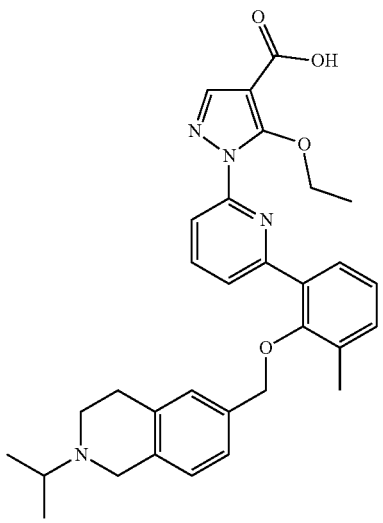 [SMILES: CCOc1c(C(=O)O)cnn1-c1cccc(-c2cccc(C)c2OCc2ccc3c(c2)CCN(C(C)C)C3)n1] |
| 33 | 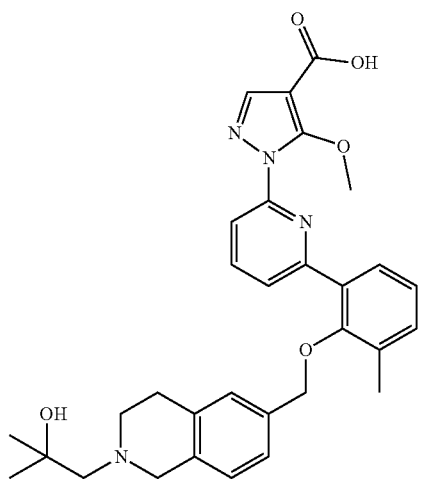 [SMILES: COc1c(C(=O)O)cnn1-c1cccc(-c2cccc(C)c2OCc2ccc3c(c2)CCN(CC(C)(C)O)C3)n1] |
| 34 | 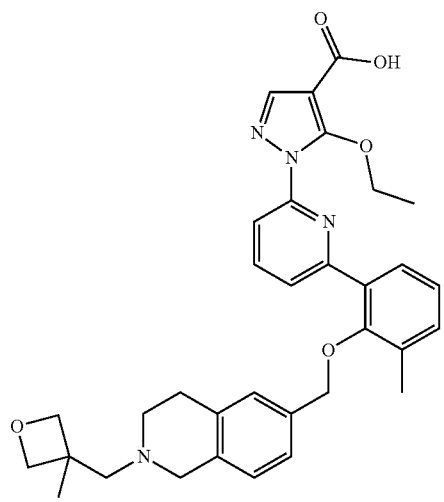 [SMILES: CCOc1c(C(=O)O)cnn1-c1cccc(-c2cccc(C)c2OCc2ccc3c(c2)CCN(CC2(C)COC2)C3)n1] |
TABLE 1-continued
| Cpd No. | Structure |
|---|---|
| 35 | 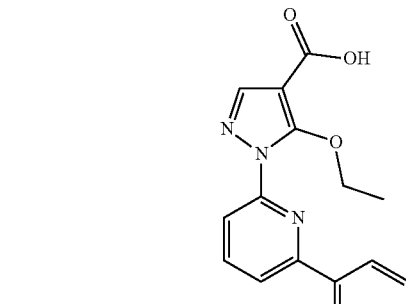 |
| 36 | 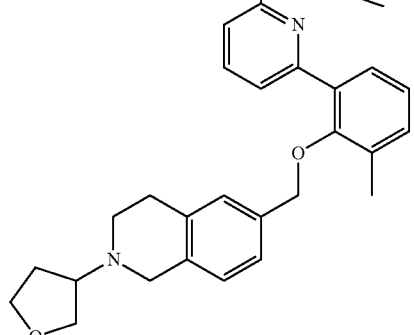 |
| 37 | 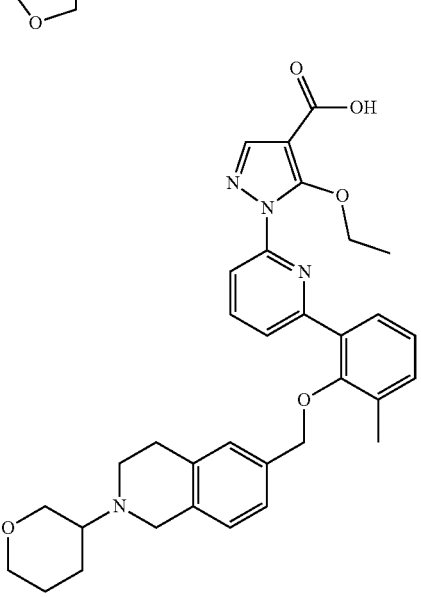 |

TABLE 1-continued
| Cpd No. | Structure |
|---|---|
| 38 | 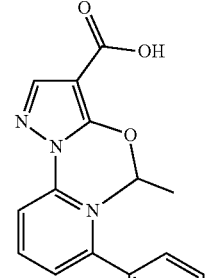 |
| 39 | |
| 40 | 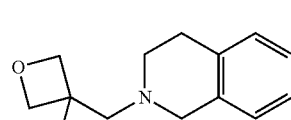 |
| 41 | 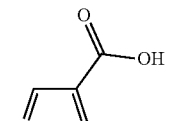 |
| 42 | 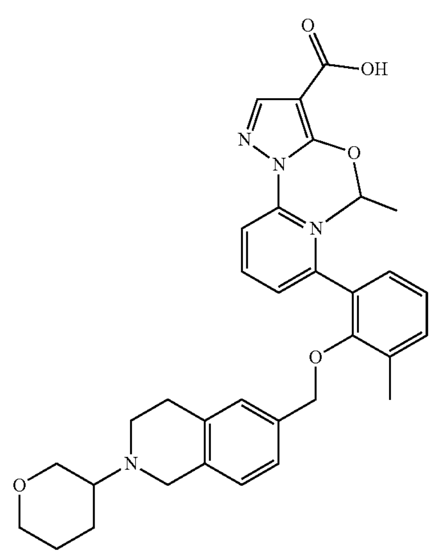 |
| | 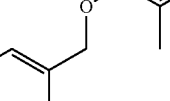 |
| |  |

TABLE 1-continued
| Cpd No. | Structure |
|---|---|
| 43 | 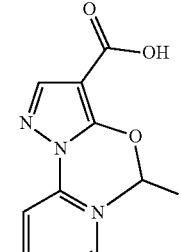 |
| 44 | 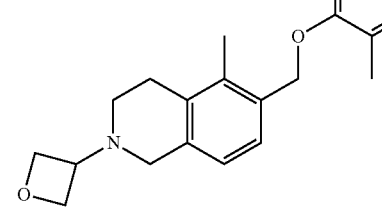 |
TABLE 1-continued
| Cpd No. | Structure |
|---|---|
| 45 | 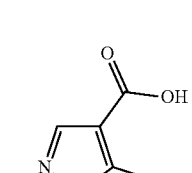 |
| 46 | 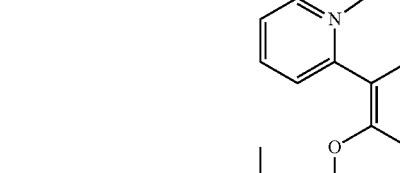 |
| 47 | 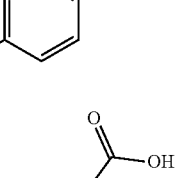 |

TABLE 1-continued

| Cpd No. | Structure |
|---|---|
| 48 | 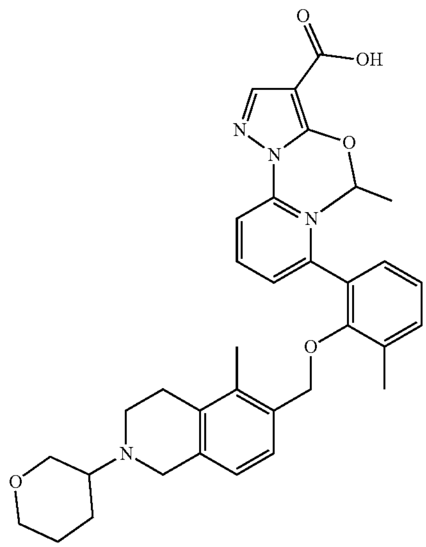 |
| 49 | 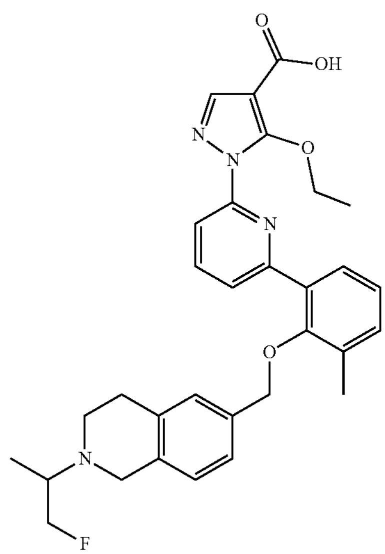 [SMILES: CCOc1c(C(=O)O)cnn1-c1cccc(-c2cccc(C)c2OCc2ccc3c(c2)CCN(C(C)CF)C3)n1] |
| 50 | 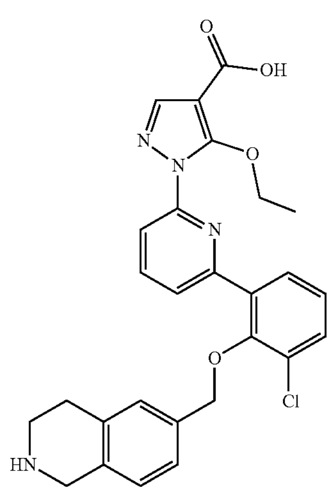 [SMILES: CCOc1c(C(=O)O)cnn1-c1cccc(-c2cccc(Cl)c2OCc2ccc3c(c2)CCNC3)n1] |
| 51 | 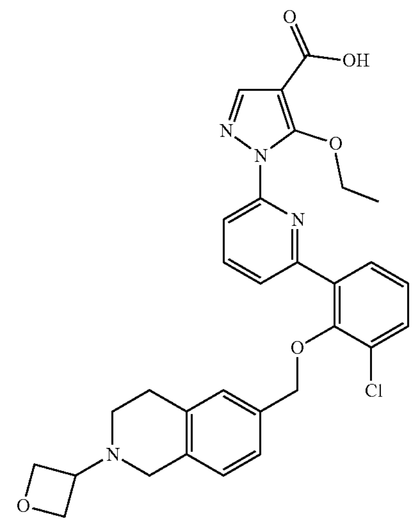 [SMILES: CCOc1c(C(=O)O)cnn1-c1cccc(-c2cccc(Cl)c2OCc2ccc3c(c2)CCN(C2COC2)C3)n1] |
| 52 | 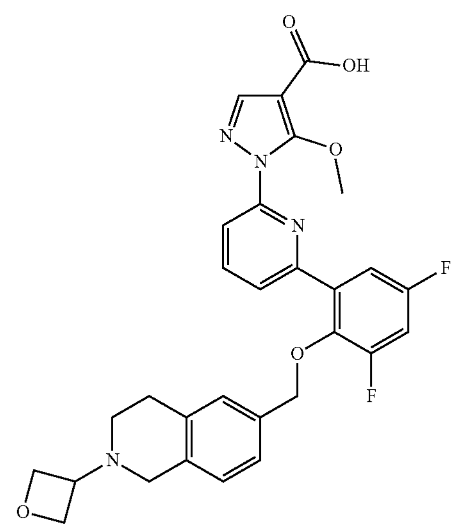 [SMILES: COc1c(C(=O)O)cnn1-c1cccc(-c2cc(F)cc(F)c2OCc2ccc3c(c2)CCN(C2COC2)C3)n1] |
| 53 | 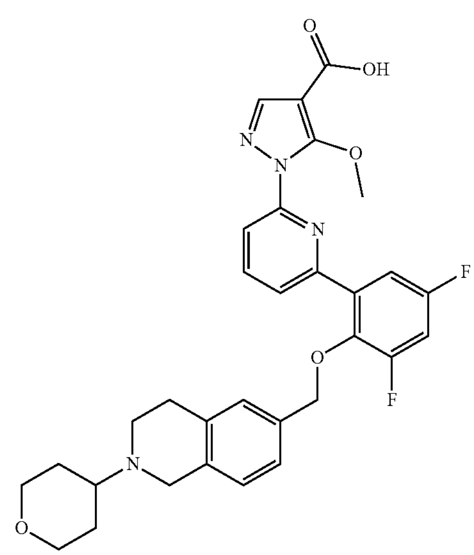 [SMILES: COc1c(C(=O)O)cnn1-c1cccc(-c2cc(F)cc(F)c2OCc2ccc3c(c2)CCN(C2CCOCC2)C3)n1] |

TABLE 1-continued
| Cpd No. | Structure |
|---|---|
| 54 | 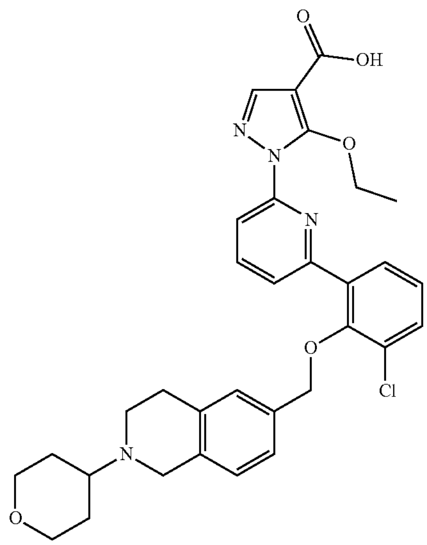 [SMILES: CCOc1c(C(=O)O)cnn1-c1cccc(-c2cccc(Cl)c2OCc2ccc3c(c2)CCN(C2CCOCC2)C3)n1] |
| 55 | 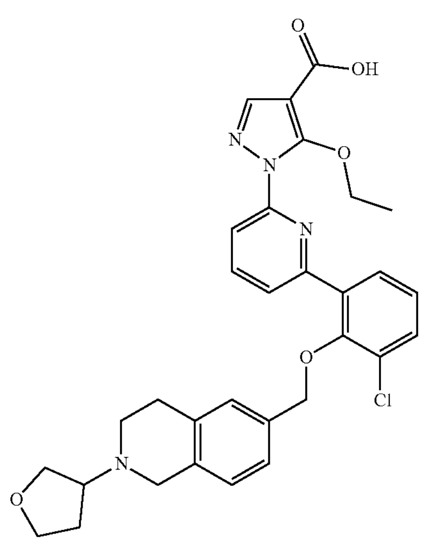 [SMILES: CCOc1c(C(=O)O)cnn1-c1cccc(-c2cccc(Cl)c2OCc2ccc3c(c2)CCN(C2CCOC2)C3)n1] |
| 56 | |
| 57 | 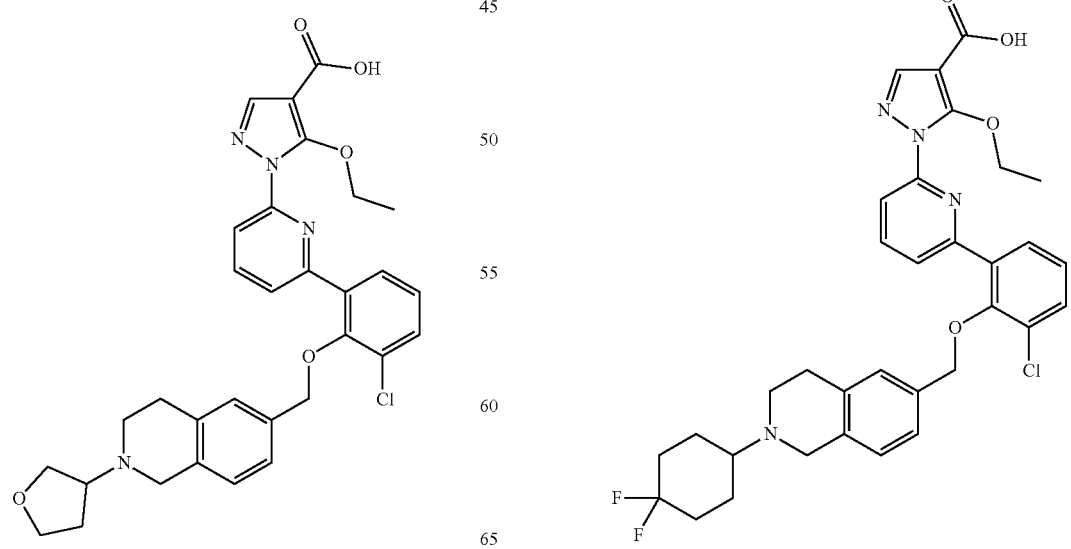 |

TABLE 1-continued
| Cpd No. | Structure |
|---|---|
| 58 | 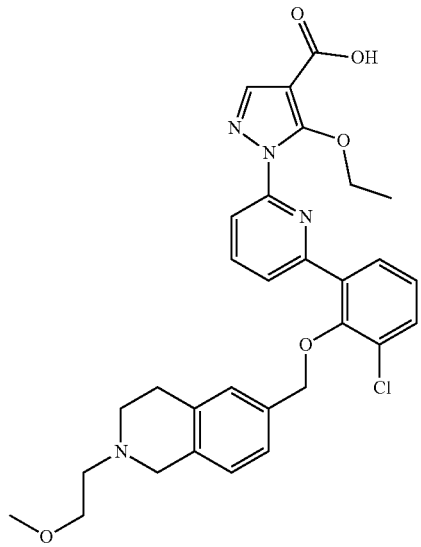 [SMILES: CCOc1c(C(=O)O)cnn1-c1cccc(-c2cccc(Cl)c2OCc2ccc3c(c2)CCN(CCOC)C3)n1] |
| 59 | 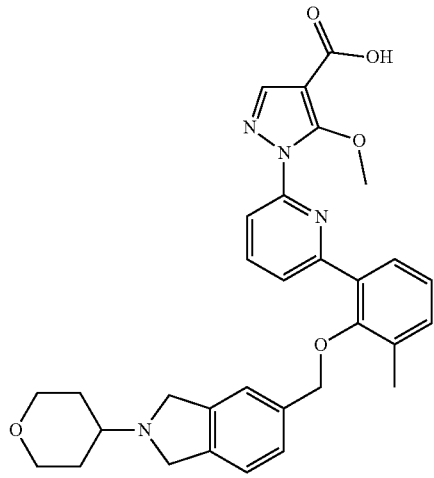 [SMILES: COc1c(C(=O)O)cnn1-c1cccc(-c2cccc(C)c2OCc2ccc3c(c2)CN(C2CCOCC2)C3)n1] |
| 60 | 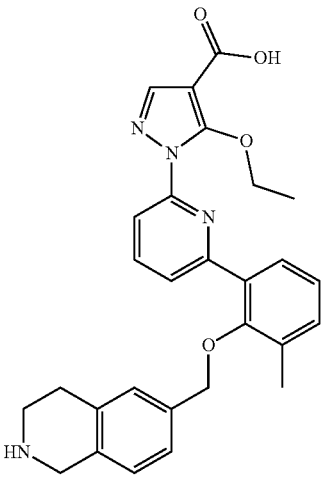 [SMILES: CCOc1c(C(=O)O)cnn1-c1cccc(-c2cccc(C)c2OCc2ccc3c(c2)CCNC3)n1] |
| 61 | 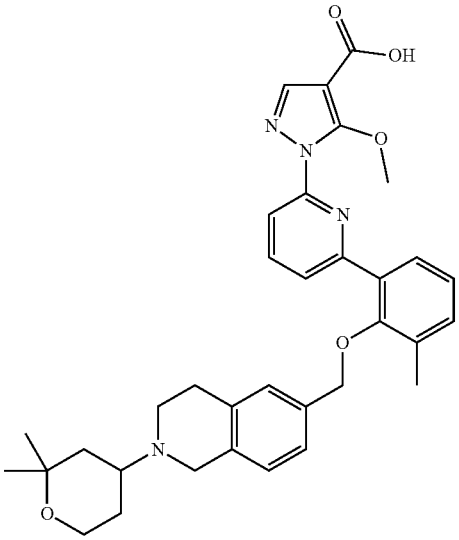 [SMILES: COc1c(C(=O)O)cnn1-c1cccc(-c2cccc(C)c2OCc2ccc3c(c2)CCN(C2CCOC(C)(C)C2)C3)n1] |
| 62 | 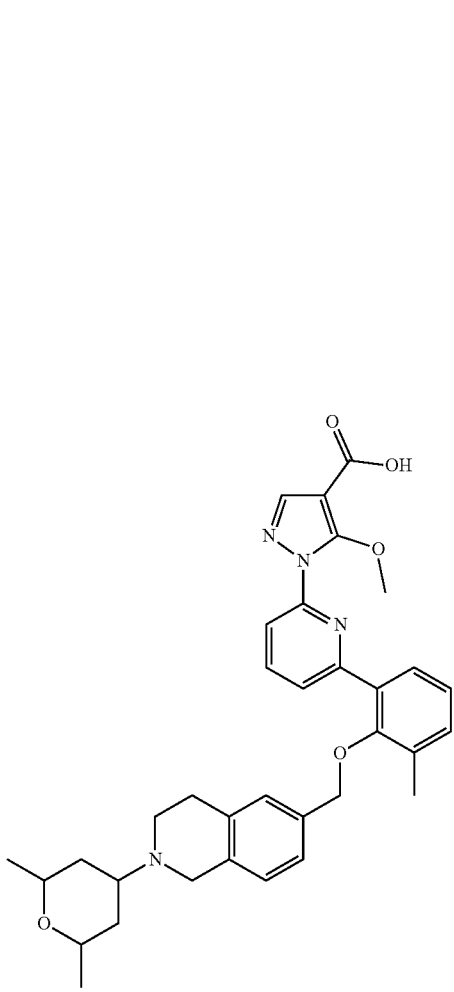 [SMILES: COc1c(C(=O)O)cnn1-c1cccc(-c2cccc(C)c2OCc2ccc3c(c2)CCN(C2CC(C)OC(C)C2)C3)n1] |

TABLE 1-continued
| Cpd No. | Structure |
|---|---|
| 63 | 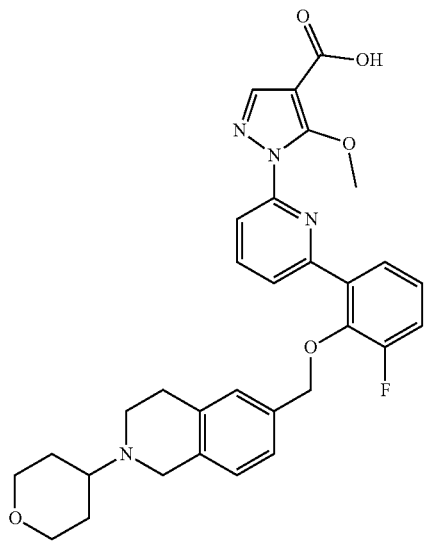 [SMILES: COc1c(C(=O)O)cnn1-c1cccc(-c2cccc(F)c2OCc2ccc3c(c2)CCN(C2CCOCC2)C3)n1] |
| 64 | 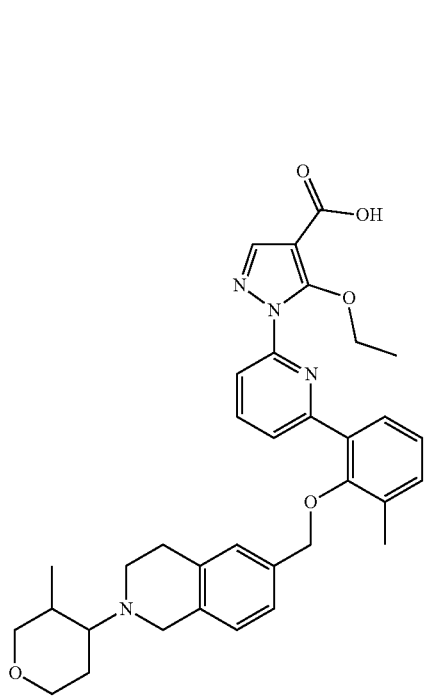 [SMILES: CCOc1c(C(=O)O)cnn1-c1cccc(-c2cccc(C)c2OCc2ccc3c(c2)CCN(C2CCOCC2C)C3)n1] |
TABLE 1-continued
| Cpd No. | Structure |
|---|---|
| 65 | 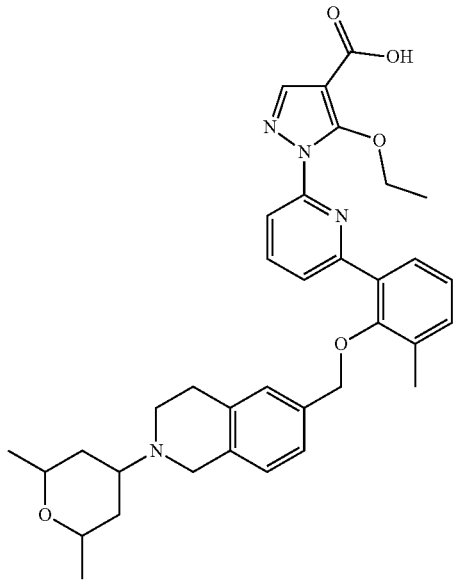 [SMILES: CCOc1c(C(=O)O)cnn1-c1cccc(-c2cccc(C)c2OCc2ccc3c(c2)CCN(C2CC(C)OC(C)C2)C3)n1] |
| 66 | 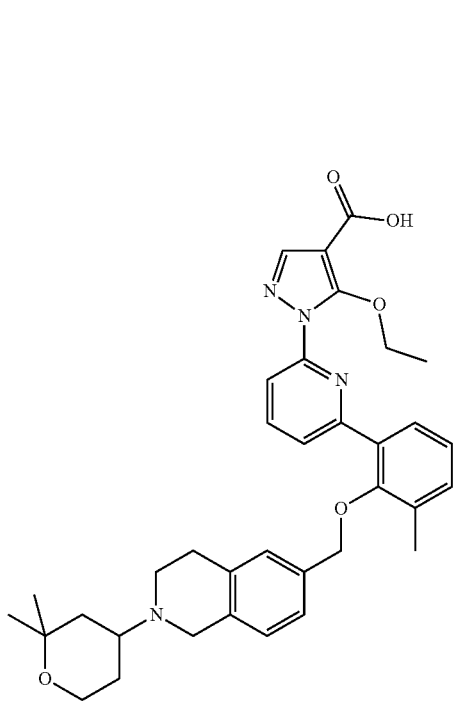 [SMILES: CCOc1c(C(=O)O)cnn1-c1cccc(-c2cccc(C)c2OCc2ccc3c(c2)CCN(C2CCOC(C)(C)C2)C3)n1] |

TABLE 1-continued

| Cpd No. | Structure |
|---|---|
| 67 | (structure) |
| 68 | (structure) |
| 69 | (structure) |
| 70 | (structure) |
| 71 | (structure) |

TABLE 1-continued

| Cpd No. | Structure |
|---|---|
| 72 | 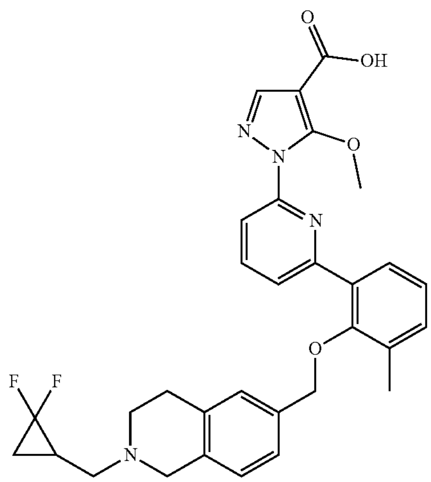 [SMILES: COc1c(C(=O)O)cnn1-c1cccc(-c2cccc(C)c2OCc2ccc3c(c2)CCN(CC2CC2(F)F)C3)n1] |
| 73 | 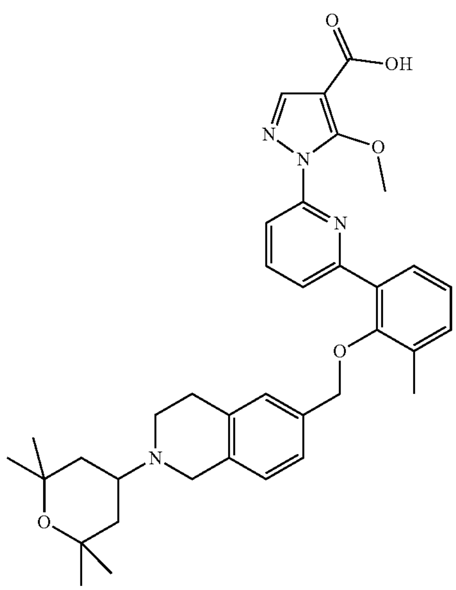 [SMILES: COc1c(C(=O)O)cnn1-c1cccc(-c2cccc(C)c2OCc2ccc3c(c2)CCN(C2CC(C)(C)OC(C)(C)C2)C3)n1] |
| 74 | 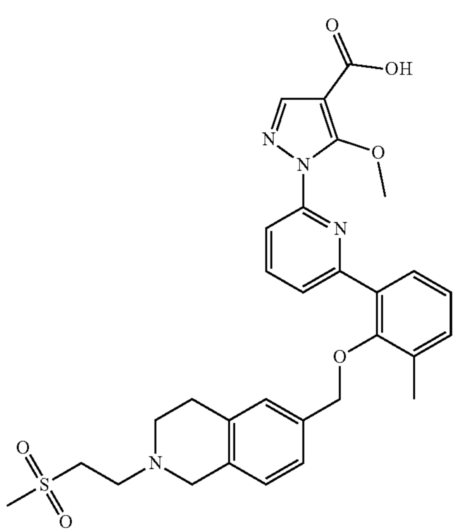 [SMILES: COc1c(C(=O)O)cnn1-c1cccc(-c2cccc(C)c2OCc2ccc3c(c2)CCN(CCS(C)(=O)=O)C3)n1] |
| 75 | |
| 76 | |

TABLE 1-continued

| Cpd No. | Structure |
|---|---|
| 77 | (structure) |
| 78 | (structure) |
| 79 | (structure) |
| 80 | (structure) |
| 81 | (structure) |

TABLE 1-continued
| Cpd No. | Structure |
|---|---|
| 82 | 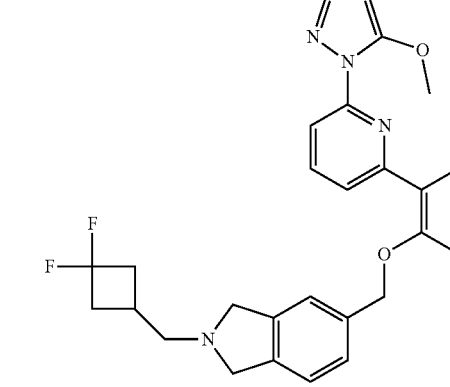 |
| 83 | 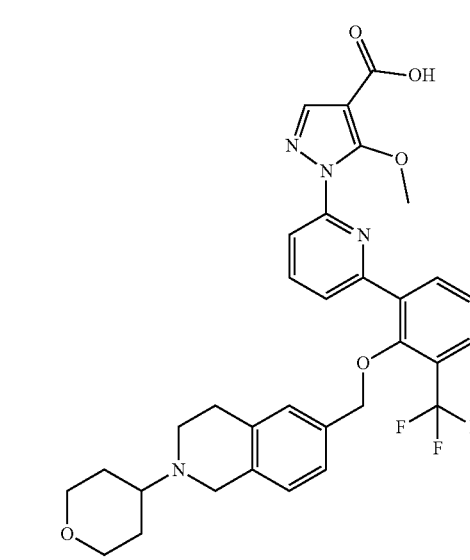 |
| 84 | 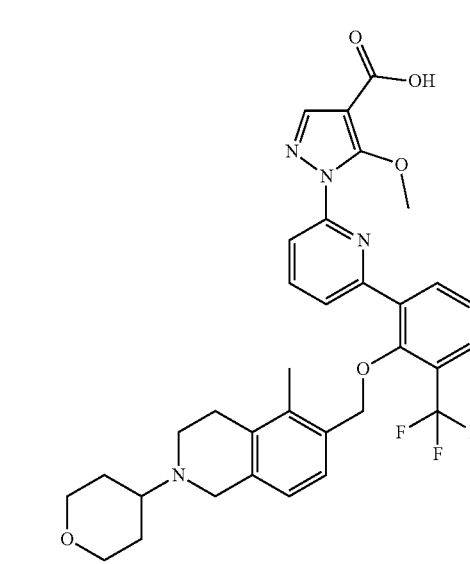 |
TABLE 1-continued
| Cpd No. | Structure |
|---|---|
| 85 | 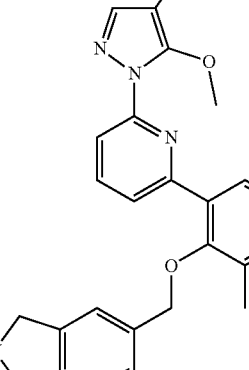 |
| 86 | 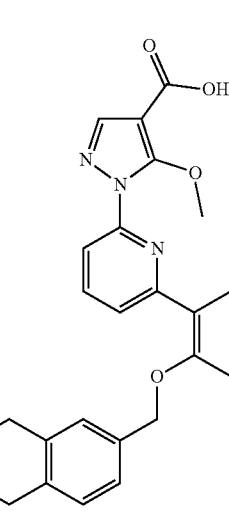 |
| 87 | 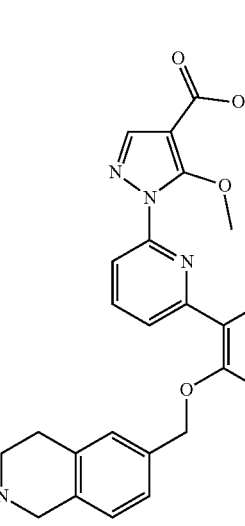 |

TABLE 1-continued
| Cpd No. | Structure |
|---|---|
| 88 | 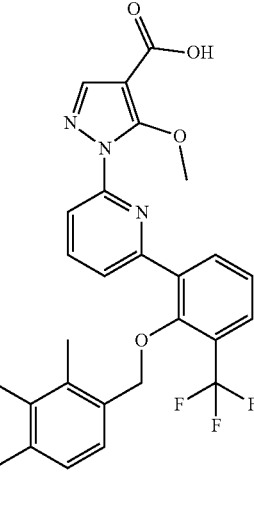 |
| 89 | 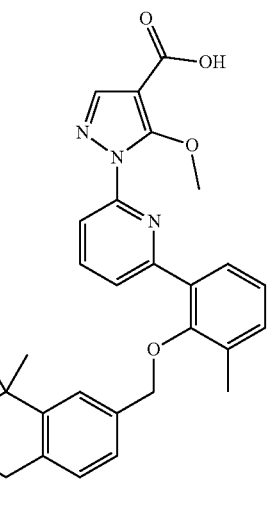 |
| 90 | 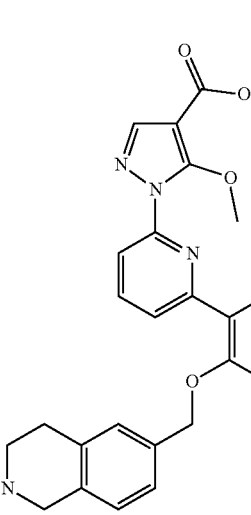 |
| 91 | 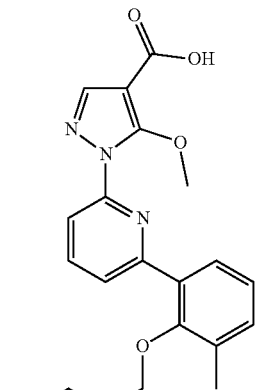 |
| 92 | 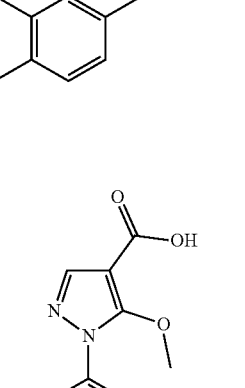 |
| 93 | 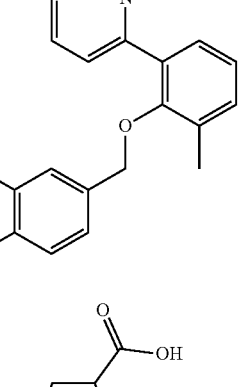 |

TABLE 1-continued

| Cpd No. | Structure |
|---|---|
| 94 | *(chemical structure)* |
| 95 | *(chemical structure)* |
| 96 | *(chemical structure)* |
| 97 | *(chemical structure)* |
| 98 | *(chemical structure)* |
| 99 | *(chemical structure)* |

TABLE 1-continued
| Cpd No. | Structure |
|---|---|
| 100 | 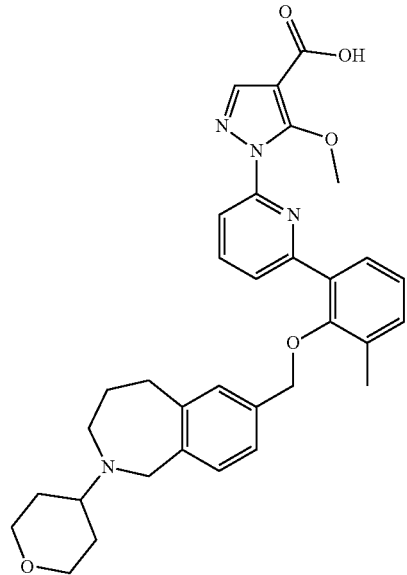 [SMILES: COc1c(C(=O)O)cnn1-c1cccc(-c2cccc(C)c2OCc2ccc3c(c2)CCCN(C2CCOCC2)C3)n1] |
| 101 | 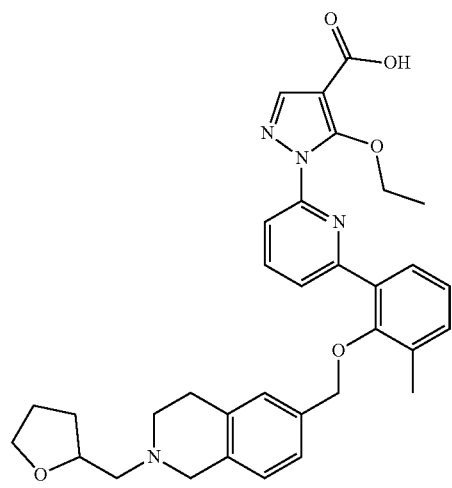 [SMILES: CCOc1c(C(=O)O)cnn1-c1cccc(-c2cccc(C)c2OCc2ccc3c(c2)CCN(CC2CCCO2)C3)n1] |
TABLE 1-continued
| Cpd No. | Structure |
|---|---|
| 102 | 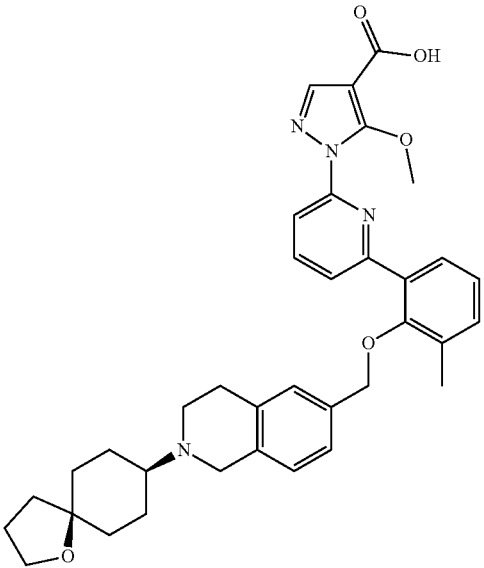 [SMILES: COc1c(C(=O)O)cnn1-c1cccc(-c2cccc(C)c2OCc2ccc3c(c2)CCN([C@H]2CC[C@]4(CCCO4)CC2)C3)n1] |
| 103 | 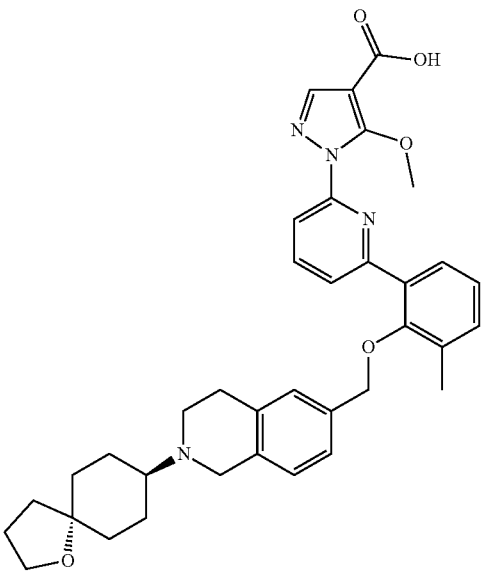 [SMILES: COc1c(C(=O)O)cnn1-c1cccc(-c2cccc(C)c2OCc2ccc3c(c2)CCN([C@H]2CC[C@@]4(CCCO4)CC2)C3)n1] |

TABLE 1-continued
| Cpd No. | Structure |
|---|---|
| 104 | 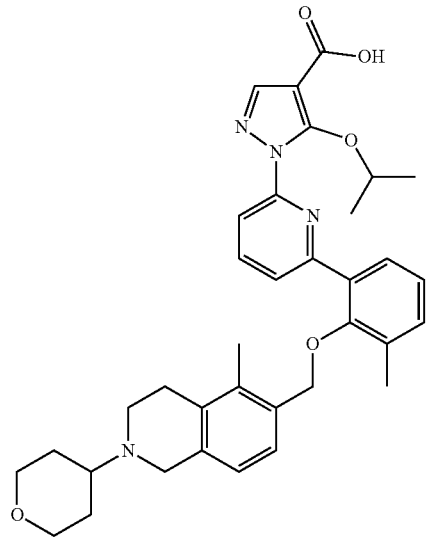 [SMILES: Cc1cccc(-c2cccc(-n3ncc(C(=O)O)c3OC(C)C)n2)c1OCc1ccc2c(c1C)CCN(C1CCOCC1)C2] |
| 105 | 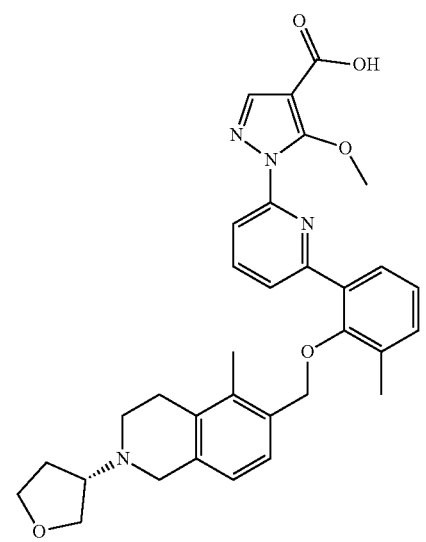 [SMILES: COc1c(C(=O)O)cnn1-c1cccc(-c2cccc(C)c2OCc2ccc3c(c2C)CCN([C@H]2CCOC2)C3)n1] |
| 106 | 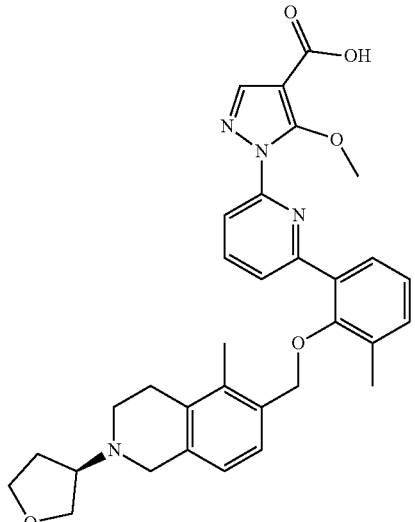 |
| 107 | 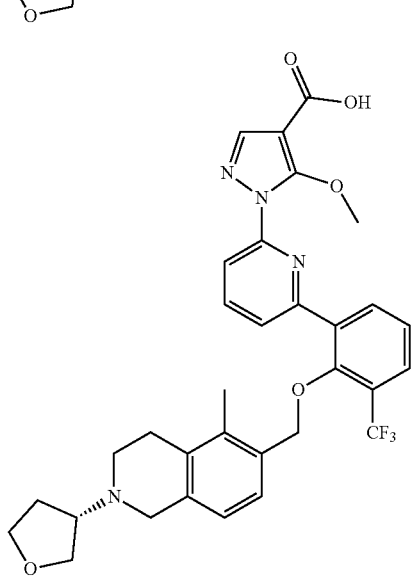 |
| 108 | 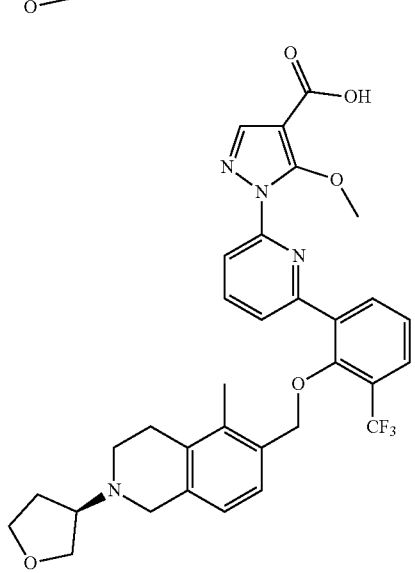 |

TABLE 1-continued
| Cpd No. | Structure |
|---|---|
| 109 | 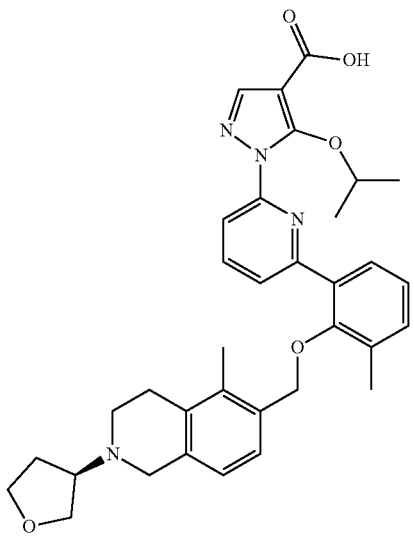 [SMILES: Cc1cccc(-c2cccc(-n3ncc(C(=O)O)c3OC(C)C)n2)c1OCc1ccc2c(c1C)CCN([C@@H]1CCOC1)C2] |
| 110 | 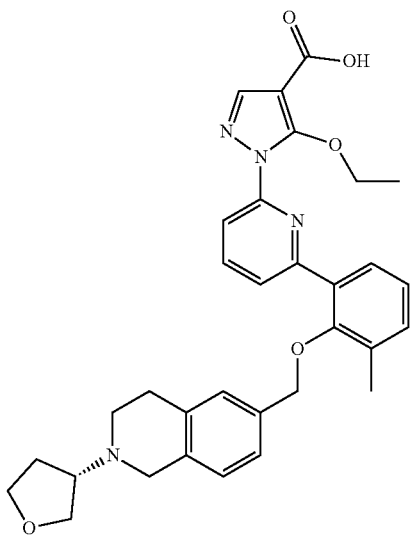 [SMILES: CCOc1c(C(=O)O)cnn1-c1cccc(-c2cccc(C)c2OCc2ccc3c(c2)CCN([C@H]2CCOC2)C3)n1] |
TABLE 1-continued
| Cpd No. | Structure |
|---|---|
| 111 | 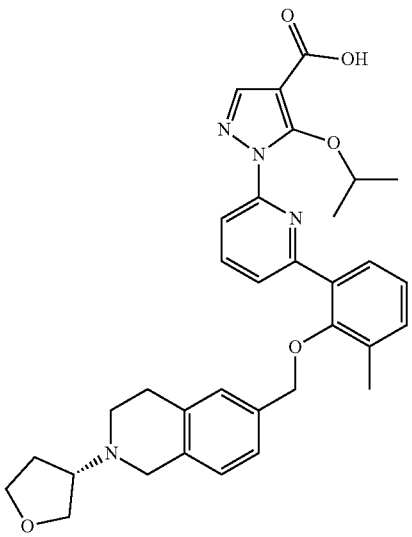 [SMILES: Cc1cccc(-c2cccc(-n3ncc(C(=O)O)c3OC(C)C)n2)c1OCc1ccc2c(c1)CCN([C@H]1CCOC1)C2] |
| 112 | 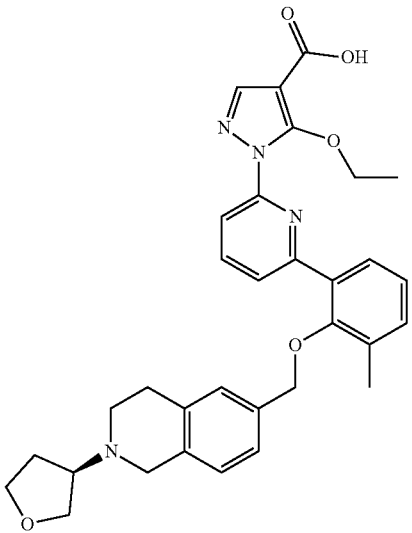 [SMILES: CCOc1c(C(=O)O)cnn1-c1cccc(-c2cccc(C)c2OCc2ccc3c(c2)CCN([C@@H]2CCOC2)C3)n1] |

TABLE 1-continued

| Cpd No. | Structure |
|---|---|
| 113 | 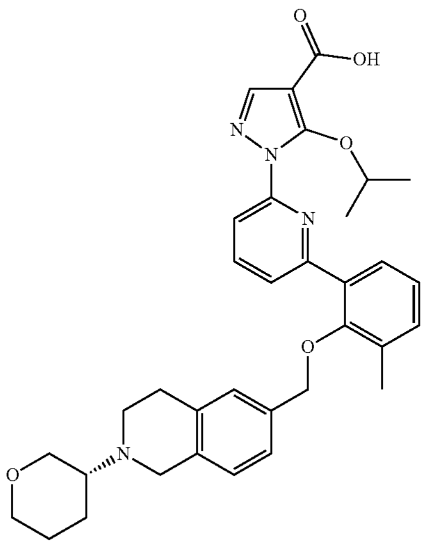 [SMILES: Cc1cccc(-c2cccc(-n3ncc(C(=O)O)c3OC(C)C)n2)c1OCc1ccc2c(c1)CCN([C@@H]1CCCOC1)C2] |
| 114 | 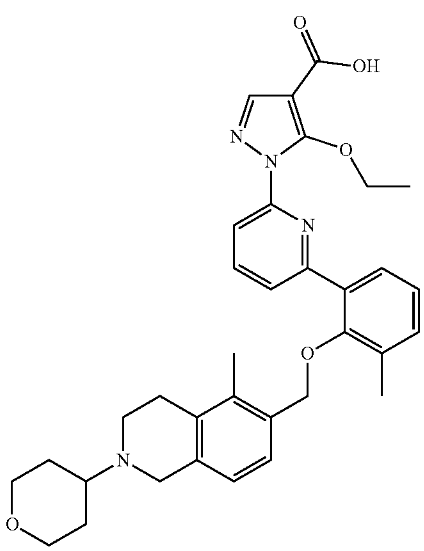 [SMILES: CCOc1c(C(=O)O)cnn1-c1cccc(-c2cccc(C)c2OCc2ccc3c(c2C)CCN(C2CCOCC2)C3)n1] |
| 115 | |
| 116 | |

TABLE 1-continued

| Cpd No. | Structure |
|---|---|
| 117 | 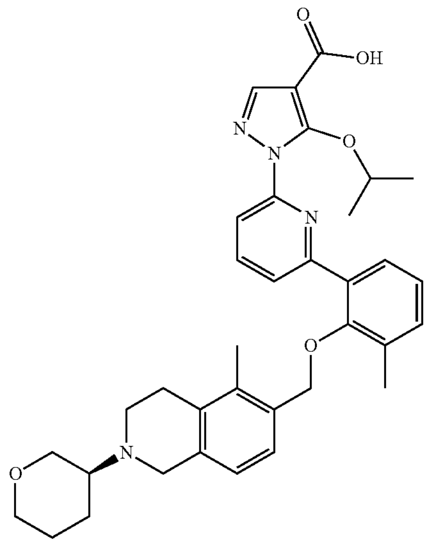 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 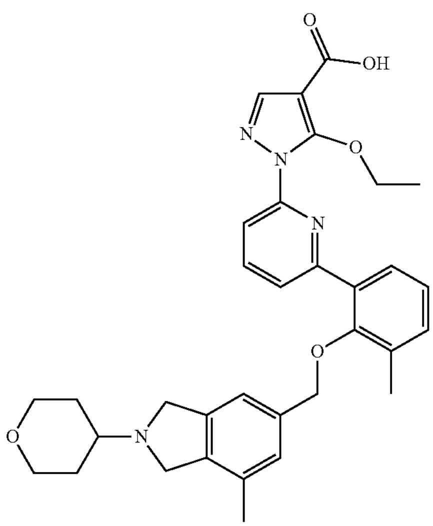 [SMILES: CCOc1c(C(=O)O)cnn1-c1cccc(-c2cccc(C)c2OCc2cc(C)c3c(c2)CN(C2CCOCC2)C3)n1] |
| 119 | 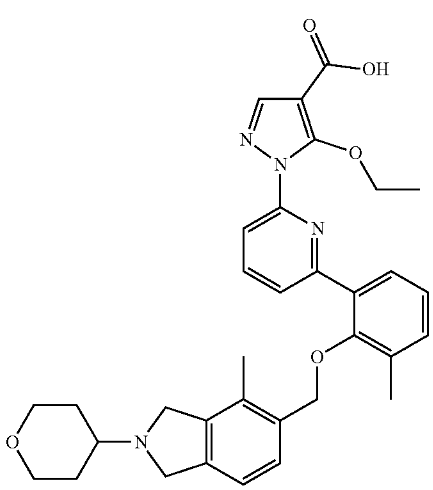 |
| 120 | |
| 121 | |

TABLE 1-continued

| Cpd No. | Structure |
|---|---|
| 122 | (structure) |
| 123 | (structure) |
| 124 | (structure) |
| 125 | (structure) |
| 126 | (structure) |
| 127 | (structure) |

TABLE 1-continued

| Cpd No. | Structure |
|---|---|
| 128 | 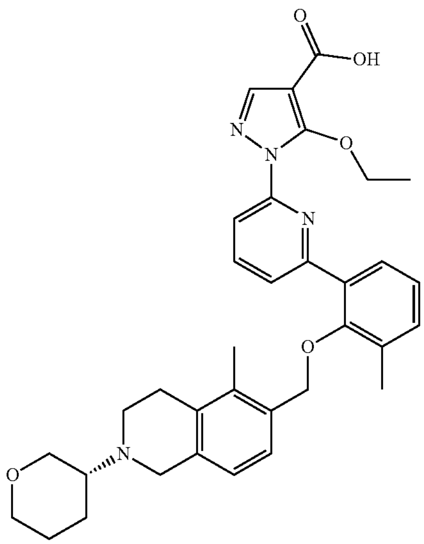 [SMILES: CCOc1c(C(=O)O)cnn1-c1cccc(-c2cccc(C)c2OCc2ccc3c(c2C)CCN([C@@H]2CCCOC2)C3)n1] |
| 129 | 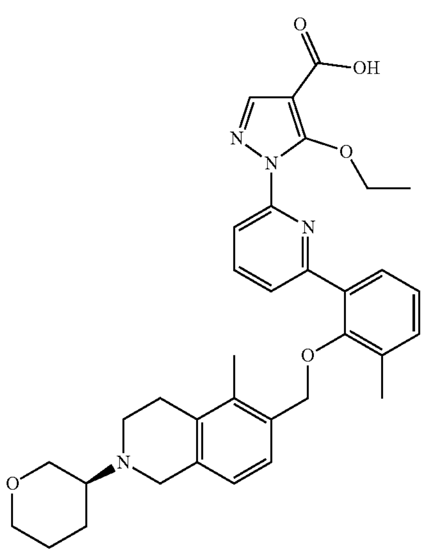 [SMILES: CCOc1c(C(=O)O)cnn1-c1cccc(-c2cccc(C)c2OCc2ccc3c(c2C)CCN([C@H]2CCCOC2)C3)n1] |
| 130 | |
| 131 | |

TABLE 1-continued

| Cpd No. | Structure |
|---|---|
| 132 | 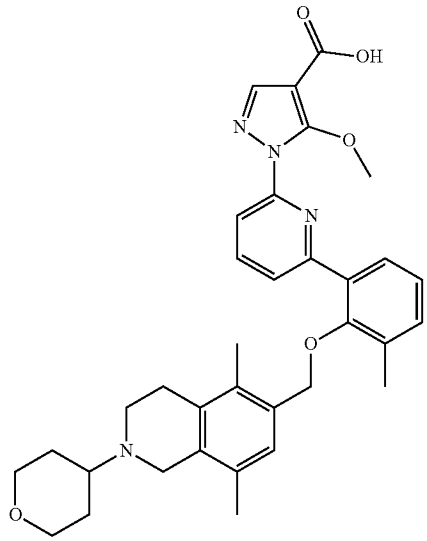 [SMILES: COc1c(C(=O)O)cnn1-c1cccc(-c2cccc(C)c2OCc2cc(C)c3c(c2C)CCN(C2CCOCC2)C3)n1] |
| 133 | 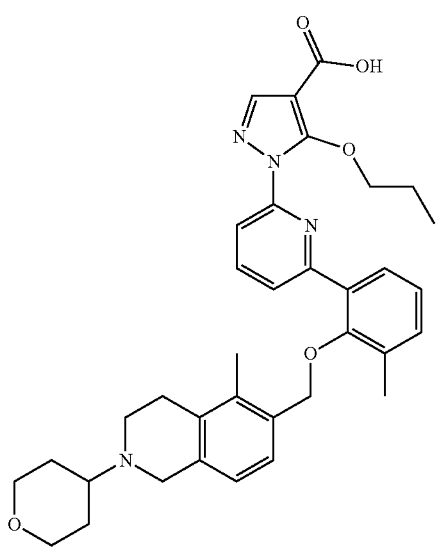 [SMILES: CCCOc1c(C(=O)O)cnn1-c1cccc(-c2cccc(C)c2OCc2ccc3c(c2C)CCN(C2CCOCC2)C3)n1] |
| 134 | |
| 135 | |

TABLE 1-continued

| Cpd No. | Structure |
|---|---|
| 136 | 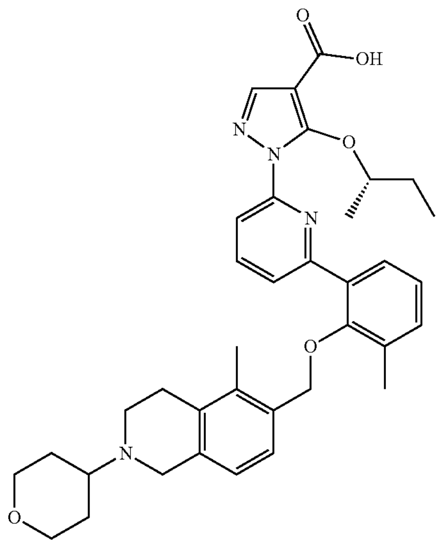 [SMILES: CC[C@H](C)Oc1c(C(=O)O)cnn1-c1cccc(-c2cccc(C)c2OCc2ccc3c(c2C)CCN(C2CCOCC2)C3)n1] |
| 137 | 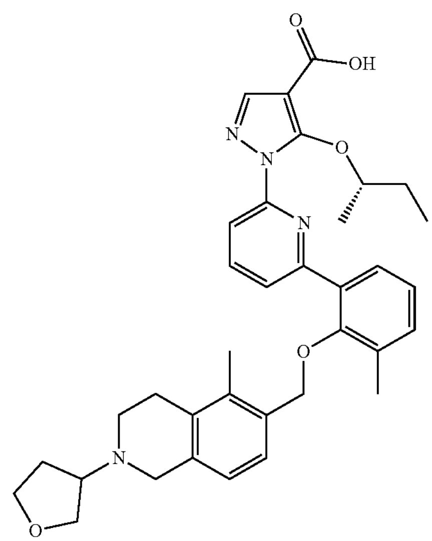 [SMILES: CC[C@H](C)Oc1c(C(=O)O)cnn1-c1cccc(-c2cccc(C)c2OCc2ccc3c(c2C)CCN(C2CCOC2)C3)n1] |
| 138 | 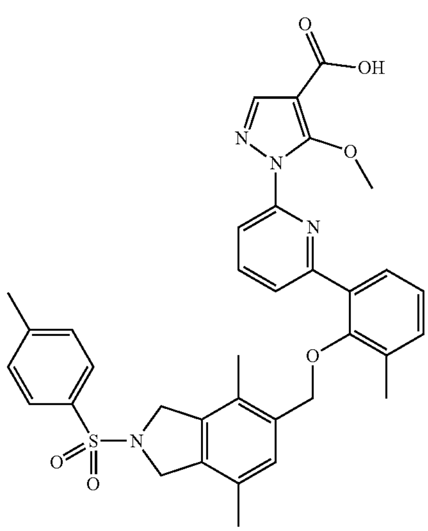 [SMILES: COc1c(C(=O)O)cnn1-c1cccc(-c2cccc(C)c2OCc2cc(C)c3c(c2C)CN(S(=O)(=O)c2ccc(C)cc2)C3)n1] |
| 139 | |
| 140 | |
| 141 | |

TABLE 1-continued

| Cpd No. | Structure |
|---|---|
| 142 | 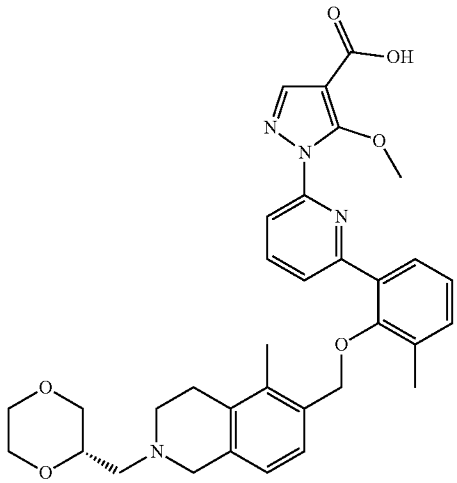 |
| 143 | 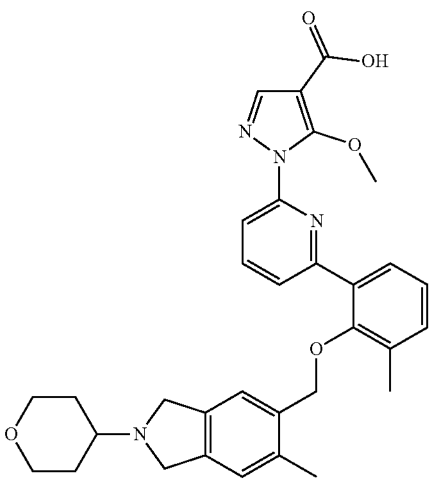 [SMILES: COc1c(C(=O)O)cnn1-c1cccc(-c2cccc(C)c2OCc2cc3c(cc2C)CN(C2CCOCC2)C3)n1] |
| 144 | 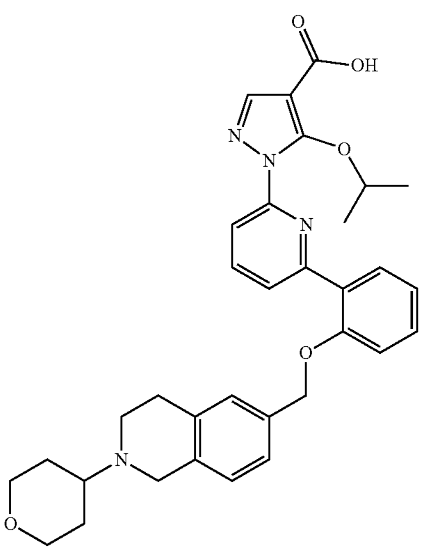 [SMILES: CC(C)Oc1c(C(=O)O)cnn1-c1cccc(-c2ccccc2OCc2ccc3c(c2)CCN(C2CCOCC2)C3)n1] |
| 145 | 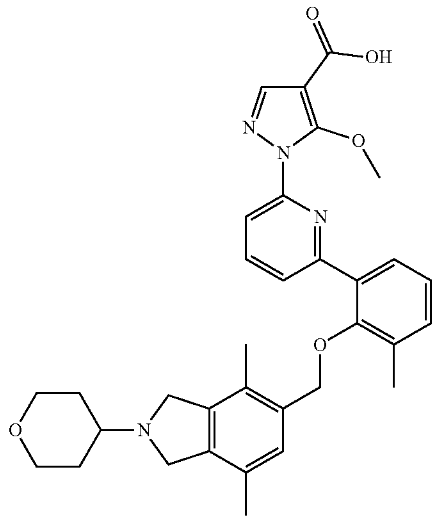 [SMILES: COc1c(C(=O)O)cnn1-c1cccc(-c2cccc(C)c2OCc2cc(C)c3c(c2C)CN(C2CCOCC2)C3)n1] |
| 146 | 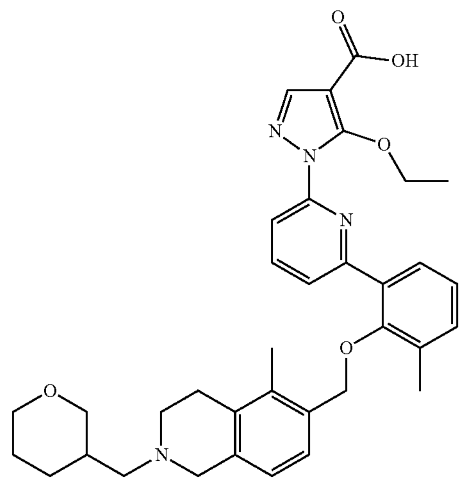 |
| 147 | 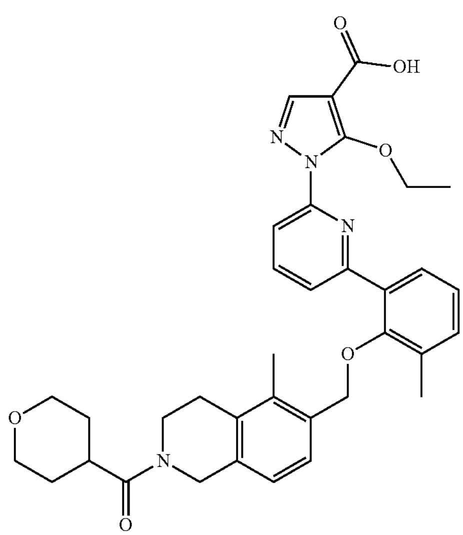 [SMILES: CCOc1c(C(=O)O)cnn1-c1cccc(-c2cccc(C)c2OCc2ccc3c(c2C)CCN(C(=O)C2CCOCC2)C3)n1] |

TABLE 1-continued
| Cpd No. | Structure |
|---|---|
| 148 | 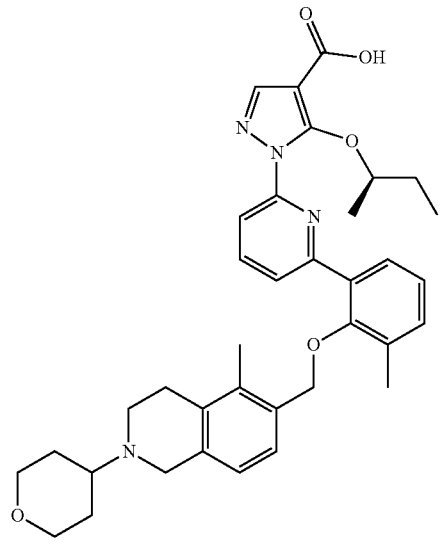 [SMILES: CC[C@@H](C)Oc1c(C(=O)O)cnn1-c1cccc(-c2cccc(C)c2OCc2ccc3c(c2C)CCN(C2CCOCC2)C3)n1] |
| 149 | 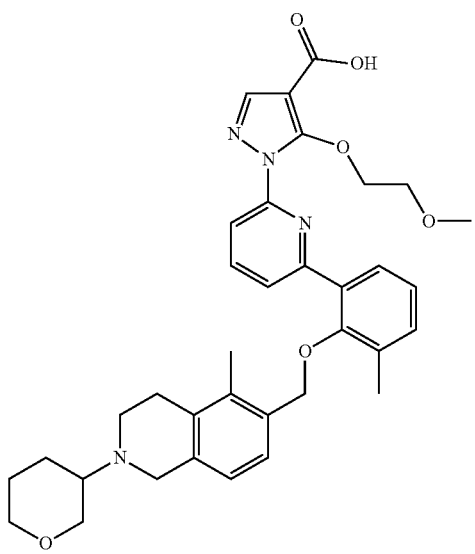 [SMILES: COCCOc1c(C(=O)O)cnn1-c1cccc(-c2cccc(C)c2OCc2ccc3c(c2C)CCN(C2CCCOC2)C3)n1] |
| 150 | 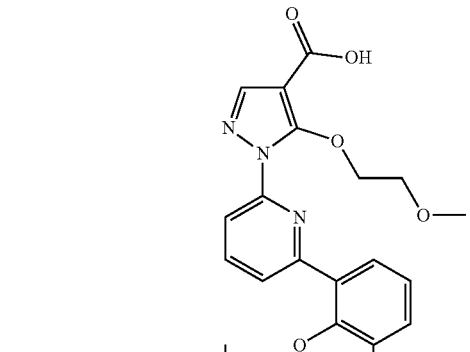 |
| 151 | 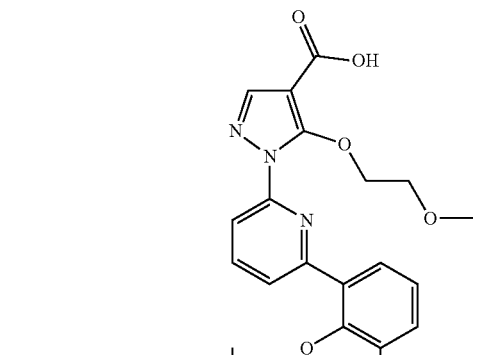 |
| 152 | 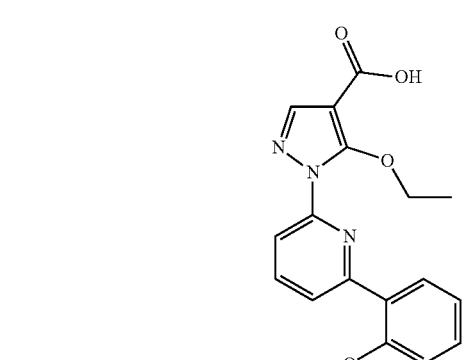 |

TABLE 1-continued

| Cpd No. | Structure |
|---|---|
| 153 | (structure) |
| 154 | (structure) |
| 155 | (structure) |
| 156 | (structure) |
| 157 | (structure) |

TABLE 1-continued

| Cpd No. | Structure |
|---|---|
| 158 | (structure) |
| 159 | (structure) |
| 160 | (structure) |
| 161 | (structure) |
| 162 | (structure) |
| 163 | (structure) |

TABLE 1-continued

| Cpd No. | Structure |
|---|---|
| 164 | (structure) |
| 165 | (structure) |
| 166 | (structure) |
| 167 | (structure) |
| 168 | (structure) |
| 169 | (structure) |

TABLE 1-continued
| Cpd No. | Structure |
|---|---|
| 170 | 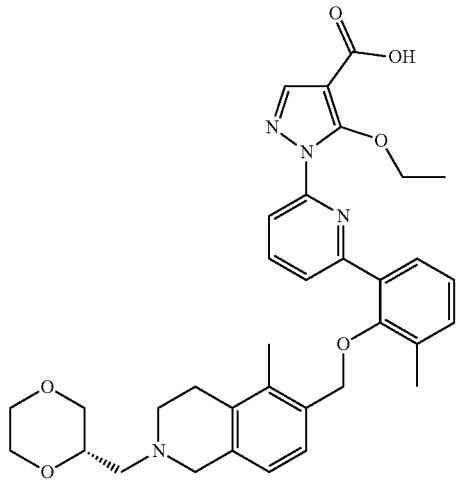 |
| 171 | 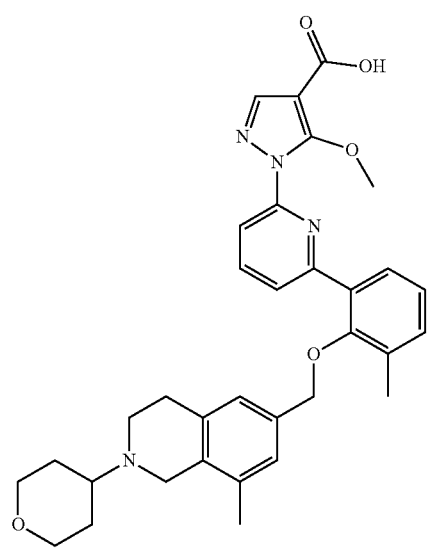 [SMILES: COc1c(C(=O)O)cnn1-c1cccc(-c2cccc(C)c2OCc2cc(C)c3c(c2)CCN(C2CCOCC2)C3)n1] |
| 172 | 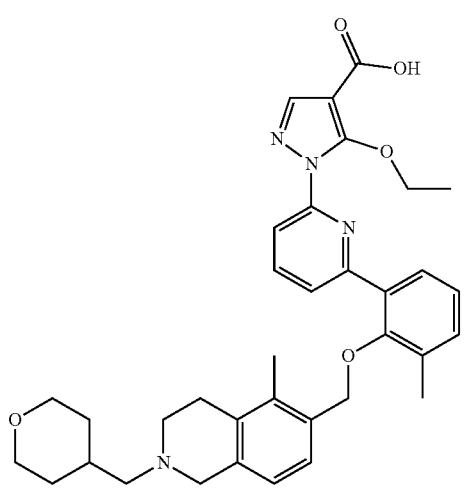 [SMILES: CCOc1c(C(=O)O)cnn1-c1cccc(-c2cccc(C)c2OCc2ccc3c(c2C)CCN(CC2CCOCC2)C3)n1] |
TABLE 1-continued
| Cpd No. | Structure |
|---|---|
| 173 | 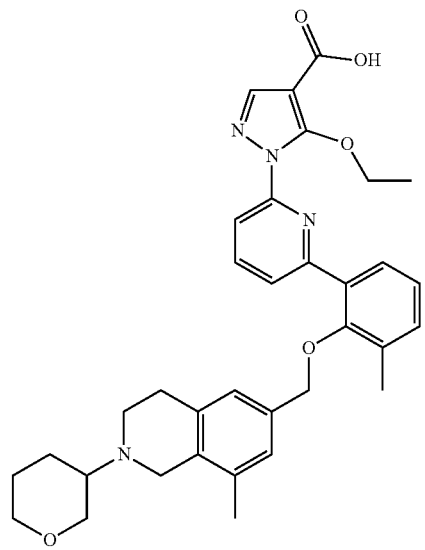 [SMILES: CCOc1c(C(=O)O)cnn1-c1cccc(-c2cccc(C)c2OCc2cc(C)c3c(c2)CCN(C2CCCOC2)C3)n1] |
| 174 | 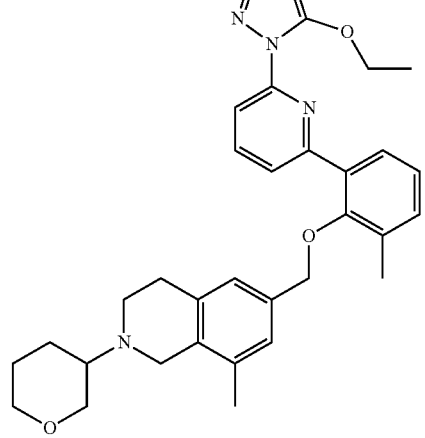 |
| 175 | 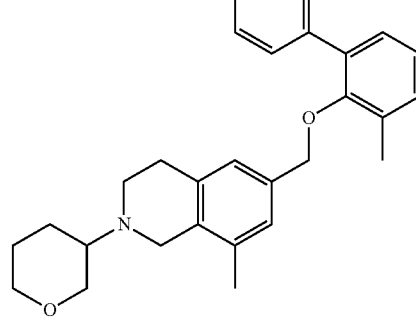 |

TABLE 1-continued

| Cpd No. | Structure |
|---|---|
| 176 | 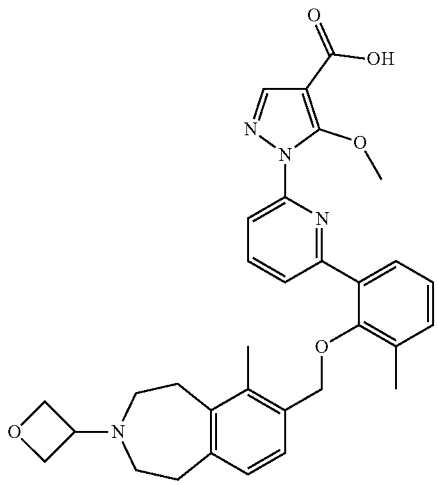 [SMILES: COc1c(C(=O)O)cnn1-c1cccc(-c2cccc(C)c2OCc2ccc3c(c2C)CCN(C2COC2)CC3)n1] |
| 177 | 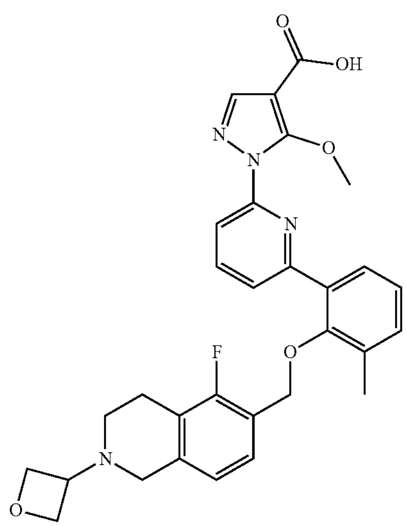 [SMILES: COc1c(C(=O)O)cnn1-c1cccc(-c2cccc(C)c2OCc2ccc3c(c2F)CCN(C2COC2)C3)n1] |
| 178 | 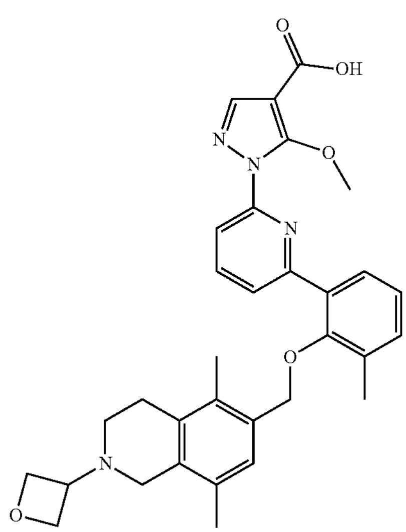 [SMILES: COc1c(C(=O)O)cnn1-c1cccc(-c2cccc(C)c2OCc2cc(C)c3c(c2C)CCN(C2COC2)C3)n1] |
| 179 | |
| 180 | |
| 181 | |

TABLE 1-continued

| Cpd No. | Structure |
|---|---|
| 182 | 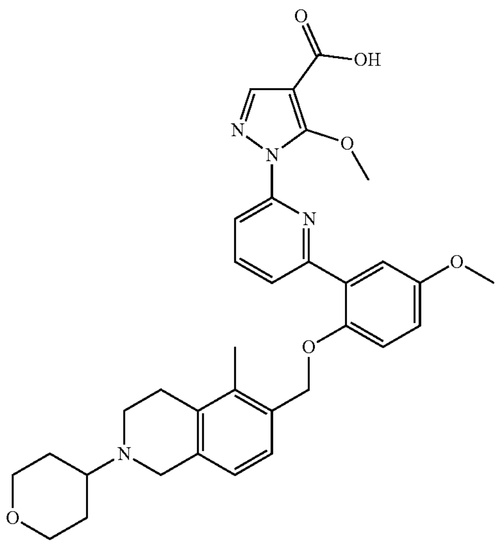 |
| 183 | 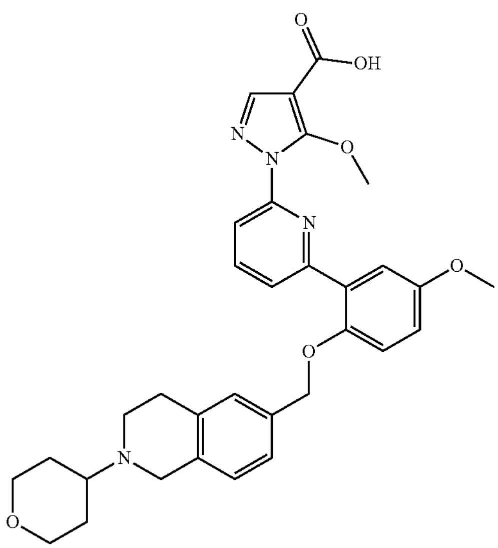 [SMILES: COc1ccc(OCc2ccc3c(c2)CCN(C2CCOCC2)C3)c(-c2cccc(-n3ncc(C(=O)O)c3OC)n2)c1] |
| 184 | 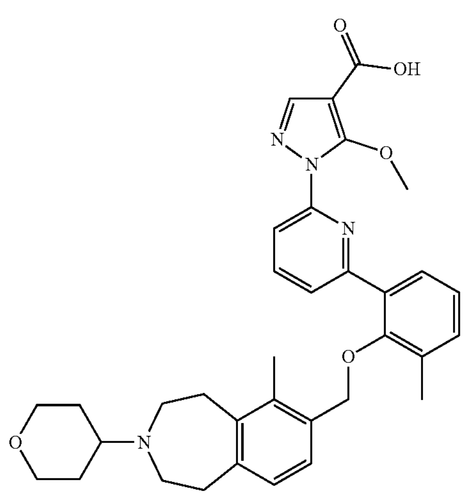 [SMILES: COc1c(C(=O)O)cnn1-c1cccc(-c2cccc(C)c2OCc2ccc3c(c2C)CCN(C2CCOCC2)CC3)n1] |
| 185 | |
| 186 | |
| 187 | |

TABLE 1-continued
| Cpd No. | Structure |
|---|---|
| 188 | 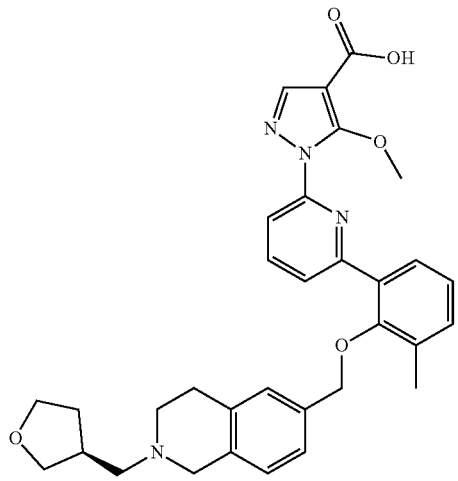 [SMILES: COc1c(C(=O)O)cnn1-c1cccc(-c2cccc(C)c2OCc2ccc3c(c2)CCN(C[C@@H]2CCOC2)C3)n1] |
| 189 | 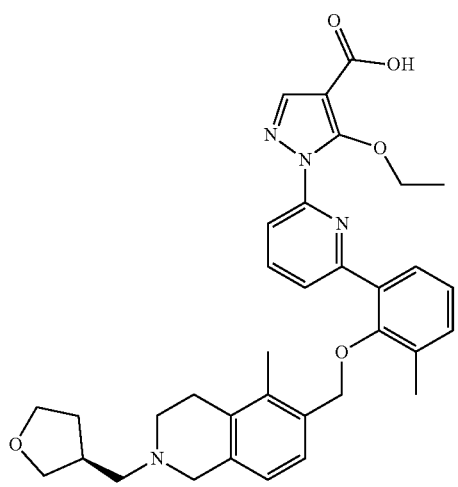 [SMILES: CCOc1c(C(=O)O)cnn1-c1cccc(-c2cccc(C)c2OCc2ccc3c(c2C)CCN(C[C@@H]2CCOC2)C3)n1] |
| 190 | 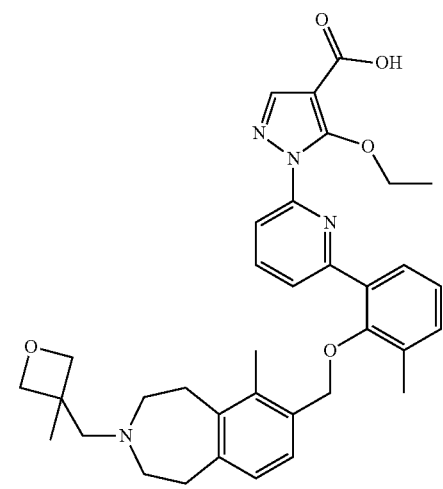 [SMILES: CCOc1c(C(=O)O)cnn1-c1cccc(-c2cccc(C)c2OCc2ccc3c(c2C)CCN(CC2(C)COC2)CC3)n1] |
TABLE 1-continued
| Cpd No. | Structure |
|---|---|
| 191 | 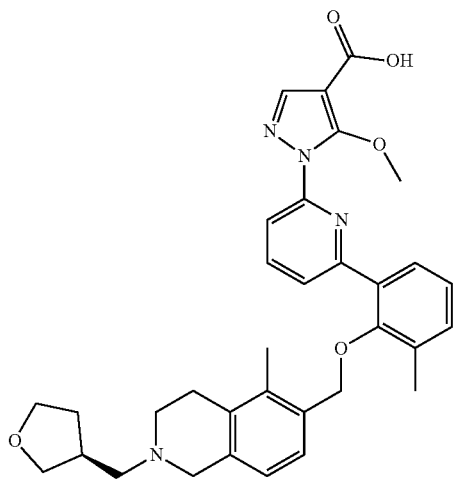 [SMILES: COc1c(C(=O)O)cnn1-c1cccc(-c2cccc(C)c2OCc2ccc3c(c2C)CCN(C[C@@H]2CCOC2)C3)n1] |
| 192 | 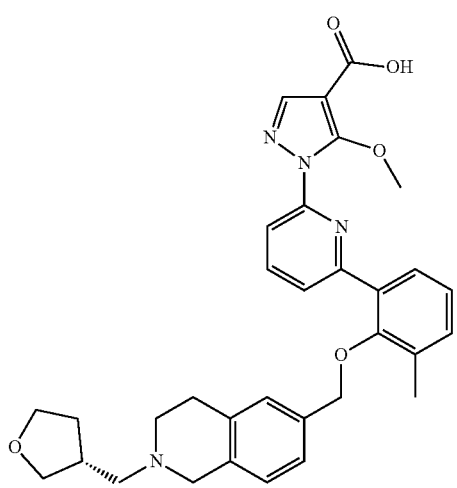 [SMILES: COc1c(C(=O)O)cnn1-c1cccc(-c2cccc(C)c2OCc2ccc3c(c2)CCN(C[C@H]2CCOC2)C3)n1] |
| 193 | 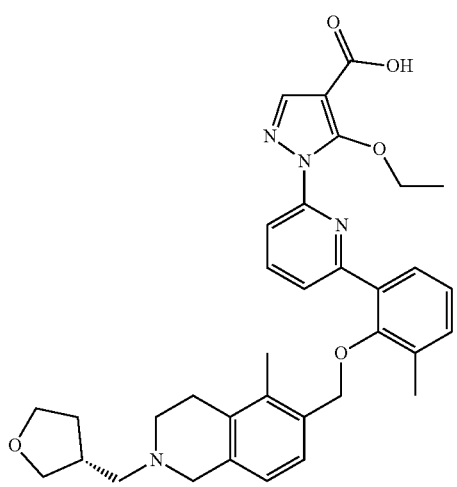 [SMILES: CCOc1c(C(=O)O)cnn1-c1cccc(-c2cccc(C)c2OCc2ccc3c(c2C)CCN(C[C@H]2CCOC2)C3)n1] |

TABLE 1-continued

| Cpd No. | Structure |
|---|---|
| 194 | 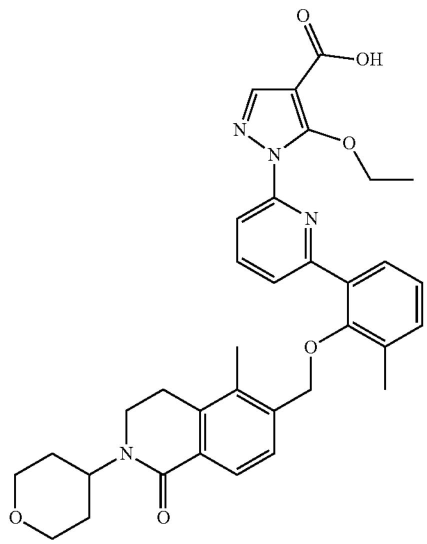 [SMILES: CCOc1c(C(=O)O)cnn1-c1cccc(-c2cccc(C)c2OCc2ccc3c(c2C)CCN(C2CCOCC2)C3=O)n1] |
| 195 | 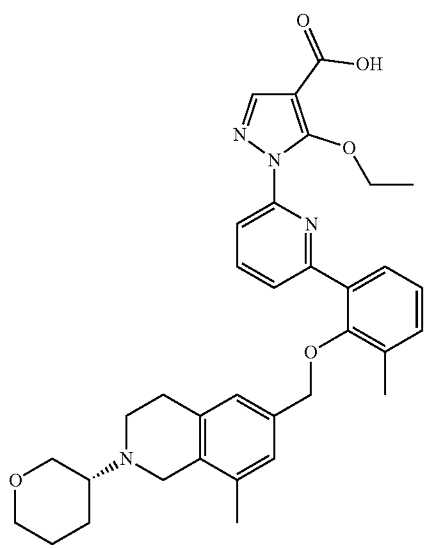 [SMILES: CCOc1c(C(=O)O)cnn1-c1cccc(-c2cccc(C)c2OCc2cc(C)c3c(c2)CCN([C@@H]2CCCOC2)C3)n1] |
| 196 | 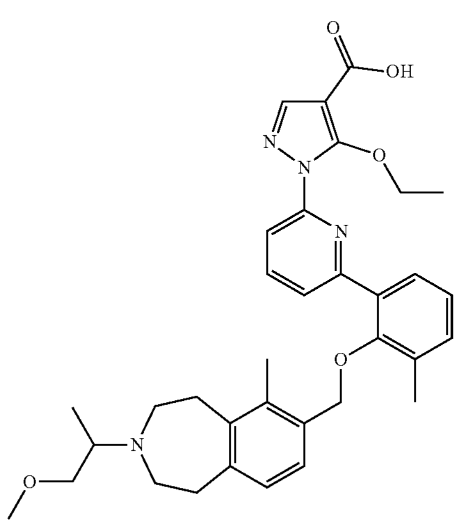 [SMILES: CCOc1c(C(=O)O)cnn1-c1cccc(-c2cccc(C)c2OCc2ccc3c(c2C)CCN(C(C)COC)CC3)n1] |
| 197 | |
| 198 | |
| 199 | |

TABLE 1-continued

| Cpd No. | Structure |
|---|---|
| 200 | 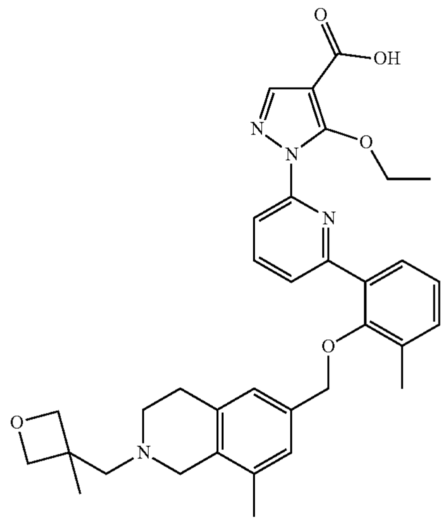 [SMILES: CCOc1c(C(=O)O)cnn1-c1cccc(-c2cccc(C)c2OCc2cc(C)c3c(c2)CCN(CC2(C)COC2)C3)n1] |
| 201 | 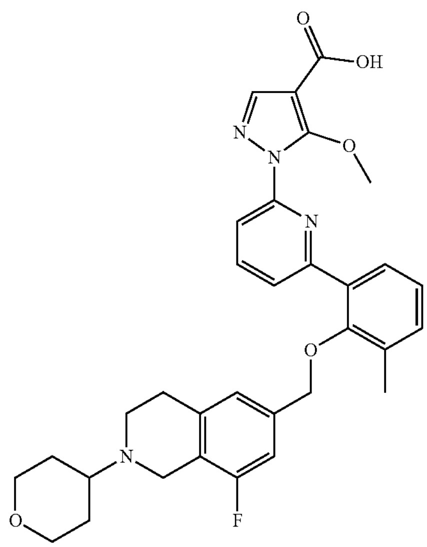 |
| 202 | 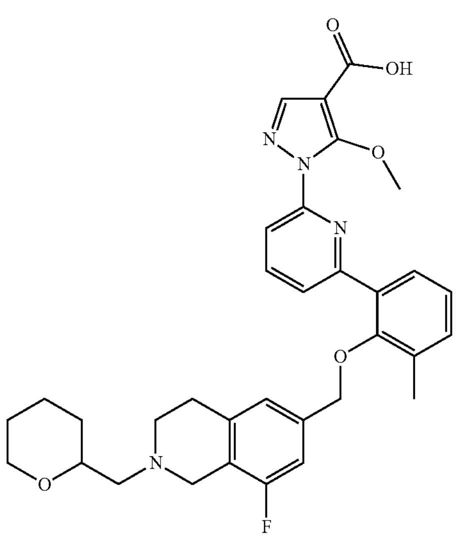 [SMILES: COc1c(C(=O)O)cnn1-c1cccc(-c2cccc(C)c2OCc2cc(F)c3c(c2)CCN(CC2CCCCO2)C3)n1] |
| 203 | |
| 204 | |
| 205 | |

TABLE 1-continued
| Cpd No. | Structure |
|---|---|
| 206 | 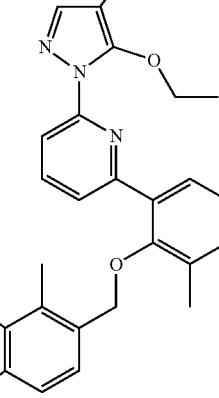 |
| 207 | |
| 208 | |
TABLE 1-continued
| Cpd No. | Structure |
|---|---|
| 209 | 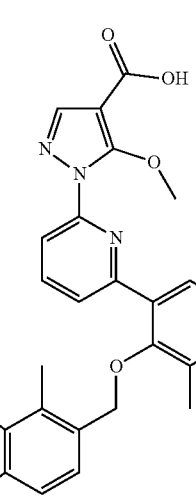 |
| 210 | |
| 211 | 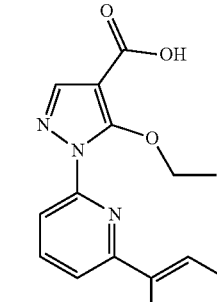 |

TABLE 1-continued

| Cpd No. | Structure |
|---|---|
| 212 | 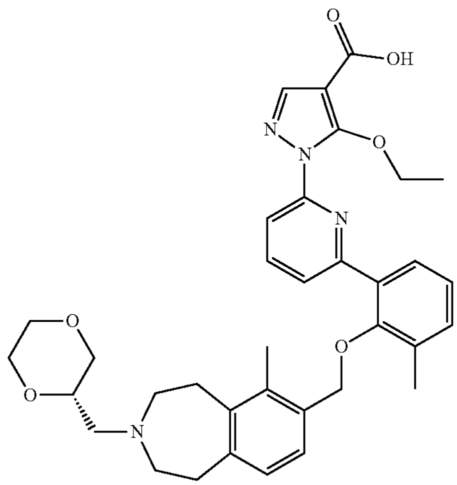 [SMILES: CCOc1c(C(=O)O)cnn1-c1cccc(-c2cccc(C)c2OCc2ccc3c(c2C)CCN(C[C@H]2COCCO2)CC3)n1] |
| 213 | 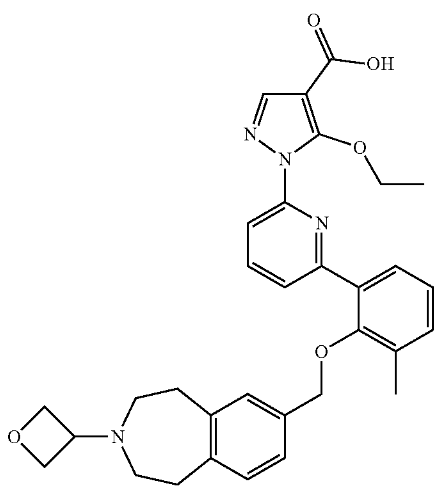 [SMILES: CCOc1c(C(=O)O)cnn1-c1cccc(-c2cccc(C)c2OCc2ccc3c(c2)CCN(C2COC2)CC3)n1] |
| 214 | 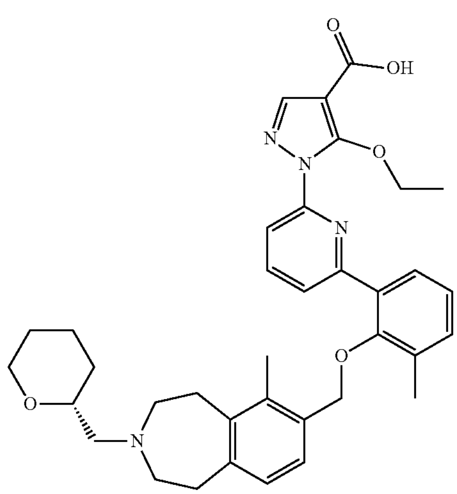 |
| 215 | |
| 216 | |
| 217 | |

TABLE 1-continued
| Cpd No. | Structure |
|---|---|
| 218 | 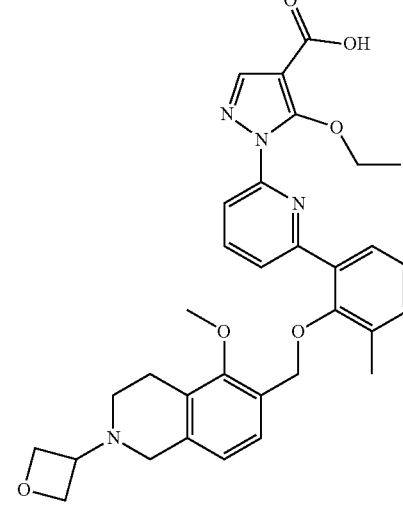 |
| 219 | |
| 220 | |
TABLE 1-continued
| Cpd No. | Structure |
|---|---|
| 221 | 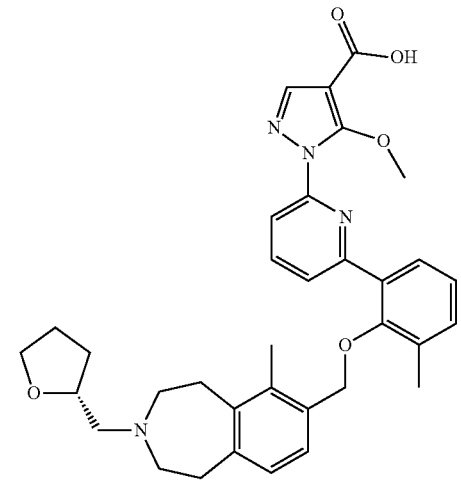 |
| 222 | 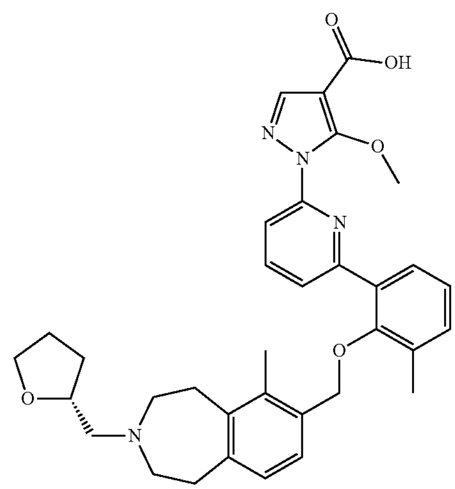 [SMILES: COc1c(C(=O)O)cnn1-c1cccc(-c2cccc(C)c2OCc2ccc3c(c2C)CCN(C[C@H]2CCCO2)CC3)n1] |
| 223 | 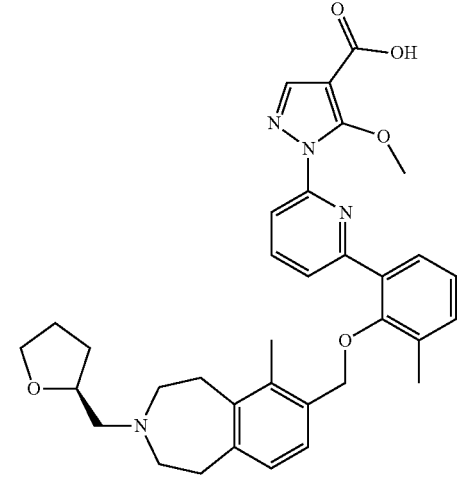 [SMILES: COc1c(C(=O)O)cnn1-c1cccc(-c2cccc(C)c2OCc2ccc3c(c2C)CCN(C[C@@H]2CCCO2)CC3)n1] |

TABLE 1-continued

| Cpd No. | Structure |
|---|---|
| 224 | 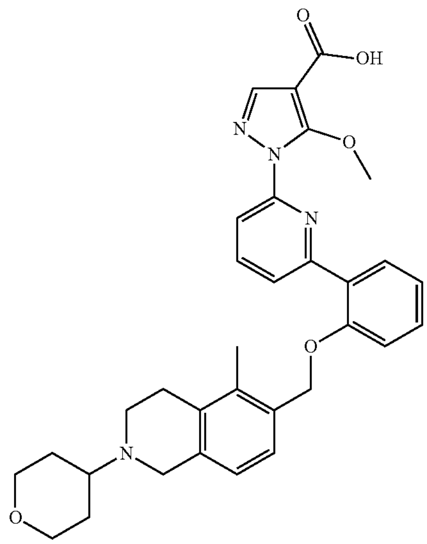 [SMILES: COc1c(C(=O)O)cnn1-c1cccc(-c2ccccc2OCc2ccc3c(c2C)CCN(C2CCOCC2)C3)n1] |
| 225 | 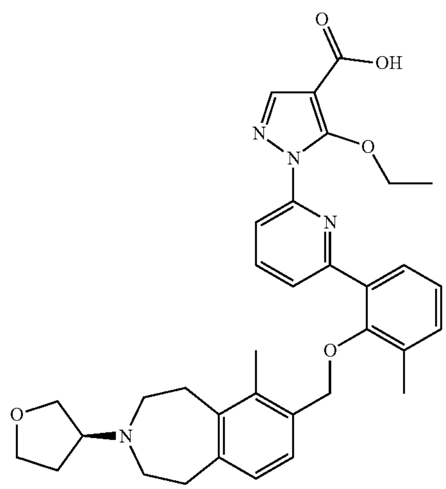 [SMILES: CCOc1c(C(=O)O)cnn1-c1cccc(-c2cccc(C)c2OCc2ccc3c(c2C)CCN([C@H]2CCOC2)CC3)n1] |
| 226 | 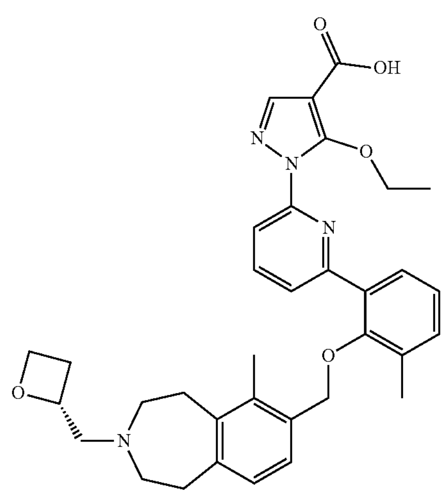 [SMILES: CCOc1c(C(=O)O)cnn1-c1cccc(-c2cccc(C)c2OCc2ccc3c(c2C)CCN(C[C@H]2CCO2)CC3)n1] |
| 227 | |
| 228 | |
| 229 | |

TABLE 1-continued

| Cpd No. | Structure |
|---|---|
| 230 | 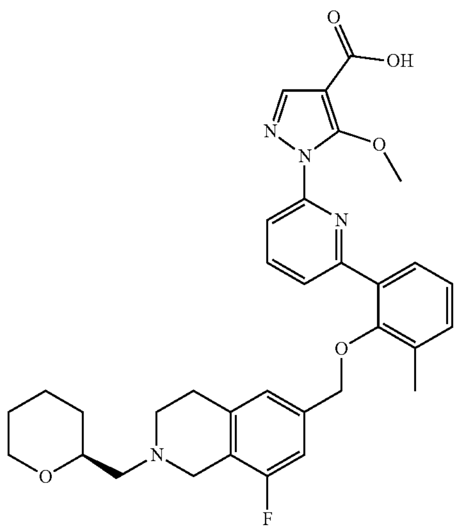 [SMILES: COc1c(C(=O)O)cnn1-c1cccc(-c2cccc(C)c2OCc2cc(F)c3c(c2)CCN(C[C@@H]2CCCCO2)C3)n1] |
| 231 | 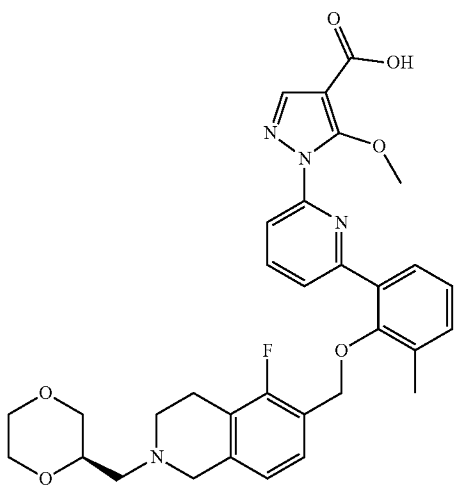 [SMILES: COc1c(C(=O)O)cnn1-c1cccc(-c2cccc(C)c2OCc2ccc3c(c2F)CCN(C[C@@H]2COCCO2)C3)n1] |
| 232 | 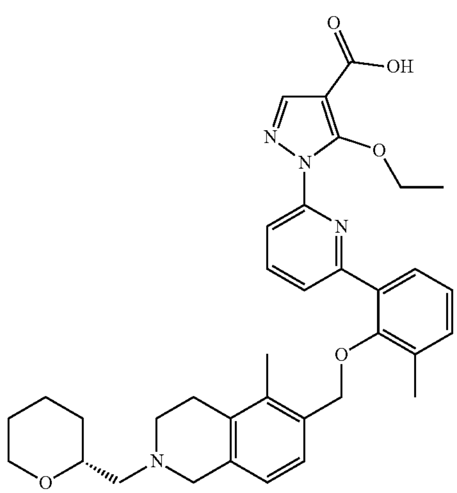 [SMILES: CCOc1c(C(=O)O)cnn1-c1cccc(-c2cccc(C)c2OCc2ccc3c(c2C)CCN(C[C@H]2CCCCO2)C3)n1] |
| 233 | |
| 234 | |
| 235 | |

TABLE 1-continued
| Cpd No. | Structure |
|---|---|
| 236 | 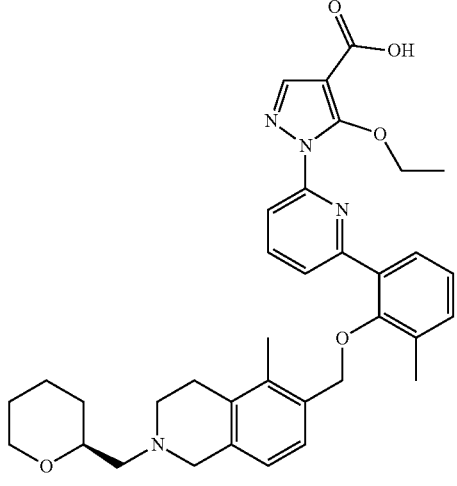 [SMILES: CCOc1c(C(=O)O)cnn1-c1cccc(-c2cccc(C)c2OCc2ccc3c(c2C)CCN(C[C@@H]2CCCCO2)C3)n1] |
| 237 | 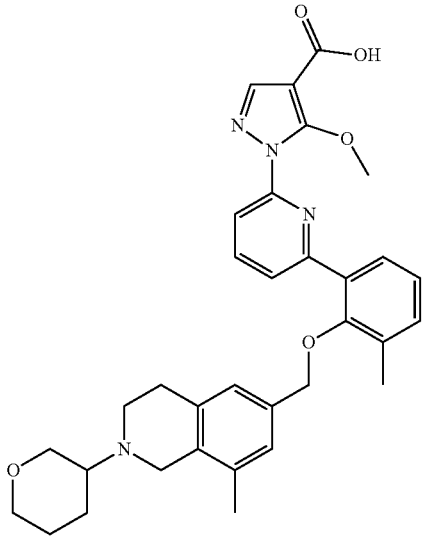 [SMILES: COc1c(C(=O)O)cnn1-c1cccc(-c2cccc(C)c2OCc2cc(C)c3c(c2)CCN(C2CCCOC2)C3)n1] |
| 238 | 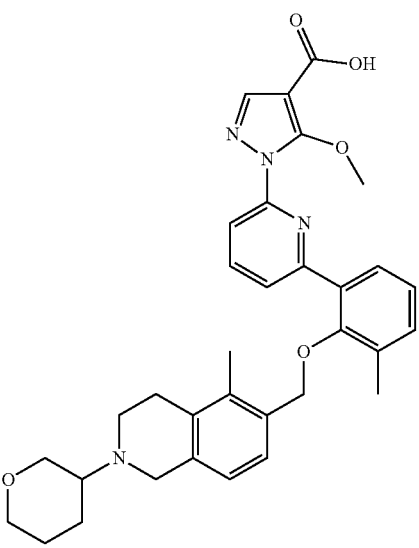 [SMILES: COc1c(C(=O)O)cnn1-c1cccc(-c2cccc(C)c2OCc2ccc3c(c2C)CCN(C2CCCOC2)C3)n1] |
TABLE 1-continued
| Cpd No. | Structure |
|---|---|
| 239 | 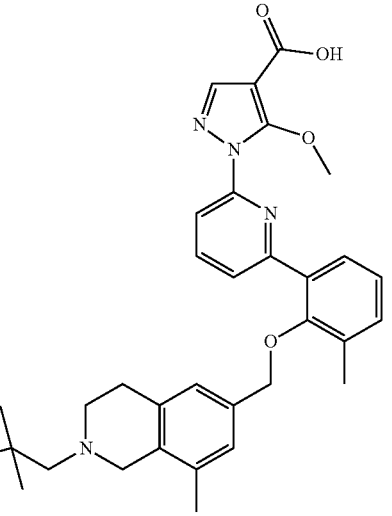 |
| 240 | 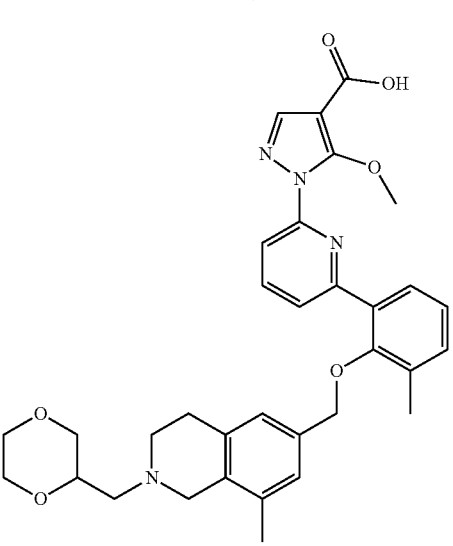 |
| 241 | 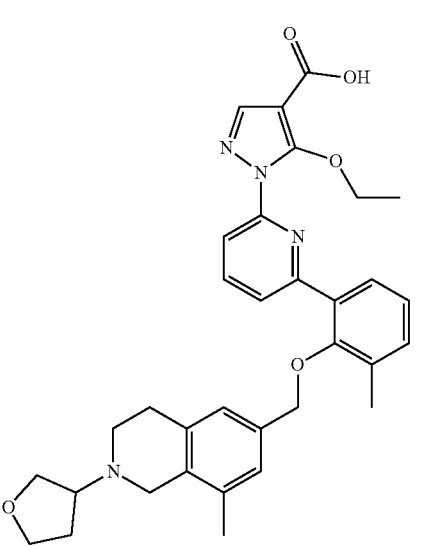 [SMILES: CCOc1c(C(=O)O)cnn1-c1cccc(-c2cccc(C)c2OCc2cc(C)c3c(c2)CCN(C2CCOC2)C3)n1] |

TABLE 1-continued

| Cpd No. | Structure |
|---|---|
| 242 | (structure) |
| 243 | (structure) |
| 244 | (structure) |
| 245 | (structure) |
| 246 | (structure) |
| 247 | (structure) |

TABLE 1-continued

| Cpd No. | Structure |
|---|---|
| 248 | 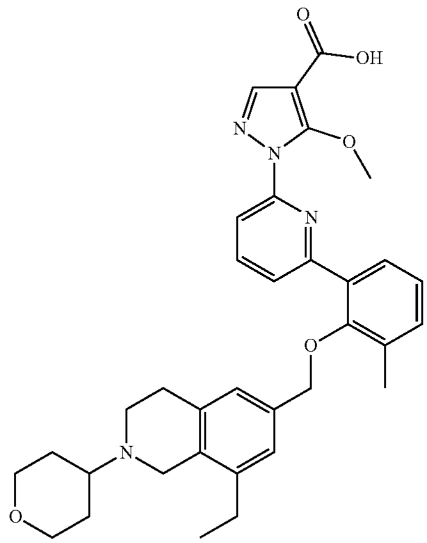 [SMILES: CCc1cc(COc2c(C)cccc2-c2cccc(-n3ncc(C(=O)O)c3OC)n2)cc2c1CN(C1CCOCC1)CC2] |
| 249 | 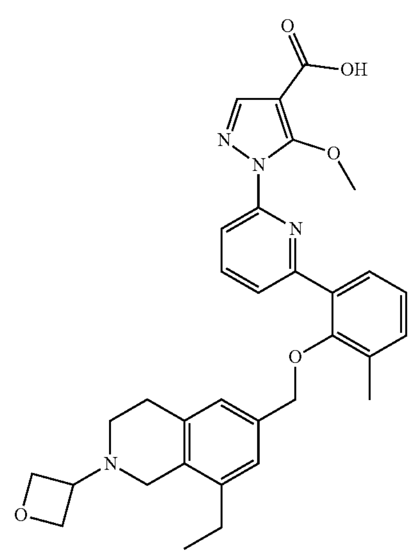 [SMILES: CCc1cc(COc2c(C)cccc2-c2cccc(-n3ncc(C(=O)O)c3OC)n2)cc2c1CN(C1COC1)CC2] |
| 250 | |
| 251 | |

TABLE 1-continued

| Cpd No. | Structure |
|---|---|
| 252 | 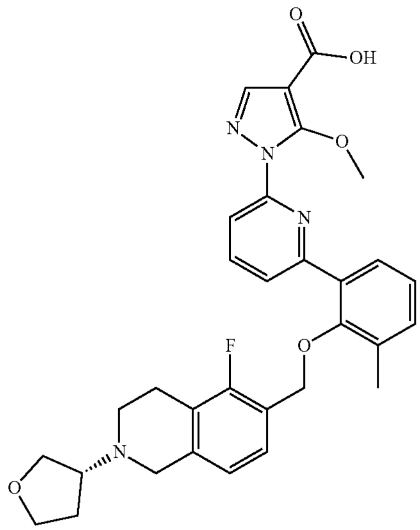 [SMILES: COc1c(C(=O)O)cnn1-c1cccc(-c2cccc(C)c2OCc2ccc3c(c2F)CCN([C@@H]2CCOC2)C3)n1] |
| 253 | 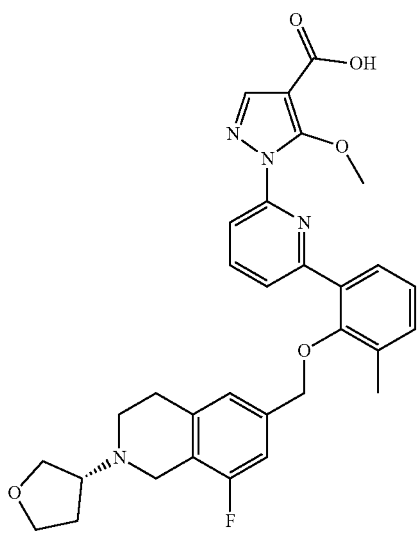 [SMILES: COc1c(C(=O)O)cnn1-c1cccc(-c2cccc(C)c2OCc2cc(F)c3c(c2)CCN([C@@H]2CCOC2)C3)n1] |
| 254 | 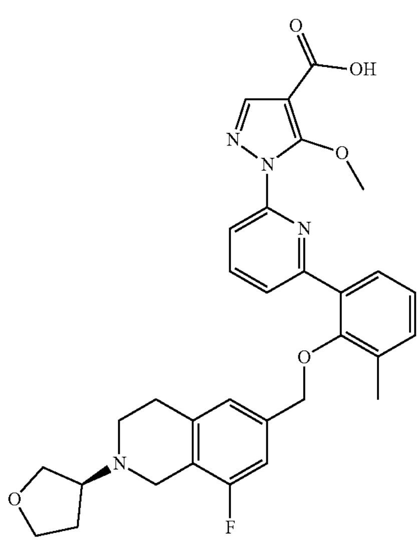 [SMILES: COc1c(C(=O)O)cnn1-c1cccc(-c2cccc(C)c2OCc2cc(F)c3c(c2)CCN([C@H]2CCOC2)C3)n1] |
| 255 | |
| 256 | |

TABLE 1-continued

| Cpd No. | Structure |
|---|---|
| 257 | 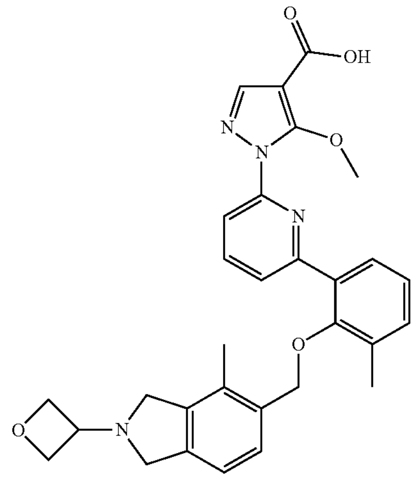 [SMILES: COc1c(C(=O)O)cnn1-c1cccc(-c2cccc(C)c2OCc2ccc3c(c2C)CN(C2COC2)C3)n1] |
| 258 | 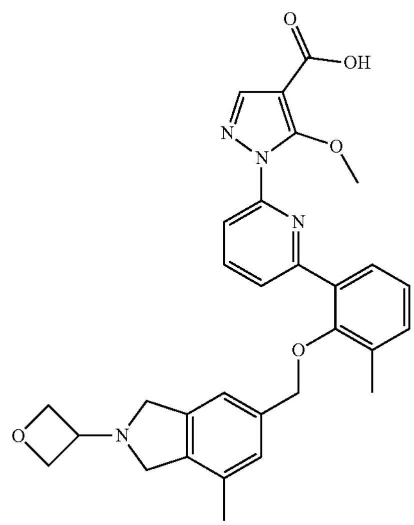 [SMILES: COc1c(C(=O)O)cnn1-c1cccc(-c2cccc(C)c2OCc2cc(C)c3c(c2)CN(C2COC2)C3)n1] |

In another embodiment, the invention relates to the method of embodiment (I) described above, wherein the compound of formula (I) is selected from the group consisting of compound number 1, 2, 3, 4, 5, 7, 8, 9, 12, 15, 16, 18, 21, 27, 28, 30, 31, 35, 36, 39, 41, 42, 44, 45, 46, 47, 48, 57, 59, 62, 68, 77, 78, 79, 80, 82, 83, 84, 85, 86, 88, 92, 93, and 94 and the pharmaceutically acceptable salts thereof.

In another embodiment, the invention relates to the method of embodiment (I) described above, wherein the compound of formula (I) is selected from the group consisting of compound number 95, 97, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 136, 137, 139, 140, 141, 142, 145, 146, 152, 153, 154, 155, 157, 158, 159, 161, 162, 163, 164, 165, 166, 167, 169, 170, 171, 172, 173, 174, 175, 176, 177, 178, 179, 180, 181, 184, 185, 186, 187, 188, 189, 191, 193, 194, 195, 196, 197, 198, 199, 201, 202, 203, 204, 205, 206, 207, 208, 210, 211, 212, 213, 214, 215, 216, 220, 222, 223, 224, 225, 227, 229, 230, 231, 232, 233, 234, 235, 236, 237, 238, 239, 240, 241, 242, 243, 244, 246, 247, 248, 249, 250, 251, 252, 253, 254, 255, 256, 257 and the pharmaceutically acceptable salts thereof.

In another embodiment, the invention relates to methods of treating a disease or disorder that can be alleviated by sGC activation or potentiation, the method comprising administer to a patient in need thereof a pharmaceutically effective amount of a compound of formula (Ia)

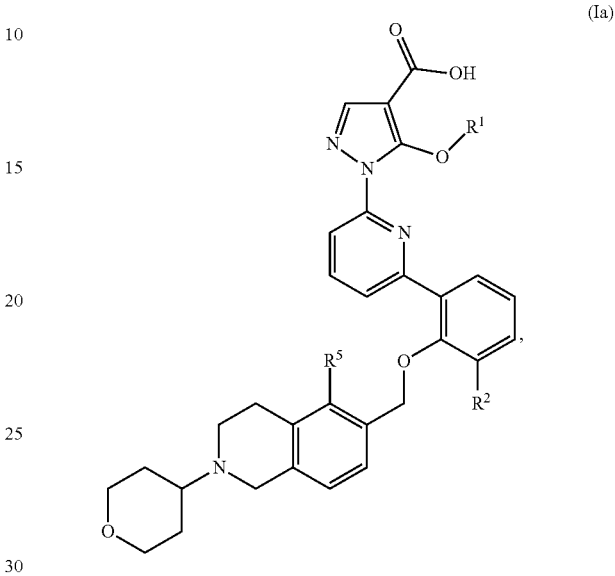

(Ia)

or the pharmaceutically acceptable salts thereof, wherein $R^1$ is $C_{1-4}$ alkyl;

$R^2$ is $C_{1-3}$ alkyl; and $R^5$ is selected from F, Cl, —CH$_3$, and —CH$_2$CH$_3$, wherein the disease or disorder is selected from the group consisting of chronic liver diseases, NASH, cirrhosis and portal hypertension.

In another embodiment, the invention relates to the embodiment described immediately above, wherein the compound of formula (Ia) is selected from the group consisting of compound number 18, 27, 84, 114, 133, 134, 136, 148, 154, 165, and 167, and pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (Also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency,' or a 'carbanion' are not compounds contemplated by the inventive methods disclosed herein.

For all compounds disclosed herein above in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH2CHF2, —CF3 etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—C1-6 alkyl radical, unless otherwise specified, this shall be understood to include —S(O)—C1-6 alkyl and —S(O)2—C1-6 alkyl, likewise, —S—Ra may be represented as phenyl-S(O)m— when Ra is phenyl and where m is 0, 1 or 2.

Methods of Therapeutic Use

The compounds disclosed herein effectively activate soluble guanylate cyclase. The activation or potentiation of soluble guanylate cyclase is an attractive means for preventing and treating certain diseases and disorders.

According to an embodiment of this aspect the invention relates to a method for treating, preventing, slowing the progression of non-alcoholic steatohepatitis (NASH), in a patient in need thereof characterized in that a pharmaceutical composition or pharmaceutical dosage form as defined hereinbefore and hereinafter is administered to the patient.

In one embodiment, the compounds of the invention may be used for treating NASH with fibrosis, for example, F1 to F4.

In another embodiment, the compounds of the invention may be used for treating cirrhosis with and without clinical significant portal hypertension.

In another embodiment, the invention relates to treatment of patients with compensated NASH cirrhosis with clinically significant portal hypertension (CSPH). Portal venous pressure is the blood pressure in the hepatic portal vein, and is normally between 5-10 mmHg. Raised portal venous pressure is termed portal hypertension, and has numerous sequelae such as ascites and hepatic encephalopathy. In one embodiment of the invention, CSPH is defined as a hepatic venous pressure gradient (HVPG) ≥10 mm/Hg. Accordingly, another embodiment of the invention relates to treatment of patients with compensated NASH cirrhosis with a venous pressure gradient (HVPG) ≥10 mm/Hg.

In another embodiment, the invention relates to treatment of portal hypertension in cirrhotic patients, where the cirrhosis is due to any etiology (all-cause cirrhosis). Etiologies include, but are not limited to, NASH, alcoholic liver disease (ALD), hepatitis C, hepatitis B, chronic primary biliary liver diseases (Primary Sclerosing Cholangitis, Primary Biliary Cirrhosis).

According to another aspect the present invention relates to a method for treating non-alcoholic steatohepatitis (NASH, NAS ≥4), in particular of NASH with liver fibrosis, for example of NASH with liver fibrosis stages 2 and 3, in a patient in need thereof characterized in that a pharmaceutical composition comprising a compound of formula (I) or a pharmaceutically acceptable salt thereof as an active pharmaceutical ingredient (API), preferably a pharmaceutical composition according to this invention, is administered to the patient.

In one embodiment, the invention relates to the use of a compound of the invention for the preparation of a medicament for treating, preventing, or slowing the progression of non-alcoholic steatohepatitis (NASH).

In one embodiment, the invention relates to a compound of the invention for use in treating, preventing, or slowing the progression of non-alcoholic steatohepatitis (NASH).

The effect of an administration of said pharmaceutical composition to a patient with NASH and/or liver fibrosis may be observed by a change, in particular reduction of relevant biomarkers of liver inflammation and/or liver function, such as for example ALT (alanine aminotransferase), AST (aspartate aminotransferase), AP (alkaline phosphatase), gamma-GT (gamma-glutamil transferase), CK-18 (cytokeratin 18) fragments or HVPG (hepatic vein pressure gradient).

Furthermore the effect of an administration of said pharmaceutical composition to a patient with NASH and/or liver fibrosis may be observed by an improvement of for example the degree or stage of steatosis, fibrosis, liver stiffness or health-related quality of life.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

Preferred doses of the compound of the invention for once daily oral administration are 0.1 to 100 mg; or 1 to 25 mg; or 1 to 10 mg; or 2 to 5 mg. In another embodiment, the preferred doses of the API for once daily oral administration are selected from 1 mg, 1.5 mg, 2 mg, 2.5 mg, 3 mg, 3.5 mg, 4, mg, 4.5 mg, 5 mg, 5.5 mg, 6 mg, 6.5 mg, 7 mg, 7.5 mg, 8 mg, 8.5 mg, 9 mg, 9.5 mg, and 10 mg.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

The compounds of this invention may be administered in combination with compounds for improving the metabolic (e.g., obesity, diabetic, inflammatory) condition of the patient. Nonlimiting examples of such compounds include, e.g., SGLT2 inhibitors (e.g., empagliflozin, dapagliflozin, and canagliflozin), DPP-IV inhibitors (e.g., linagliptin, sitagliptin, saxagliptin, vildagliptin, and alogliptin), and glitazones/thiazolidinediones (e.g., pioglitazone and rosiglitazone).

The compounds of this invention may also be administered in combination with compounds useful for treating NASH/including metabolism modulators RAAS inhibitors, lipid modulators anti-fibrotic agents, anti-inflammatory agents, and immunomodulating agents Nonlimiting examples of such NASH combination partners include:

PF-05221304 (Pfizer), Obeticholic acid (Intercept), GS-0976 (Gilead), GS-9674 (Gilead), LJN452 (Novartis), LMB763 (Novartis), MSDC-0602K/Metabolic Solutions (Octeca), EDP-305 (Enanta), INT-767 (Intercept), 0304 (Betagenon), PF-06835919 (Pfizer), Semaglutide (Novo Nordisk), BMS-986036 (BMS), NGM282 (NGM), BMS-986171 (BMS), PF-06865571 (Pfizer), LIK066 (Novartis), ORMD 0801 (Oramed), CER-209 (Cerenis), TVB-2640 (3-V Bioscience), DS102 (Afimmune), MGL-3196 (Madrigal, Roche), VK2809 (Viking), Volixibat (Sanofi, Shire), IONIS-DGAT2Rx (Ionis), AKCEA-ANGPTL3-LRx (Akcea), Gemcabene (Gemphire), MT-3995 (Mitsubishi Tanabe), DUR-928 (Durect), CORT118335 (Corcept), amacizumab (BirdRock/Janssen), Elafibranor (Genfit), GRI-0621 (GRI Bio), Selonsertib (Gilead), Cenicriviroc (Takeda, Allergan), JKB 121 (Taiwan), Saroglitazar (Zydus), IMM-124E (Immuron), Lanifibranor (IVA337) (Inventiva), GR-MD-02 (Galectin), Emricasan (VAY785) (Novartis), Tipelukast (Kyorin, MediciNova), BMS986263 (ND-L02-s201) (BMS), PF-06667272 (Pfizer), Foralumab (Tiziana), and DRX-065 (DeuteRx).

In another embodiment, the NASH combination partner is selected from:

acetyl-CoA carboxylase (ACC) inhibitors (e.g., GS-0976);
amine oxidase, copper containing 3 (AOC3) inhibitors (e.g., BI 1467335 (formerly known as PXS-4728A));
farnesoid X receptor (FXR) agonists (e.g. obeticholic acid);
apoptosis signal-regulating kinase 1 (ASK1) inhibitors (e.g. selonsertib);
C—C chemokine receptor types 2 (CCR2) and 5 (CCR5) antagonists (e.g. ceniriviroc);
caspase inhibitors (e.g. emricasan);
peroxisome proliferator-activated receptor-gamma (PPAR) agonists (e.g. elafibranor);
stearoyl CoA desaturase-1 inhibitors (e.g., aramchol);
vascular adhesion protein-1 (VAP-1) inhibitors (e.g., PXS4728A); and
pioglitazone/vitamin.

Assessment of Biological Activity

Cirrhotic Portal Hypertension:

Compounds of the invention can be tested in a bile duct ligation (BDL) rat model of cirrhotic portal hypertension (PHT) to show that their usefulness for treating diseases with portal hypertension or liver fibrosis/cirrhosis such as Non Alcoholic Steatohepatitis (NASH), Alcoholic Steatohepatitis (ASH) or from any other etiology. A compound of the invention (3 mg/kg and 10 mg/kg) or vehicle (VEH) is gavaged twice daily from weeks 2-4 (BDL). Mean arterial pressure (MAP), heart rate (HR), portal pressure (PP) are measured. Hepatic fibrosis is quantified by hydroxyproline (HP) and chrome aniline blue (CAB) staining. Liver transaminases (AST and ALT) and the target engagement biomarkers, hepatic cGMP can also be measured.

Changes in hydroxyproline concentration, fibrotic area (Chrome aniline dye), portal pressure, and/or liver transaminases demonstrate that compounds of the invention may be used for treating diseases with portal hypertension or liver fibrosis/cirrhosis such as Non Alcoholic Steatohepatitis (NASH), Alcoholic Steatohepatitis (ASH) and chronic liver diseases from any other etiology.

What is claimed is:

1. A method for treating a disease or disorder that can be alleviated by sGC activation, the method comprising administering to a patient in need thereof a pharmaceutically effective amount of a compound of formula I

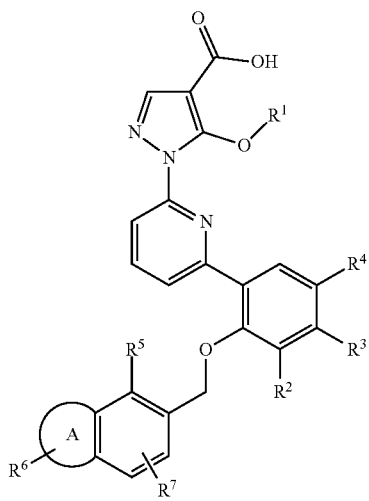

I wherein:

A is a 5-7 membered saturated heterocyclyl group containing one nitrogen and optionally one oxygen, wherein one carbon of said heterocyclyl group is optionally substituted with one or two groups selected from $C_{1-3}$alkyl and oxo;

$R^1$ is $C_{1-4}$ alkyl optionally substituted with a methoxy group;

$R^2$ is selected from H, F, Cl, $C_{1-3}$alkyl, —CN, —OMe and —$CF_3$;

$R^3$ is selected from H and —$CH_3$;

$R^4$ is selected from H, F, —$CH_3$ and —OMe;

$R^5$ is selected from H, Cl, —$CH_3$, —$CH_2CH_3$, —$CF_3$, F, and —OMe;

$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$aryl —$(CH_2)_n$ heteroaryl, —$SO_2$aryl, $SO_2C_{1-6}$alkyl wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH, oxo, —$(CH_2)_{1-3}$O$(CH_2)_{2-3}$OH, and —$SO_2CH_3$;

$R^7$ is absent or selected from the group consisting of —$CH_3$, —$CH_2CH_3$, —$CF_3$, F, and —CN;

n is 0, 1 or 2 or a pharmaceutically acceptable salt thereof, wherein the disease or disorder that is alleviated by sGC activation is portal hypertension.

2. The method according to claim 1, wherein:

A is a 5-7 membered saturated heterocyclyl group containing one nitrogen, wherein one carbon of said heterocyclyl group is optionally substituted with one or two $C_{1-3}$alkyl groups;

$R^1$ is $C_{1-3}$alkyl;

$R^2$ is selected from H, F, Cl, —CN, —OMe and —$CF_3$;

$R^3$ is selected from H and —$CH_3$;

$R^4$ is selected from H and F;

$R^5$ is selected from H, Cl and —$CH_3$;

$R^6$ is bonded to the nitrogen on A and is selected from H, $C_{1-6}$alkyl, —$(CH_2)_nC_{3-6}$cycloalkyl, —$C(O)C_{1-6}$alkyl, —$(CH_2)_n$ heterocyclyl, —$(CH_2)_n$ aryl and —$(CH_2)_n$ heteroaryl, wherein said $C_{1-6}$alkyl, —$(CH_2)_n$ heterocyclyl, —$(CH_2)_n$ cycloalkyl, —$(CH_2)_n$ aryl and —$(CH_2)_n$ heteroaryl are optionally substituted with one to four groups independently selected from $C_{1-3}$alkyl, halogen, $C_{1-3}$alkoxy, —$CF_3$, —OH and —$SO_2CH_3$;

$R^7$ is H;

and n is 0, 1 or 2;

or a pharmaceutically acceptable salt thereof.

3. The method according to claim 1, wherein:

$R^1$ is methyl, ethyl or isopropyl; and the group

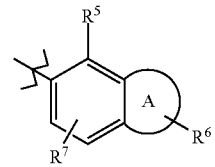

is selected from:

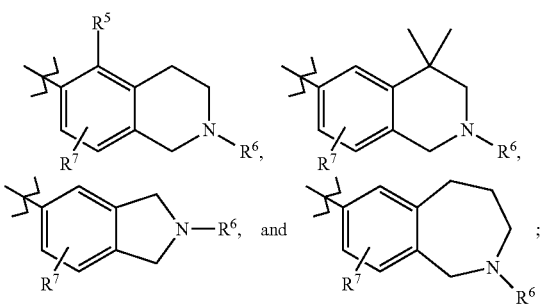

or a pharmaceutically acceptable salt thereof.

4. The method according to claim 1:

$R^2$ is selected from —$CH_3$, F, Cl, and —$CF_3$; and $R^6$ is selected from H, $C_{1-6}$alkyl, —$(CH_2)_nC_{3-6}$cycloalkyl, —$C(O)C_{1-6}$alkyl and —$(CH_2)_n$ heterocyclyl, wherein said $C_{1-6}$alkyl, —$(CH_2)_n$ cycloalkyl and —$(CH_2)_n$ heterocyclyl are optionally substituted with one to four groups independently selected from $C_{1-3}$alkyl, halogen, $C_{1-3}$alkoxy, —$CF_3$, —OH and —$SO_2CH_3$;

or a pharmaceutically acceptable salt thereof.

5. The method according to claim 1, wherein each heterocyclyl referred to in $R^6$ is selected from oxetanyl, tetrahydrofuranyl, tetrahydropyranyl, 2-oxabicyclo-[3.2.0]heptanyl, [1,4]dioxanyl, 8-oxabicyclo[3.2.1]octanyl, 1-oxaspiro[4.5]decanyl and pyrrolidin-2-one;

each heteroaryl referred to in $R^6$ is selected from imidazolyl, isoxazolyl, pyrazinyl, pyrazolyl, pyridinyl, pyrimidinyl, thiazolyl and 4,5,6,7-tetrahydrobenzothiazolyl;

and each aryl referred to in $R^6$ is phenyl;

or a pharmaceutically acceptable salt thereof.

6. The method according to claim 1, wherein:

$R^6$ is —(CH$_2$)$_n$ heterocyclyl, wherein said heterocyclyl is selected from oxetanyl, tetrahydrofuranyl, tetrahydropyranyl, 2-oxabicyclo[3.2.0]heptanyl, [1,4]dioxanyl, 8-oxabicyclo[3.2.1]octanyl and 1-oxaspiro[4.5]decanyl;

or a pharmaceutically acceptable salt thereof.

7. The method according to claim 1, wherein:

$R^2$ is —CH$_3$;
$R^3$ is H;
$R^4$ is H or —CH$_3$;
$R^5$ is H, or —CH$_3$;
$R^7$ is in the position para to $R^5$ and is H, —CH$_3$ or —CH$_2$CH$_3$;

or a pharmaceutically acceptable salt thereof.

8. The method according to claim 1, wherein:

the group

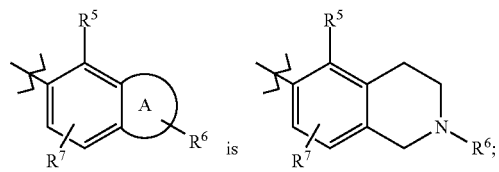

is or a pharmaceutically acceptable salt thereof.

9. The method according to claim 1, wherein:

$R^3$ is H; and
$R^4$ is H;

or a pharmaceutically acceptable salt thereof.

10. The method according to claim 1, wherein the compound is selected from the group consisting of:

| Cpd No. | Structure |
|---|---|
| 1 | 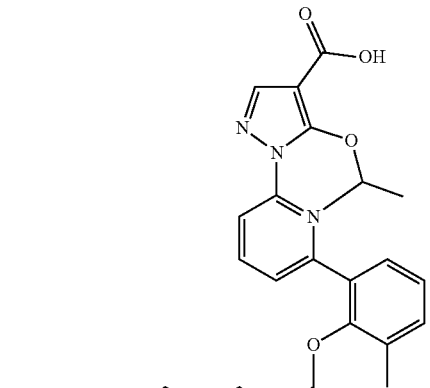 |
| 2 | 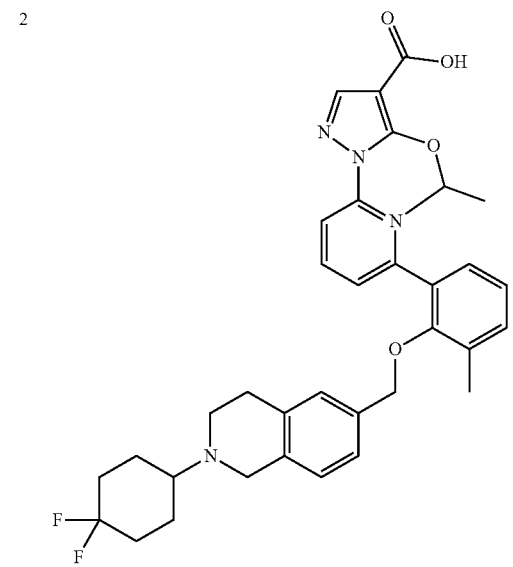 |
| 3 | 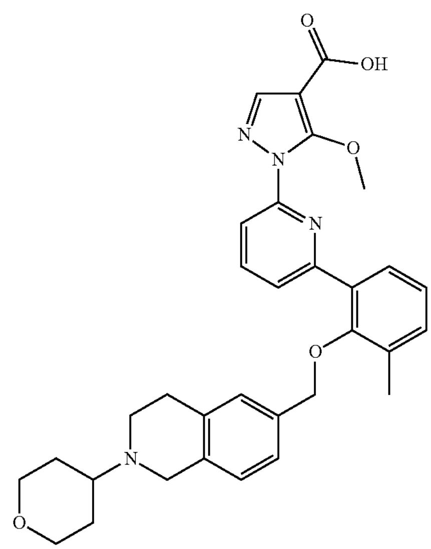 |
| 4 | 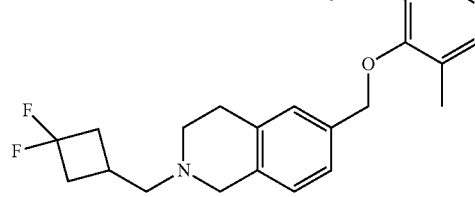 |

| Cpd No. | Structure |
|---|---|
| 5 | 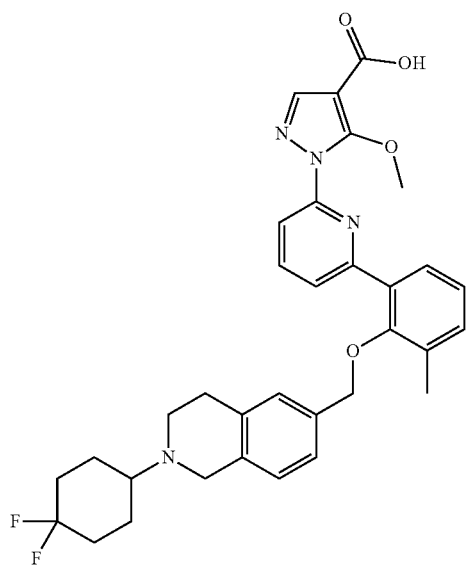 [SMILES: COc1c(C(=O)O)cnn1-c1cccc(-c2cccc(C)c2OCc2ccc3c(c2)CCN(C2CCC(F)(F)CC2)C3)n1] |
| 6 | 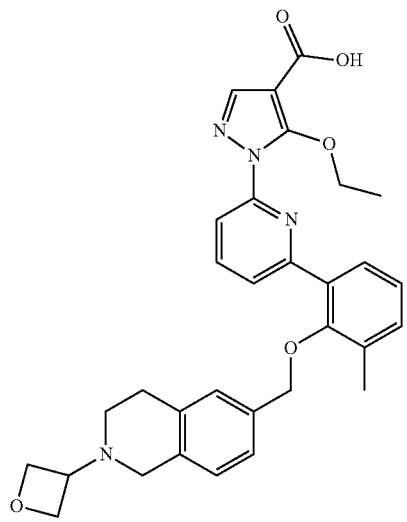 [SMILES: CCOc1c(C(=O)O)cnn1-c1cccc(-c2cccc(C)c2OCc2ccc3c(c2)CCN(C2COC2)C3)n1] |
| Cpd No. | Structure |
|---|---|
| 7 | 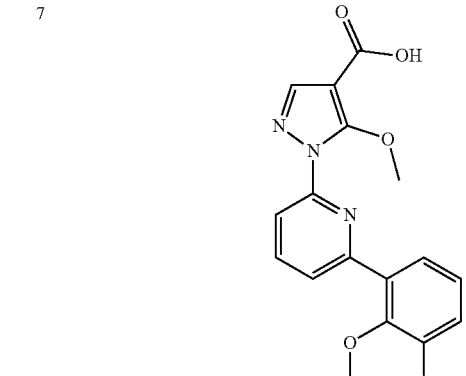 |
| 8 | 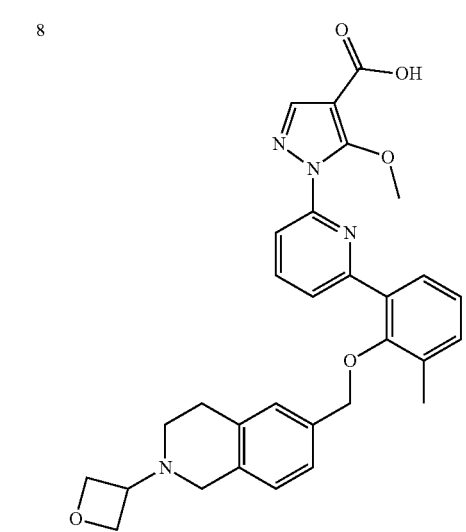 |
| 9 | 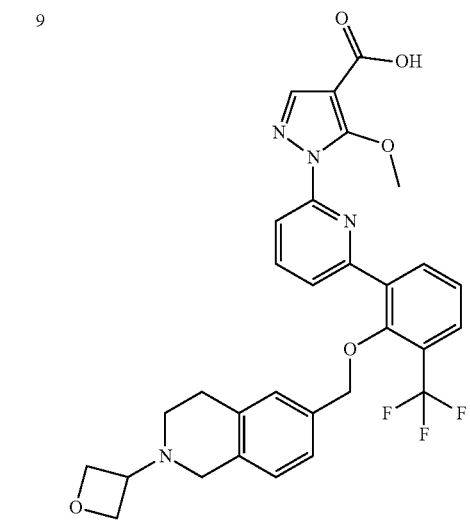 |

| Cpd No. | Structure |
|---|---|
| 10 | 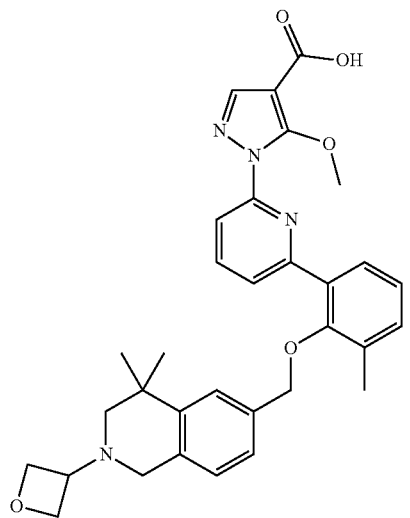 [SMILES: COc1c(C(=O)O)cnn1-c1cccc(-c2cccc(C)c2OCc2ccc3c(c2)C(C)(C)CN(C2COC2)C3)n1] |
| 11 | 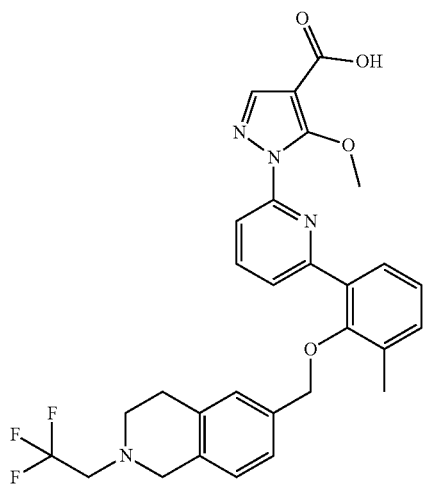 |
| 12 | 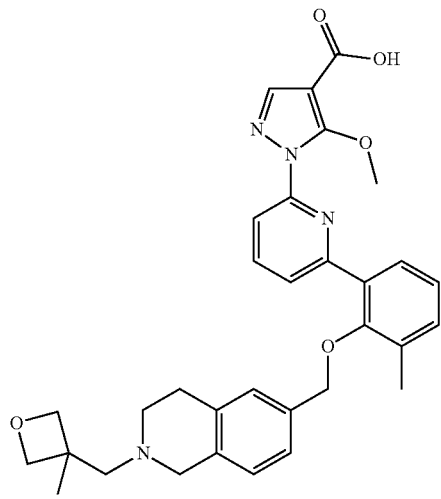 [SMILES: COc1c(C(=O)O)cnn1-c1cccc(-c2cccc(C)c2OCc2ccc3c(c2)CCN(CC2(C)COC2)C3)n1] |
| 13 | 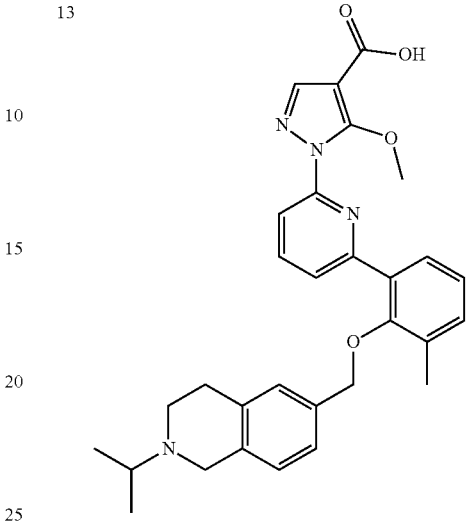 |
| 14 | 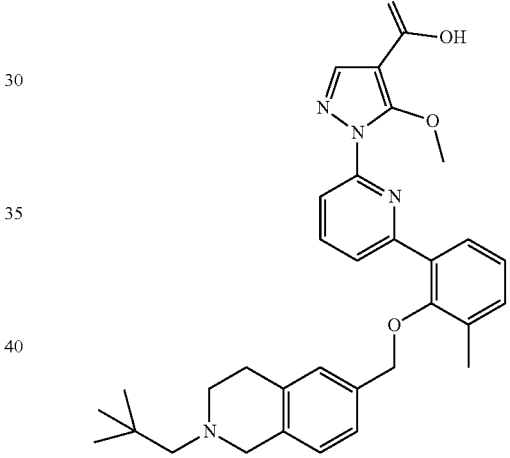 |
| 15 | 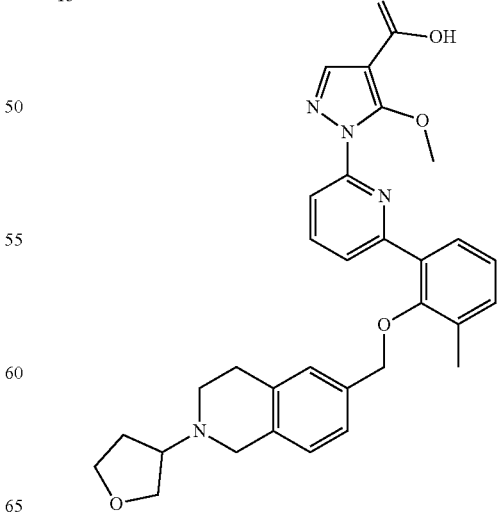 |

-continued
| Cpd No. | Structure |
|---|---|
| 16 | 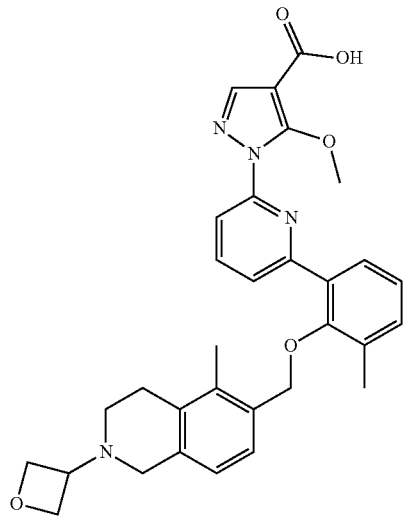 [SMILES: COc1c(C(=O)O)cnn1-c1cccc(-c2cccc(C)c2OCc2ccc3c(c2C)CCN(C2COC2)C3)n1] |
| 17 | 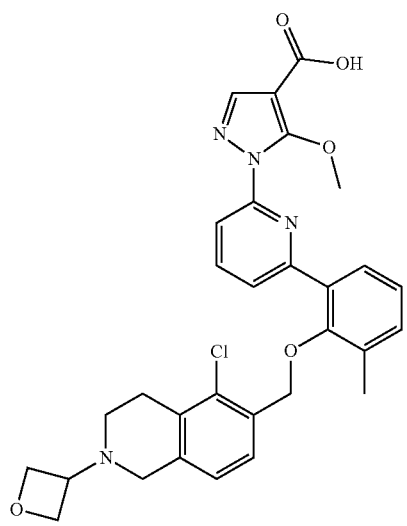 [SMILES: COc1c(C(=O)O)cnn1-c1cccc(-c2cccc(C)c2OCc2ccc3c(c2Cl)CCN(C2COC2)C3)n1] |
| 18 | 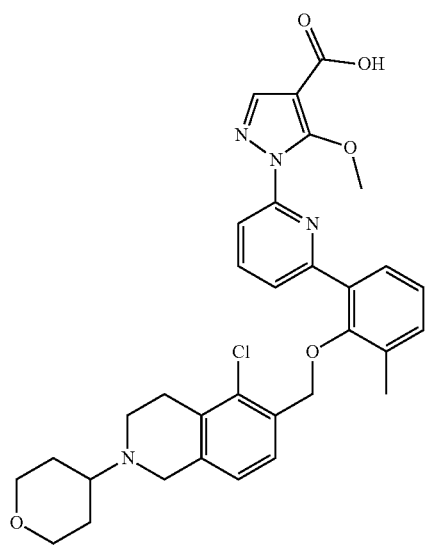 |
-continued
| Cpd No. | Structure |
|---|---|
| 19 | 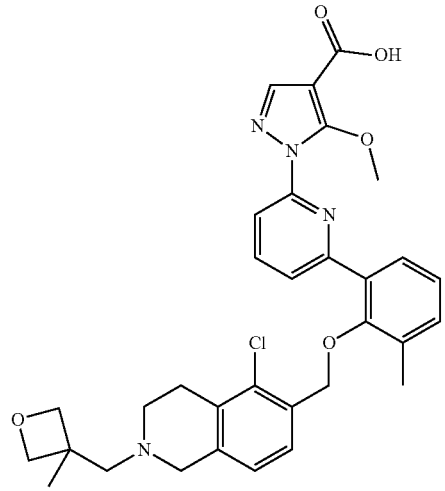 [SMILES: COc1c(C(=O)O)cnn1-c1cccc(-c2cccc(C)c2OCc2ccc3c(c2Cl)CCN(CC2(C)COC2)C3)n1] |
| 20 | 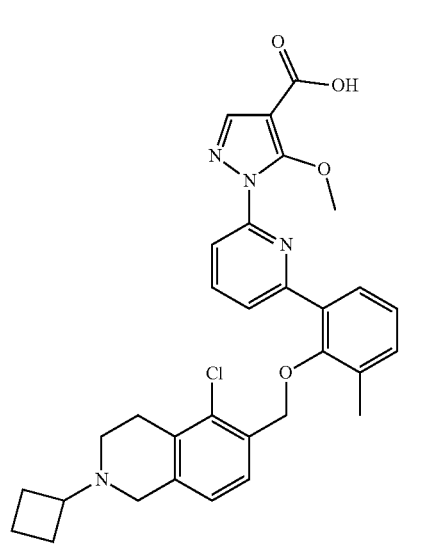 [SMILES: COc1c(C(=O)O)cnn1-c1cccc(-c2cccc(C)c2OCc2ccc3c(c2Cl)CCN(C2CCC2)C3)n1] |
| 21 | 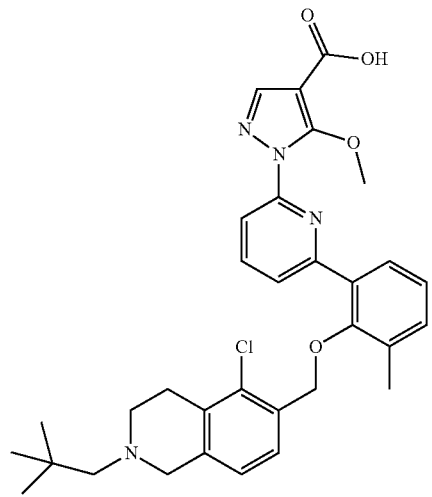 [SMILES: COc1c(C(=O)O)cnn1-c1cccc(-c2cccc(C)c2OCc2ccc3c(c2Cl)CCN(CC(C)(C)C)C3)n1] |

-continued
| Cpd No. | Structure |
|---|---|
| 22 | 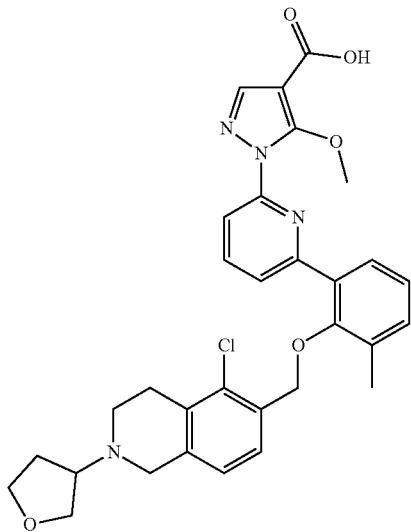 [SMILES: COc1c(C(=O)O)cnn1-c1cccc(-c2cccc(C)c2OCc2ccc3c(c2Cl)CCN(C2CCOC2)C3)n1] |
| 23 | 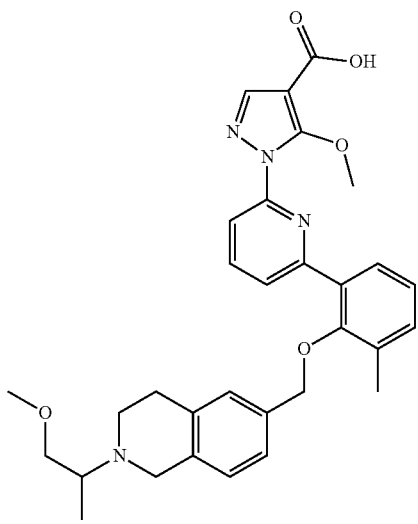 [SMILES: COCC(C)N1CCc2cc(COc3c(C)cccc3-c3cccc(-n4ncc(C(=O)O)c4OC)n3)ccc2C1] |
| 24 | 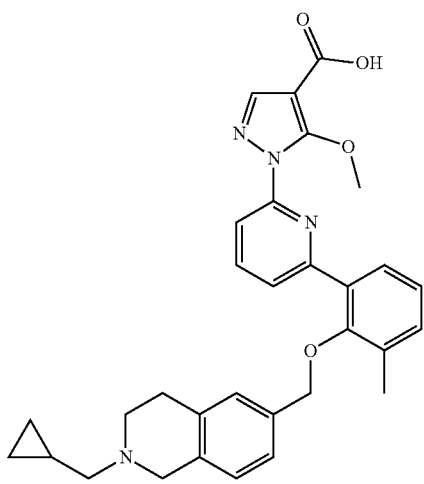 [SMILES: COc1c(C(=O)O)cnn1-c1cccc(-c2cccc(C)c2OCc2ccc3c(c2)CCN(CC2CC2)C3)n1] |
-continued
| Cpd No. | Structure |
|---|---|
| 25 | 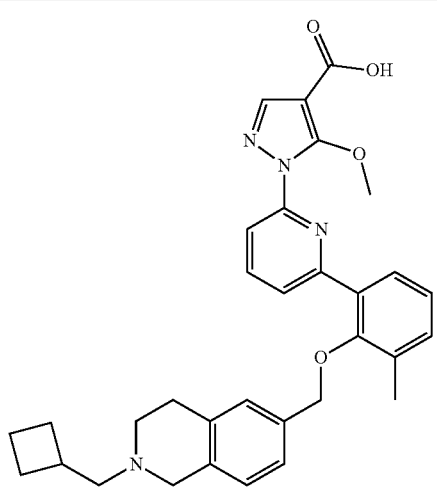 [SMILES: COc1c(C(=O)O)cnn1-c1cccc(-c2cccc(C)c2OCc2ccc3c(c2)CCN(CC2CCC2)C3)n1] |
| 26 | 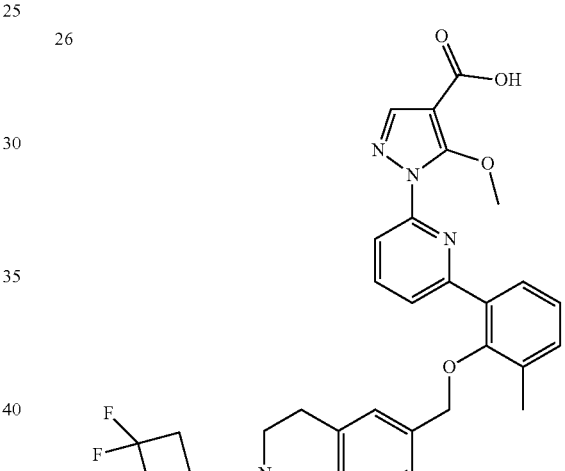 |
| 27 | 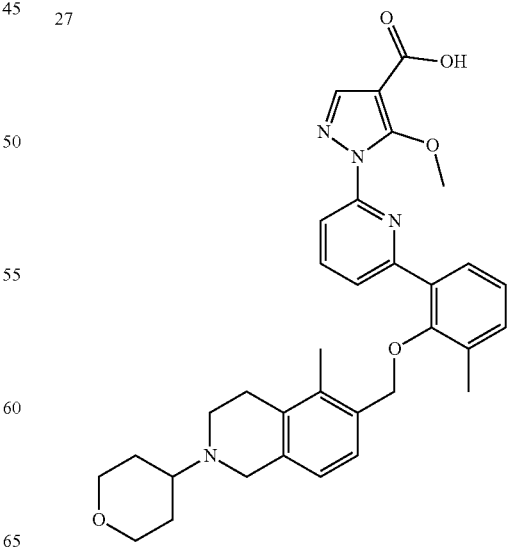 |

| Cpd No. | Structure |
|---|---|
| 28 | 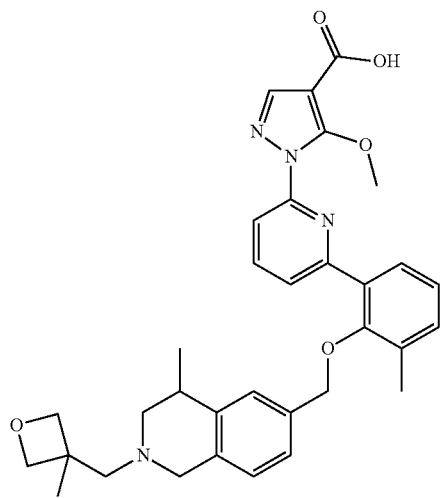 [SMILES: COc1c(C(=O)O)cnn1-c1cccc(-c2cccc(C)c2OCc2ccc3c(c2)C(C)CN(CC2(C)COC2)C3)n1] |
| 29 | 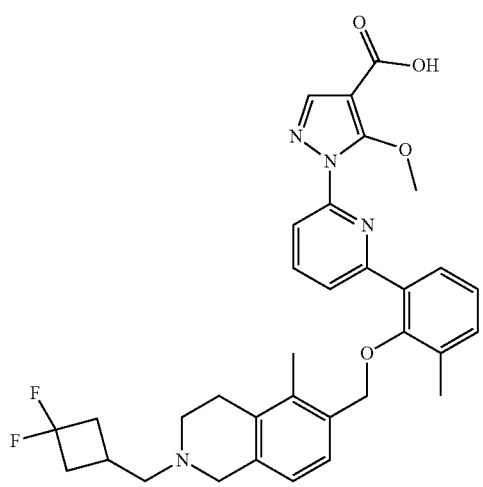 [SMILES: COc1c(C(=O)O)cnn1-c1cccc(-c2cccc(C)c2OCc2ccc3c(c2C)CCN(CC2CC(F)(F)C2)C3)n1] |
| 30 | 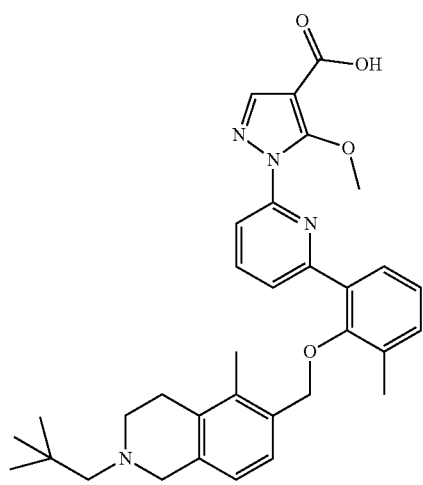 [SMILES: COc1c(C(=O)O)cnn1-c1cccc(-c2cccc(C)c2OCc2ccc3c(c2C)CCN(CC(C)(C)C)C3)n1] |
| 31 | 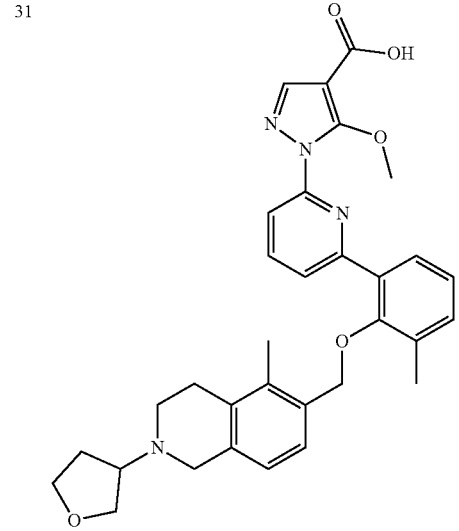 |
| 32 | 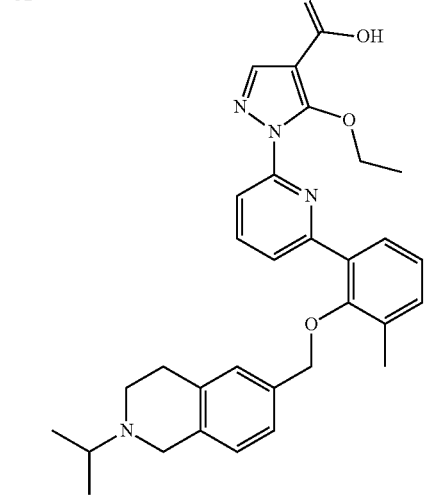 |
| 33 | 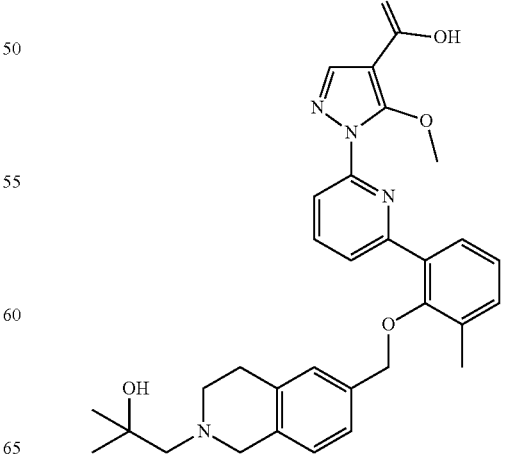 |

| Cpd No. | Structure |
|---|---|
| 34 | 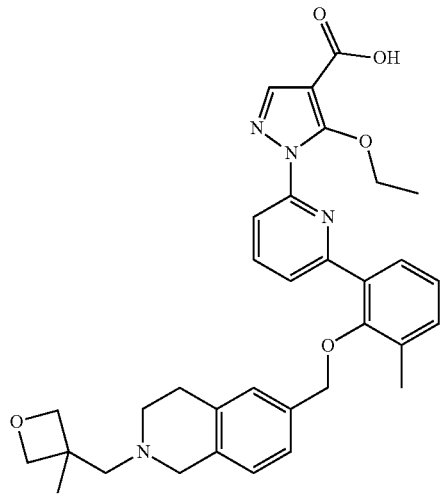 [SMILES: CCOc1c(C(=O)O)cnn1-c1cccc(-c2cccc(C)c2OCc2ccc3c(c2)CCN(CC2(C)COC2)C3)n1] |
| 35 | 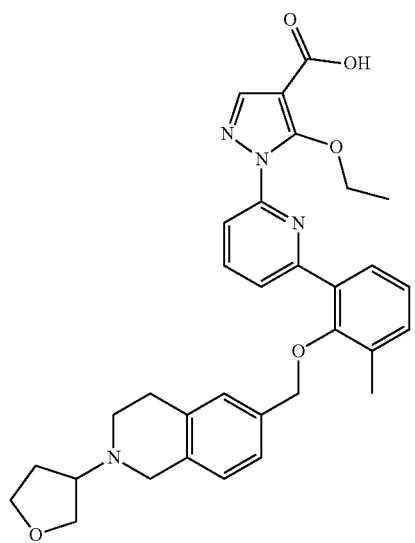 [SMILES: CCOc1c(C(=O)O)cnn1-c1cccc(-c2cccc(C)c2OCc2ccc3c(c2)CCN(C2CCOC2)C3)n1] |
| 336 | 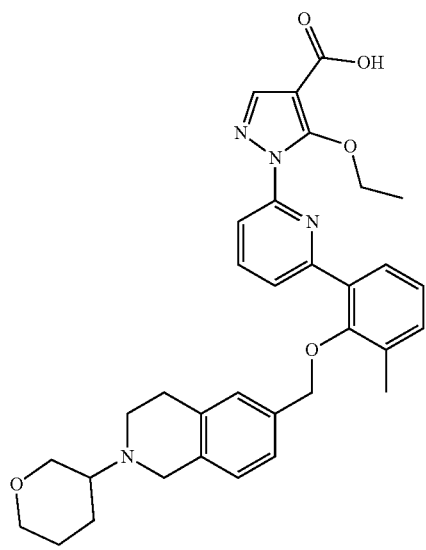 [SMILES: CCOc1c(C(=O)O)cnn1-c1cccc(-c2cccc(C)c2OCc2ccc3c(c2)CCN(C2CCCOC2)C3)n1] |
| Cpd No. | Structure |
|---|---|
| 37 | 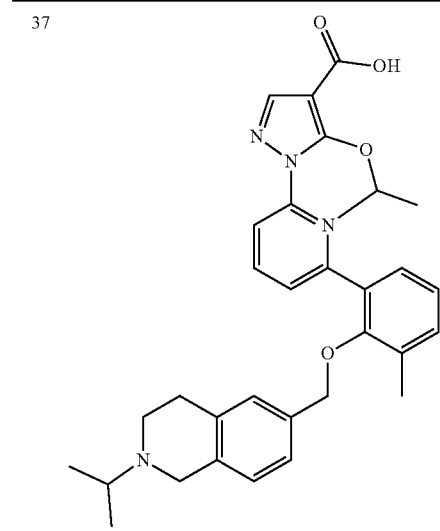 |
| 38 | 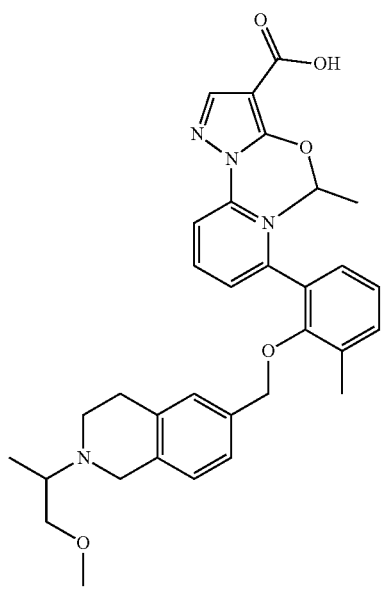 |

TABLE-continued
| Cpd No. | Structure |
|---|---|
| 39 | 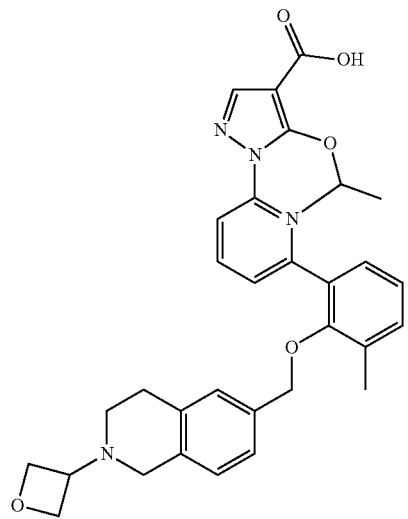 |
| 40 | 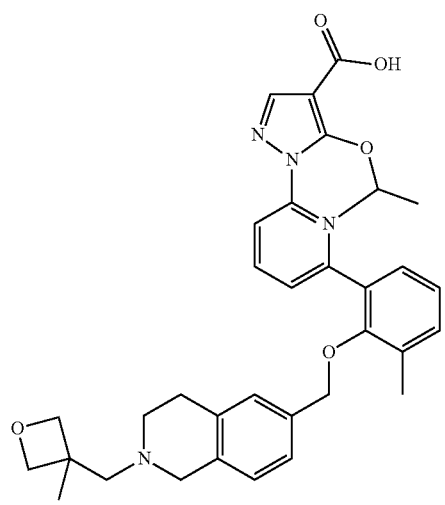 |
| 41 | 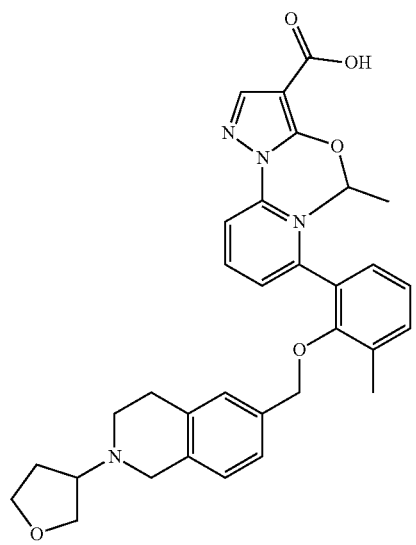 |
| Cpd No. | Structure |
|---|---|
| 42 | 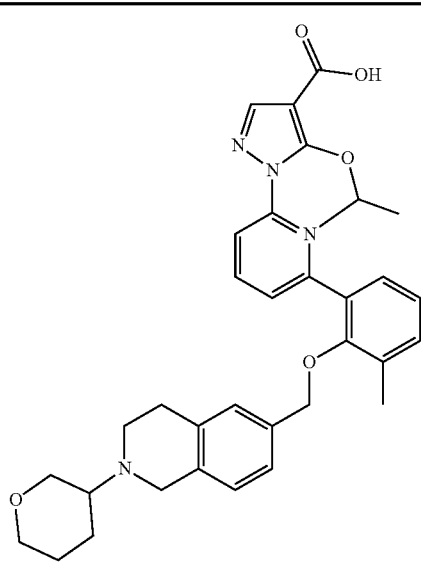 |
| 43 | 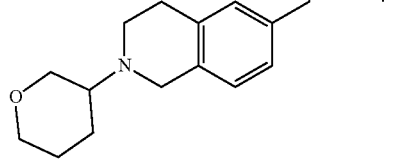 |

| Cpd No. | Structure |
|---|---|
| 44 | 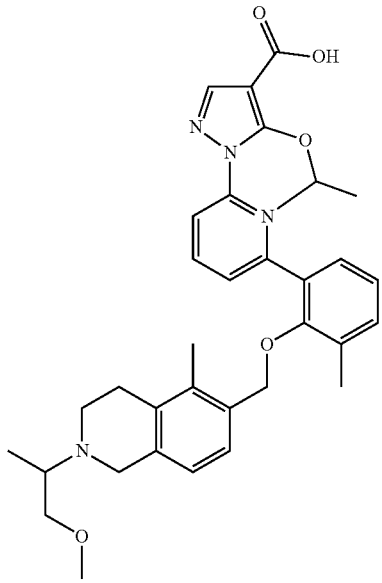 |
| 45 | 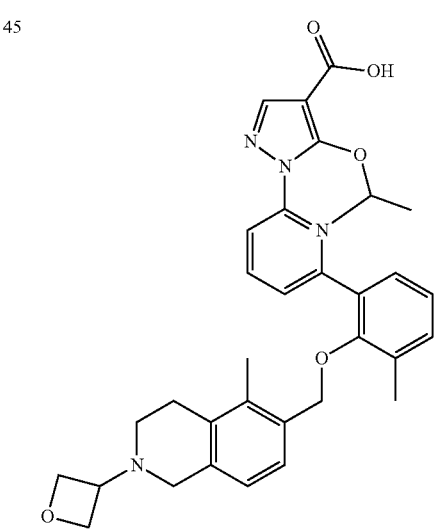 |
| 46 | 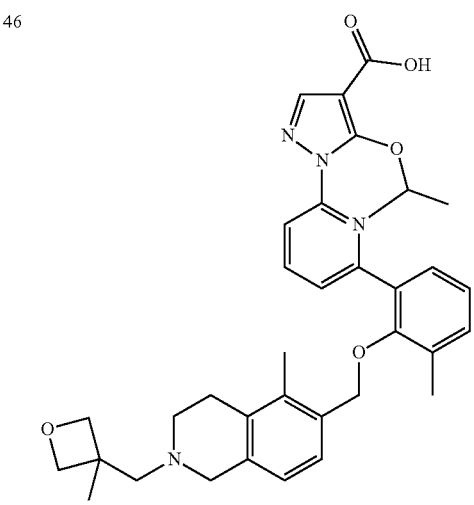 |
| Cpd No. | Structure |
|---|---|
| 47 | 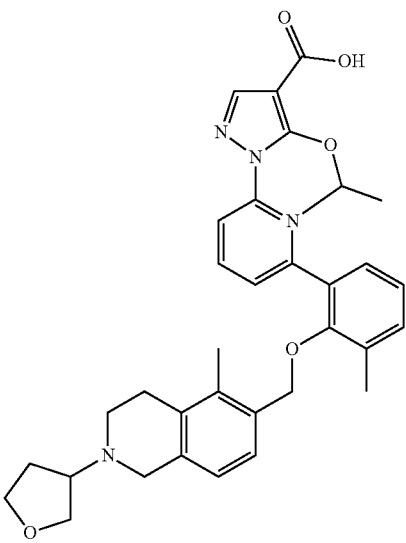 |
| 48 | 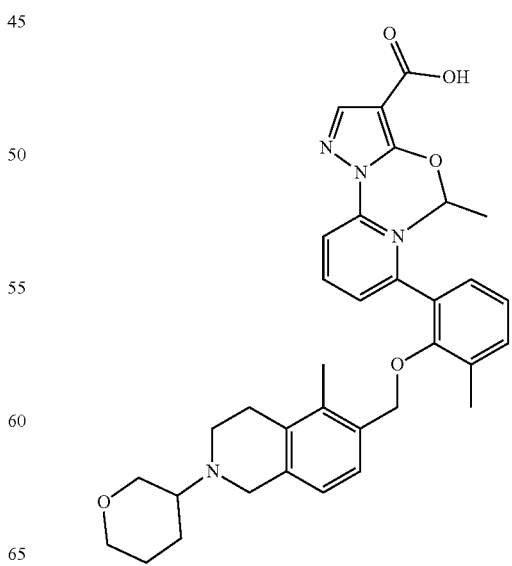 |

| Cpd No. | Structure |
|---|---|
| 49 | 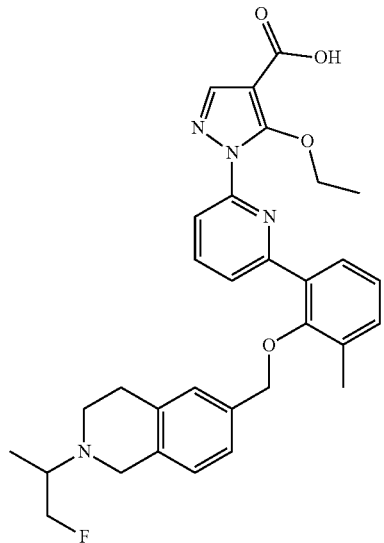 [SMILES: CCOc1c(C(=O)O)cnn1-c1cccc(-c2cccc(C)c2OCc2ccc3c(c2)CCN(C(C)CF)C3)n1] |
| 50 | 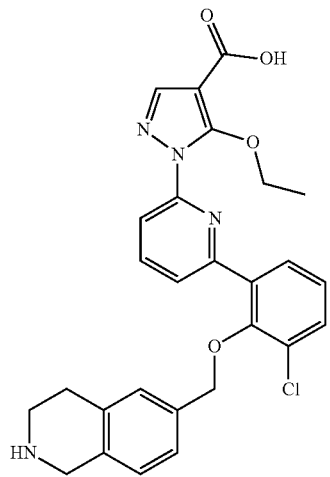 [SMILES: CCOc1c(C(=O)O)cnn1-c1cccc(-c2cccc(Cl)c2OCc2ccc3c(c2)CCNC3)n1] |
| 51 | 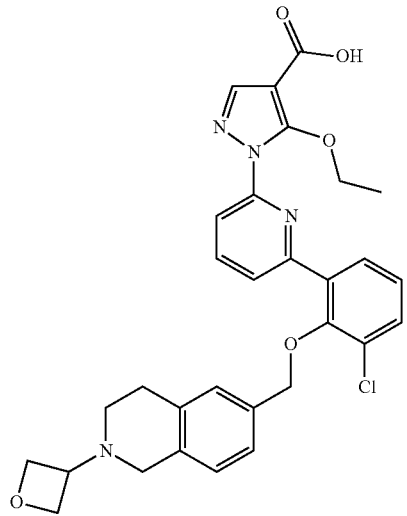 [SMILES: CCOc1c(C(=O)O)cnn1-c1cccc(-c2cccc(Cl)c2OCc2ccc3c(c2)CCN(C2COC2)C3)n1] |
| Cpd No. | Structure |
|---|---|
| 52 | 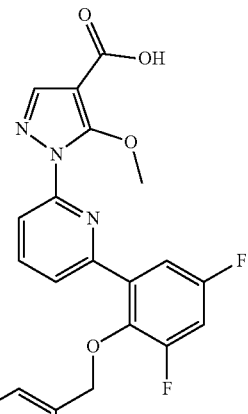 |
| 53 | |
| 54 | |

-continued
| Cpd No. | Structure |
|---|---|
| 55 | 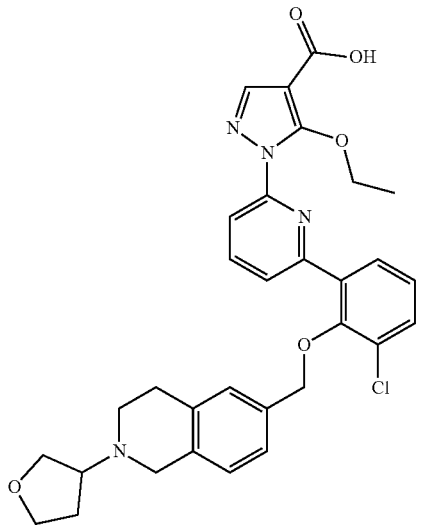 [SMILES: CCOc1c(C(=O)O)cnn1-c1cccc(-c2cccc(Cl)c2OCc2ccc3c(c2)CCN(C2CCOC2)C3)n1] |
| 56 | 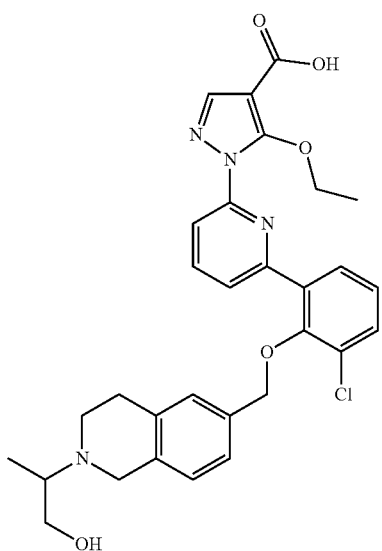 [SMILES: CCOc1c(C(=O)O)cnn1-c1cccc(-c2cccc(Cl)c2OCc2ccc3c(c2)CCN(C(C)CO)C3)n1] |
-continued
| Cpd No. | Structure |
|---|---|
| 57 | 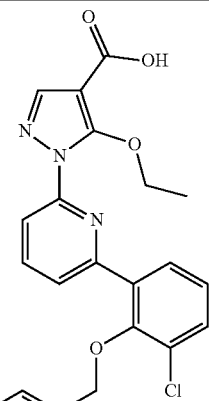 |
| 58 | 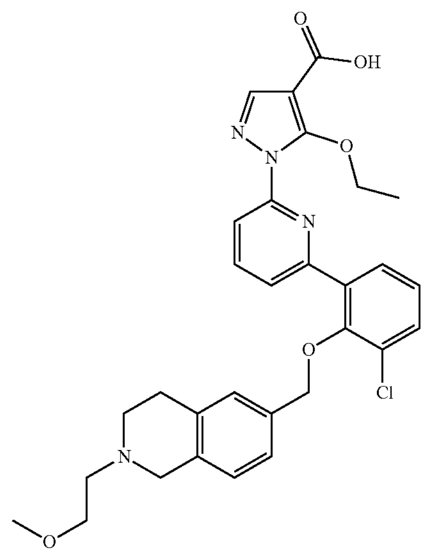 [SMILES: CCOc1c(C(=O)O)cnn1-c1cccc(-c2cccc(Cl)c2OCc2ccc3c(c2)CCN(CCOC)C3)n1] |
| 59 | 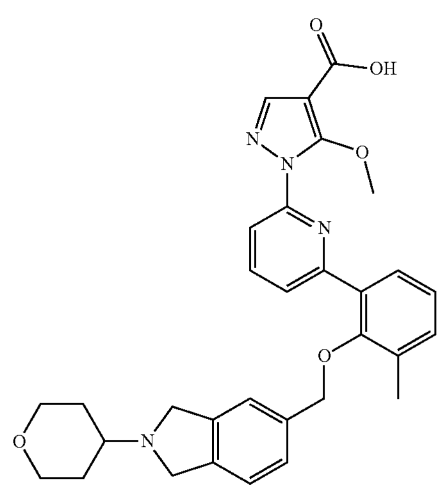 [SMILES: COc1c(C(=O)O)cnn1-c1cccc(-c2cccc(C)c2OCc2ccc3c(c2)CN(C2CCOCC2)C3)n1] |

TABLE-continued
| Cpd No. | Structure |
|---|---|
| 60 | 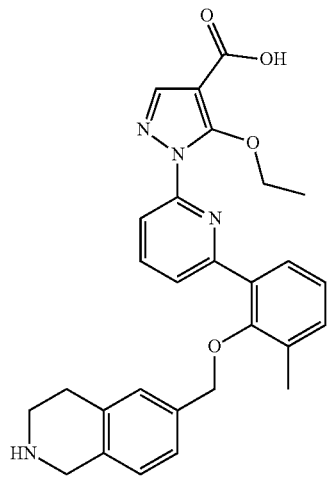 [SMILES: CCOc1c(C(=O)O)cnn1-c1cccc(-c2cccc(C)c2OCc2ccc3c(c2)CCNC3)n1] |
| 61 | 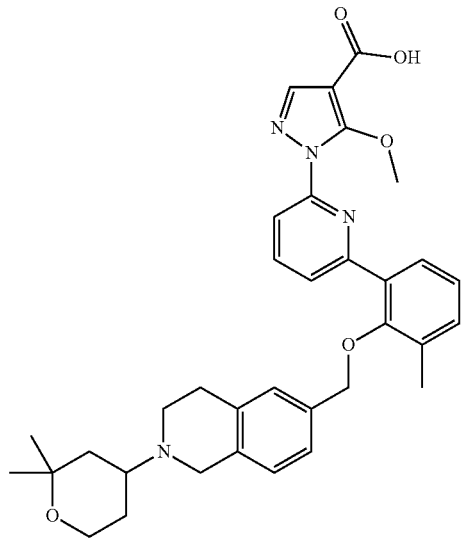 [SMILES: COc1c(C(=O)O)cnn1-c1cccc(-c2cccc(C)c2OCc2ccc3c(c2)CCN(C2CCOC(C)(C)C2)C3)n1] |
| 62 | 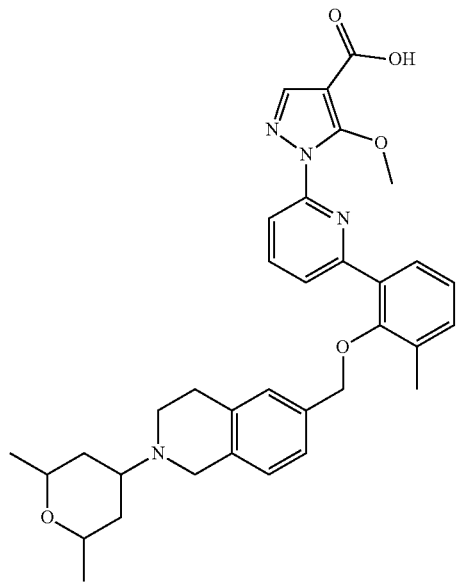 |
| Cpd No. | Structure |
|---|---|
| 63 | 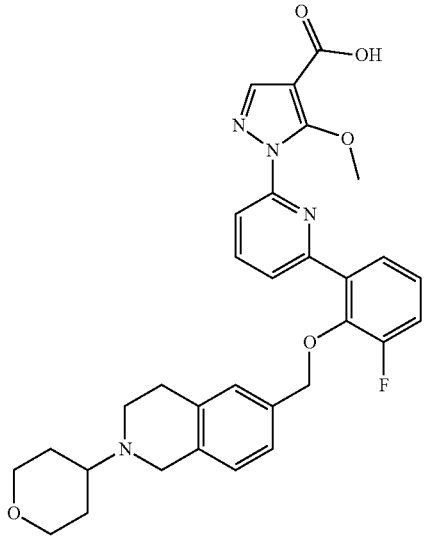 |
| 64 | 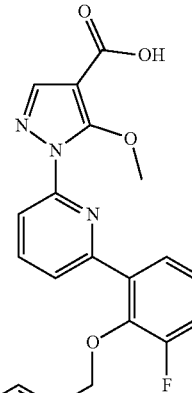 |

| Cpd No. | Structure |
|---|---|
| 65 | |
| 66 | |

| Cpd No. | Structure |
|---|---|
| 67 | 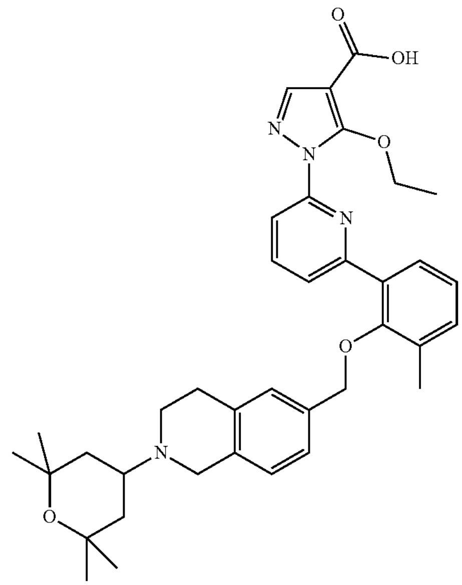 [SMILES: CCOc1c(C(=O)O)cnn1-c1cccc(-c2cccc(C)c2OCc2ccc3c(c2)CCN(C2CC(C)(C)OC(C)(C)C2)C3)n1] |
| 68 | 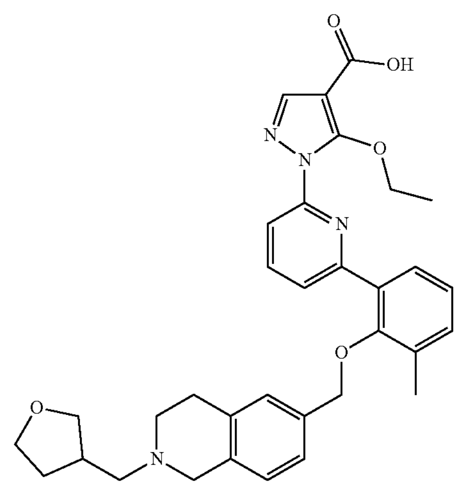 [SMILES: CCOc1c(C(=O)O)cnn1-c1cccc(-c2cccc(C)c2OCc2ccc3c(c2)CCN(CC2CCOC2)C3)n1] |
| 69 | 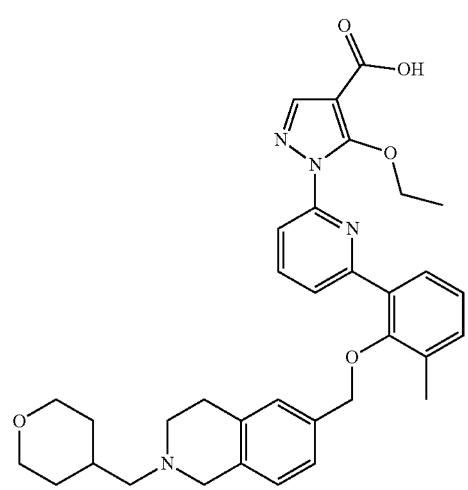 [SMILES: CCOc1c(C(=O)O)cnn1-c1cccc(-c2cccc(C)c2OCc2ccc3c(c2)CCN(CC2CCOCC2)C3)n1] |

| Cpd No. | Structure |
|---|---|
| 70 | 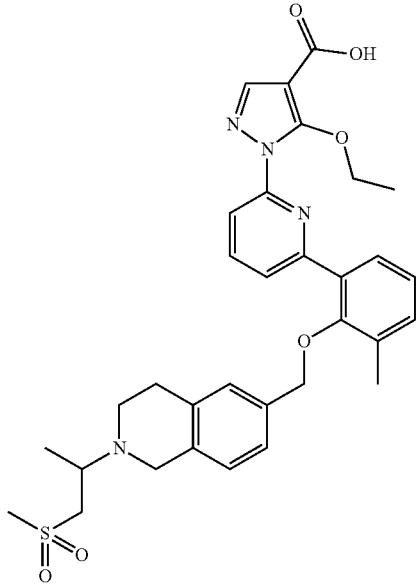 [SMILES: CCOc1c(C(=O)O)cnn1-c1cccc(-c2cccc(C)c2OCc2ccc3c(c2)CCN(C(C)CS(C)(=O)=O)C3)n1] |
| 71 | 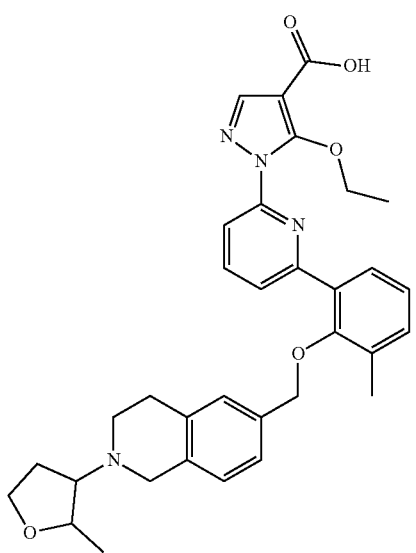 [SMILES: CCOc1c(C(=O)O)cnn1-c1cccc(-c2cccc(C)c2OCc2ccc3c(c2)CCN(C2CCOC2C)C3)n1] |
| Cpd No. | Structure |
|---|---|
| 72 | |
| 73 | 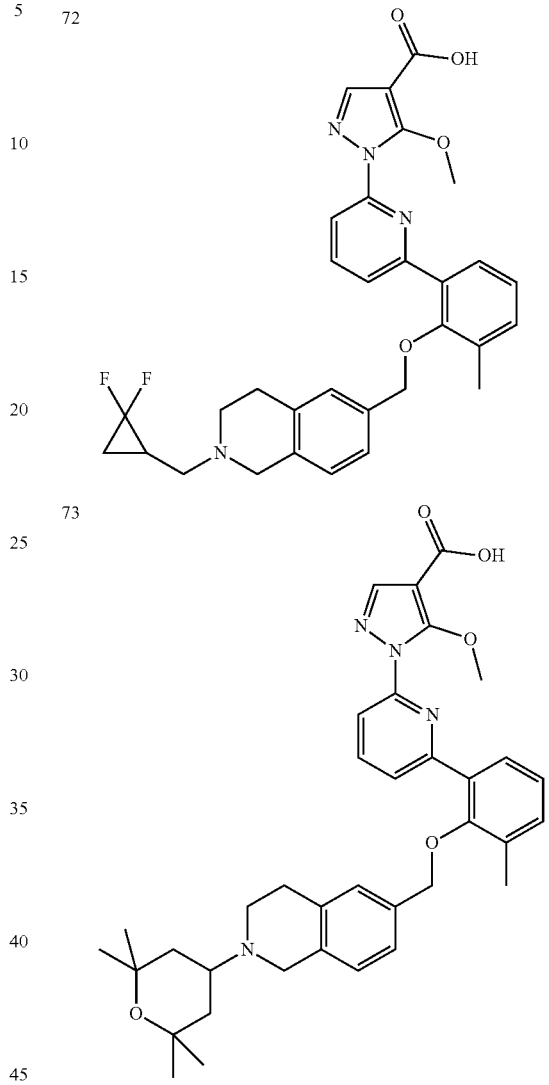 |
| 74 | 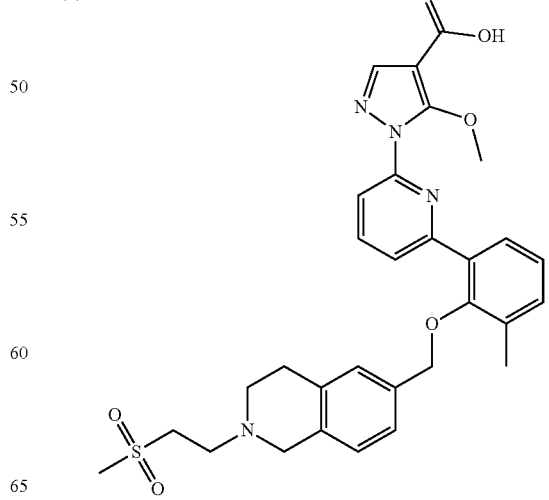 |

-continued
| Cpd No. | Structure |
|---|---|
| 75 | 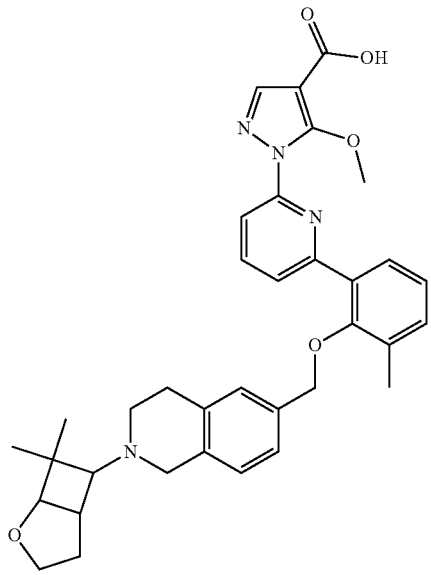 [SMILES: COc1c(C(=O)O)cnn1-c1cccc(-c2cccc(C)c2OCc2ccc3c(c2)CCN(C2C4CCOC4C2(C)C)C3)n1] |
| 76 | 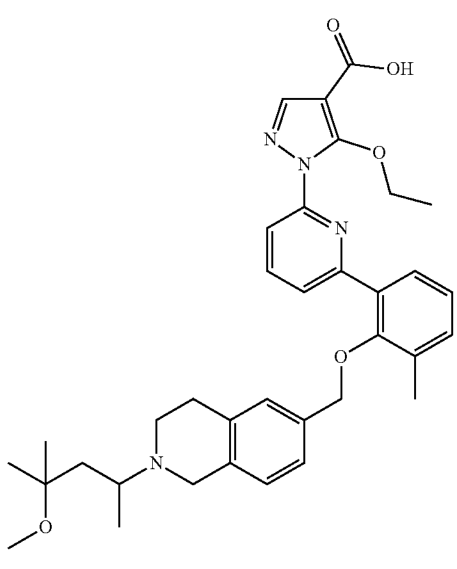 [SMILES: CCOc1c(C(=O)O)cnn1-c1cccc(-c2cccc(C)c2OCc2ccc3c(c2)CCN(C(C)CC(C)(C)OC)C3)n1] |
-continued
| Cpd No. | Structure |
|---|---|
| 77 | 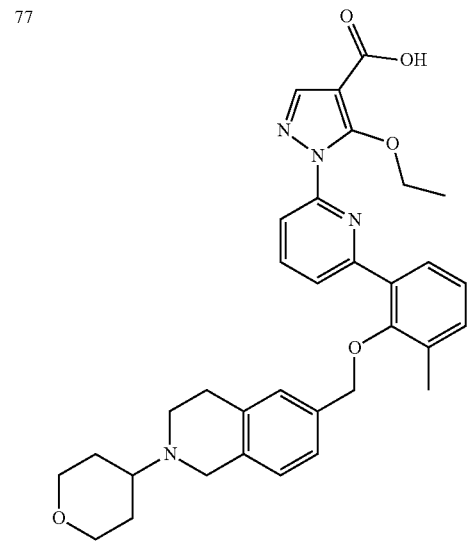 |
| 78 | 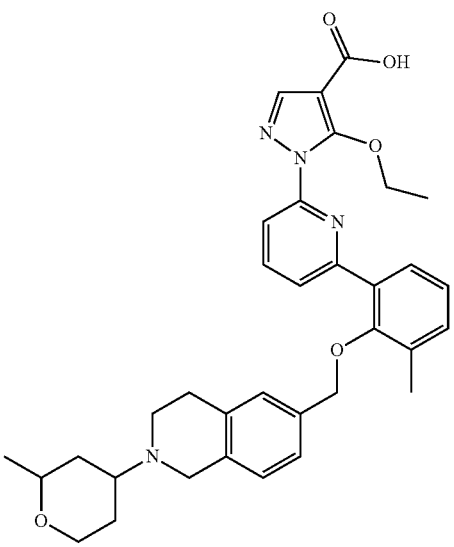 |
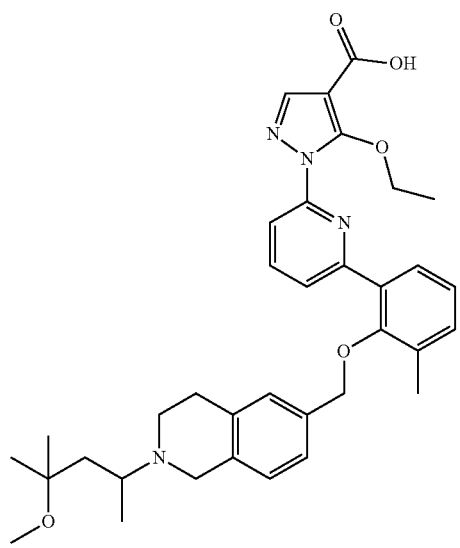

| Cpd No. | Structure |
|---|---|
| 79 | 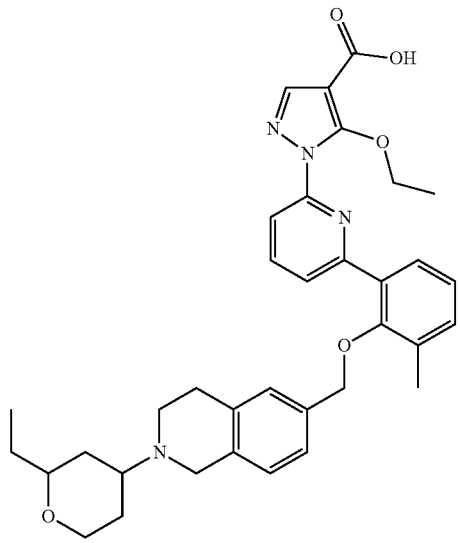 [SMILES: CCOc1c(C(=O)O)cnn1-c1cccc(-c2cccc(C)c2OCc2ccc3c(c2)CCN(C2CCOC(CC)C2)C3)n1] |
| 80 | 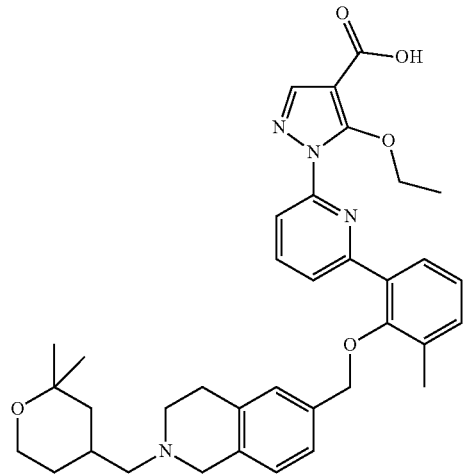 [SMILES: CCOc1c(C(=O)O)cnn1-c1cccc(-c2cccc(C)c2OCc2ccc3c(c2)CCN(CC2CCOC(C)(C)C2)C3)n1] |
| 81 | 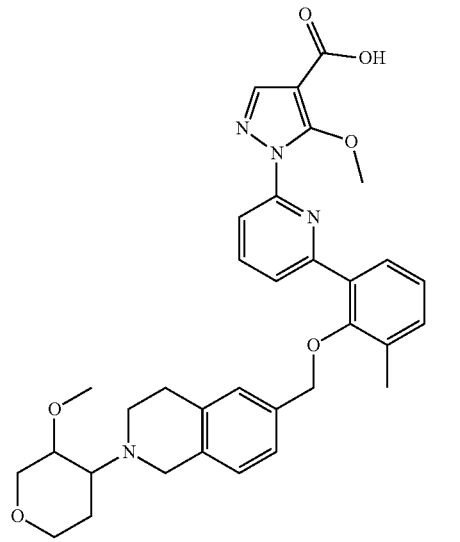 [SMILES: COc1c(C(=O)O)cnn1-c1cccc(-c2cccc(C)c2OCc2ccc3c(c2)CCN(C2CCOCC2OC)C3)n1] |
| Cpd No. | Structure |
|---|---|
| 82 | 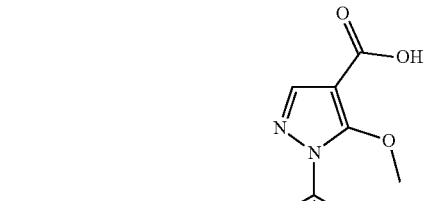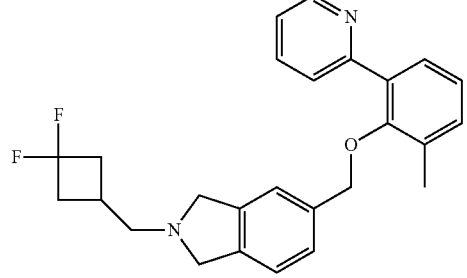 |
| 83 | 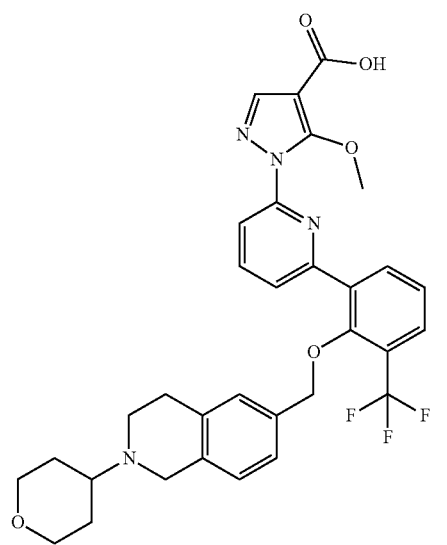 [SMILES: COc1c(C(=O)O)cnn1-c1cccc(-c2cccc(C(F)(F)F)c2OCc2ccc3c(c2)CCN(C2CCOCC2)C3)n1] |
| 84 | 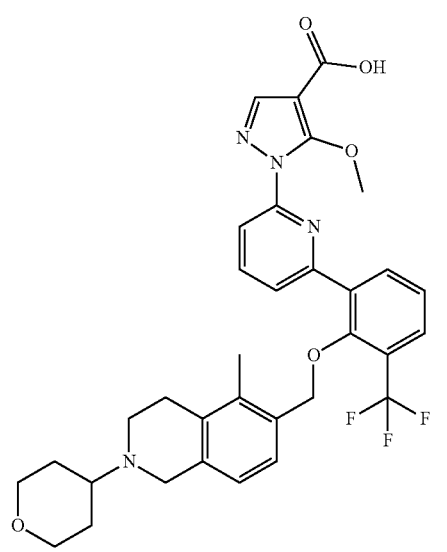 [SMILES: COc1c(C(=O)O)cnn1-c1cccc(-c2cccc(C(F)(F)F)c2OCc2ccc3c(c2C)CCN(C2CCOCC2)C3)n1] |

| Cpd No. | Structure |
|---|---|
| 85 | 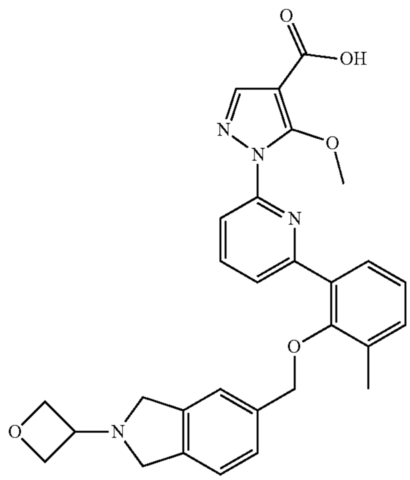 [SMILES: COc1c(C(=O)O)cnn1-c1cccc(-c2cccc(C)c2OCc2ccc3c(c2)CN(C2COC2)C3)n1] |
| 86 | 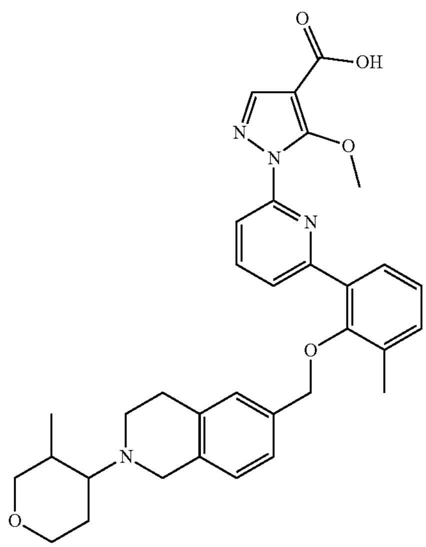 |
| 87 | 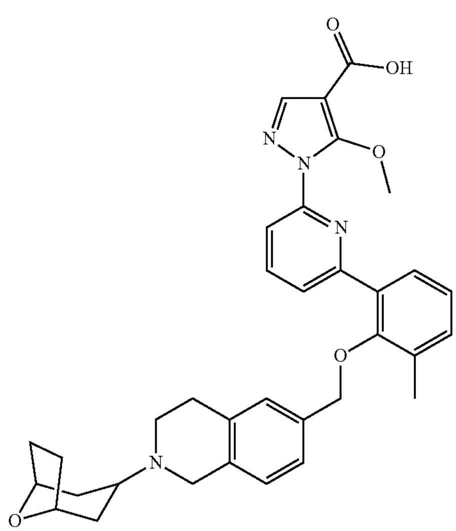 [SMILES: COc1c(C(=O)O)cnn1-c1cccc(-c2cccc(C)c2OCc2ccc3c(c2)CCN(C2CC4CCC(C2)O4)C3)n1] |
| 88 | |
| 89 | |
| 90 | |

| Cpd No. | Structure |
|---|---|
| 91 | 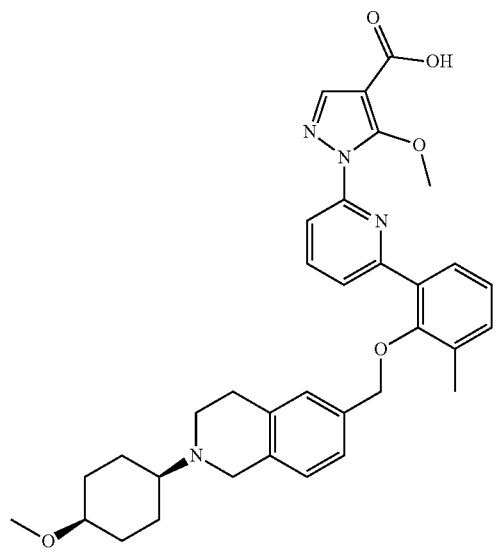 [SMILES: COc1c(C(=O)O)cnn1-c1cccc(-c2cccc(C)c2OCc2ccc3c(c2)CCN([C@H]2CC[C@@H](OC)CC2)C3)n1] |
| 92 | 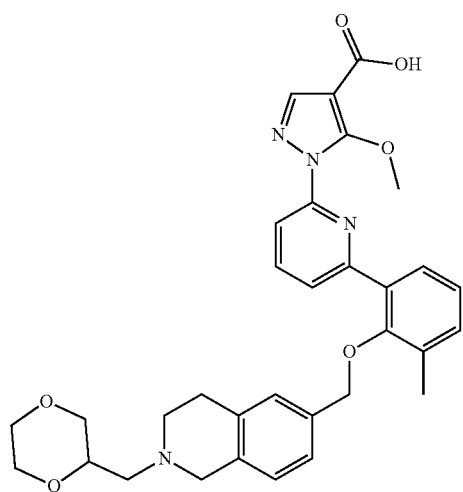 [SMILES: COc1c(C(=O)O)cnn1-c1cccc(-c2cccc(C)c2OCc2ccc3c(c2)CCN(CC2COCCO2)C3)n1] |
| 93 | 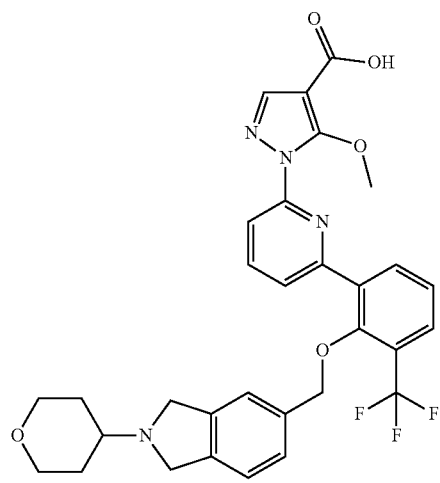 [SMILES: COc1c(C(=O)O)cnn1-c1cccc(-c2cccc(C(F)(F)F)c2OCc2ccc3c(c2)CN(C2CCOCC2)C3)n1] |
| 94 | 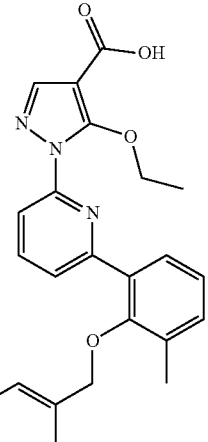 |
| 95 | 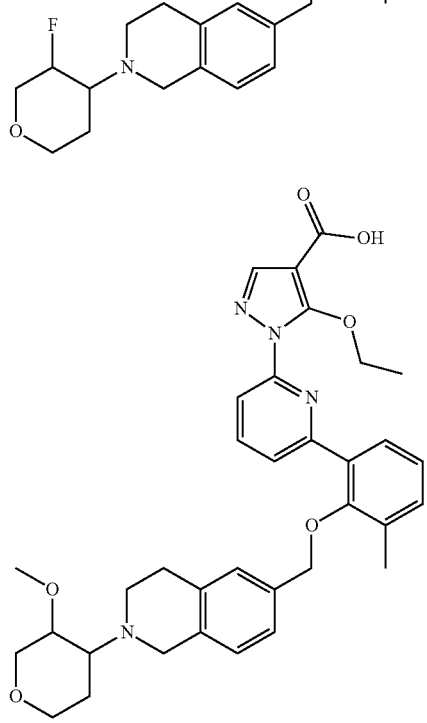 |
| 96 | 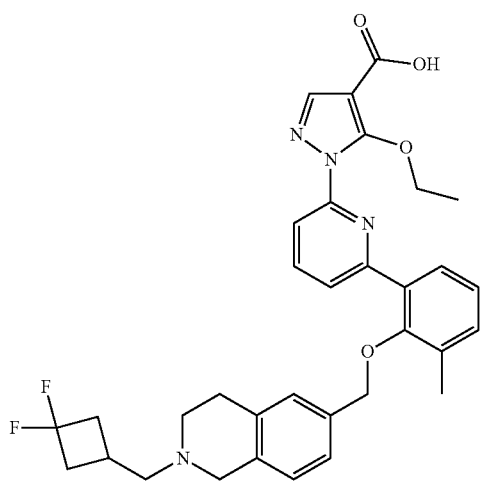 [SMILES: CCOc1c(C(=O)O)cnn1-c1cccc(-c2cccc(C)c2OCc2ccc3c(c2)CCN(CC2CC(F)(F)C2)C3)n1] |

-continued
| Cpd No. | Structure |
|---|---|
| 97 | 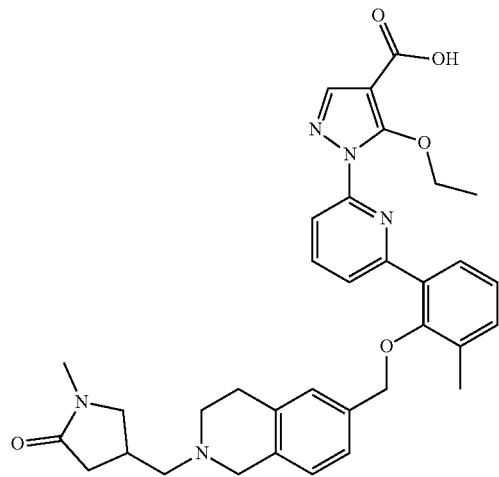 [SMILES: CCOc1c(C(=O)O)cnn1-c1cccc(-c2cccc(C)c2OCc2ccc3c(c2)CCN(CC2CC(=O)N(C)C2)C3)n1] |
| 98 | 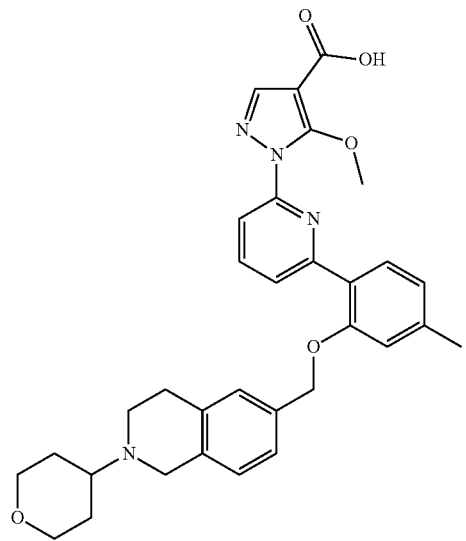 [SMILES: COc1c(C(=O)O)cnn1-c1cccc(-c2ccc(C)cc2OCc2ccc3c(c2)CCN(C2CCOCC2)C3)n1] |
| 99 | 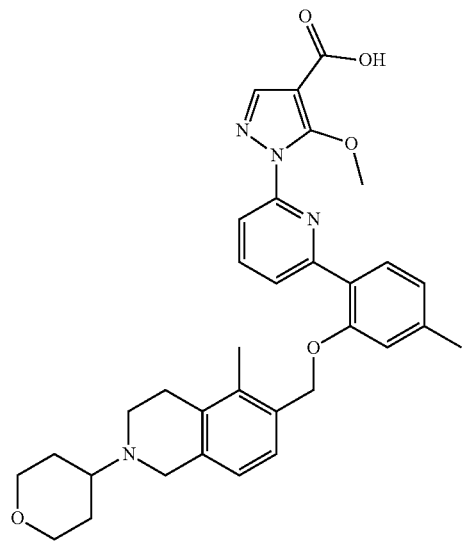 [SMILES: COc1c(C(=O)O)cnn1-c1cccc(-c2ccc(C)cc2OCc2ccc3c(c2C)CCN(C2CCOCC2)C3)n1] |
-continued
| Cpd No. | Structure |
|---|---|
| 100 | 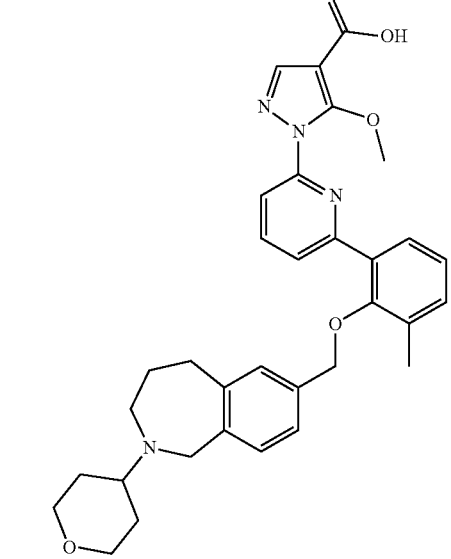 |
| 101 | 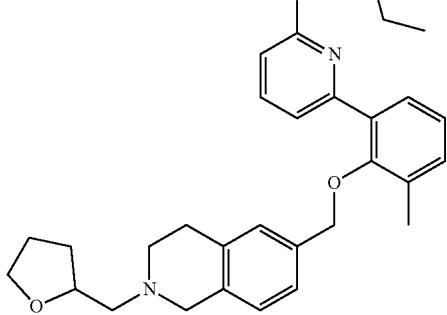 |

-continued
| Cpd No. | Structure |
|---|---|
| 102 | 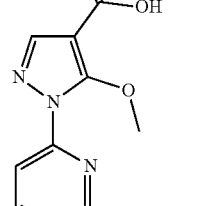 |
| 103 |  |
-continued
| Cpd No. | Structure |
|---|---|
| 104 | 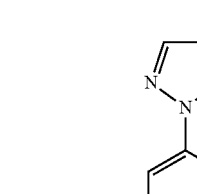 |
| 105 | 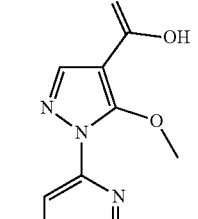 |

| Cpd No. | Structure |
|---|---|
| 106 |  |
| 107 | |
| 108 | |
| Cpd No. | Structure |
|---|---|
| 109 |  |
| 110 | |

-continued
| Cpd No. | Structure |
|---|---|
| 111 | 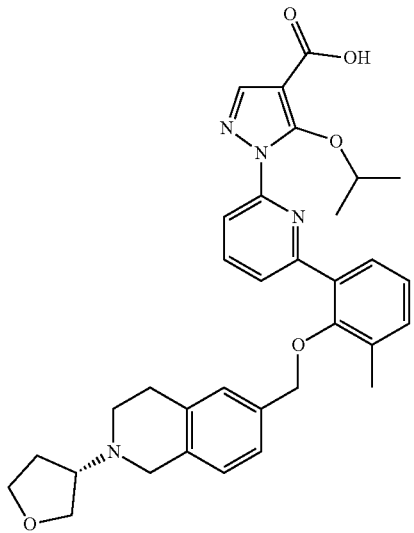 [SMILES: Cc1cccc(-c2cccc(-n3ncc(C(=O)O)c3OC(C)C)n2)c1OCc1ccc2c(c1)CCN([C@H]1CCOC1)C2] |
| 112 | 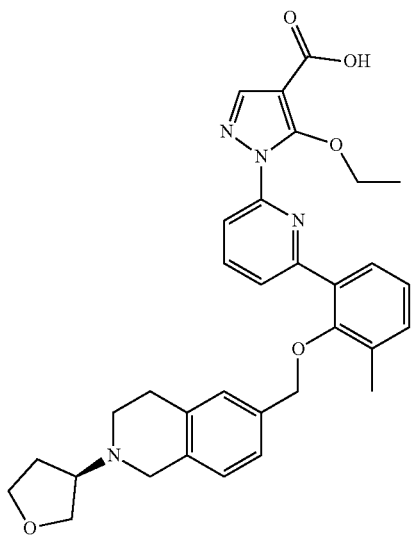 [SMILES: CCOc1c(C(=O)O)cnn1-c1cccc(-c2cccc(C)c2OCc2ccc3c(c2)CCN([C@@H]2CCOC2)C3)n1] |
| 113 | 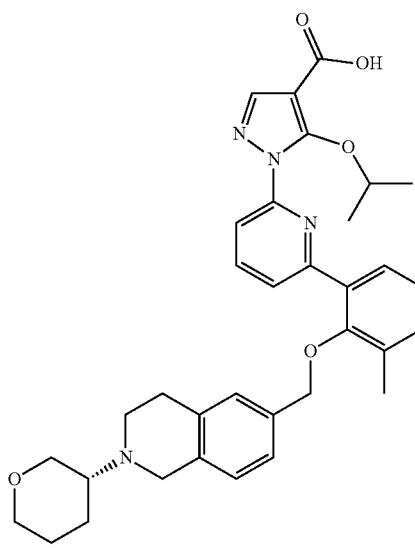 |
-continued
| Cpd No. | Structure |
|---|---|
| 114 | 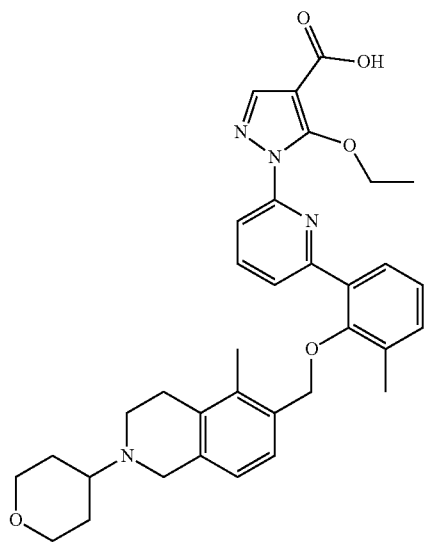 |
| 115 | 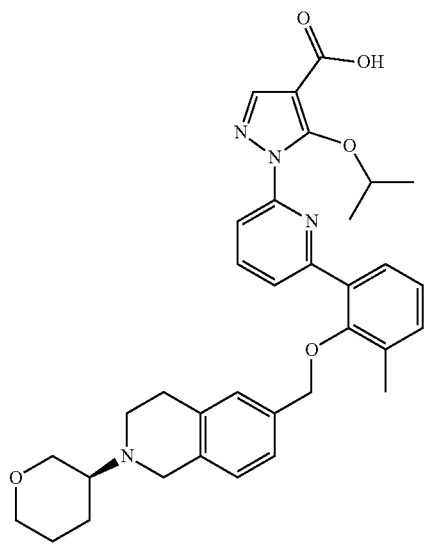 |

| Cpd No. | Structure |
|---|---|
| 116 | 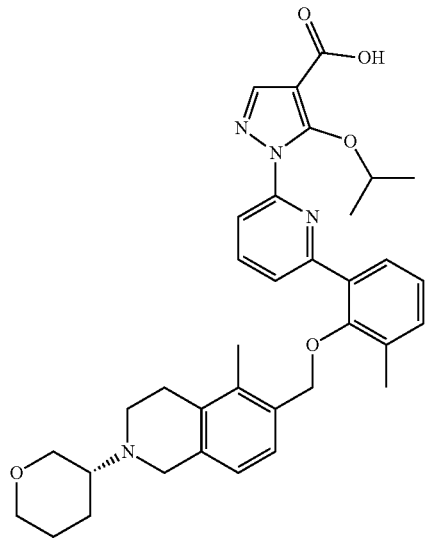 [SMILES: Cc1cccc(-c2cccc(-n3ncc(C(=O)O)c3OC(C)C)n2)c1OCc1ccc2c(c1C)CCN([C@@H]1CCCOC1)C2] |
| 117 | 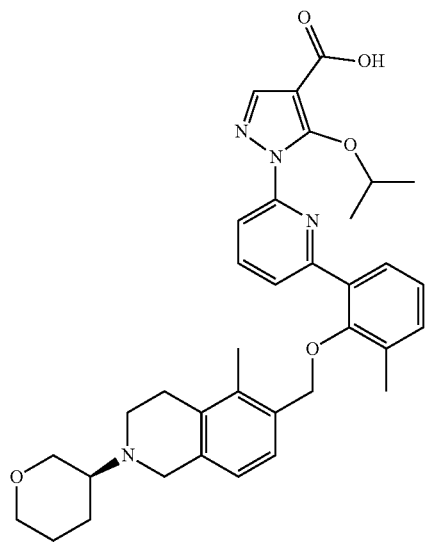 [SMILES: Cc1cccc(-c2cccc(-n3ncc(C(=O)O)c3OC(C)C)n2)c1OCc1ccc2c(c1C)CCN([C@H]1CCCOC1)C2] |
| 118 | 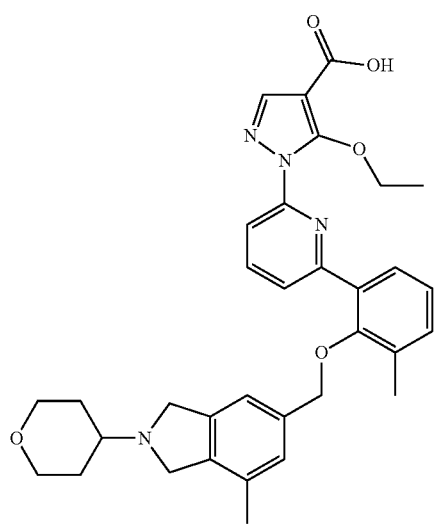 [SMILES: CCOc1c(C(=O)O)cnn1-c1cccc(-c2cccc(C)c2OCc2cc(C)c3c(c2)CN(C2CCOCC2)C3)n1] |
| 119 | 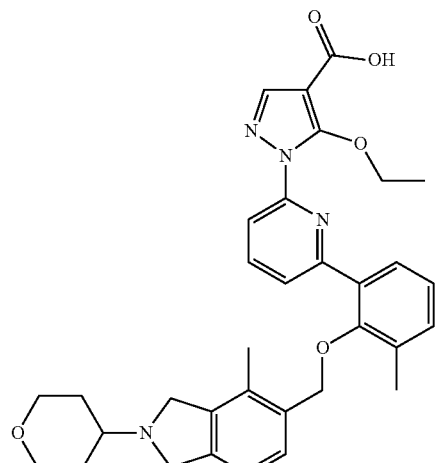 |
| 120 | 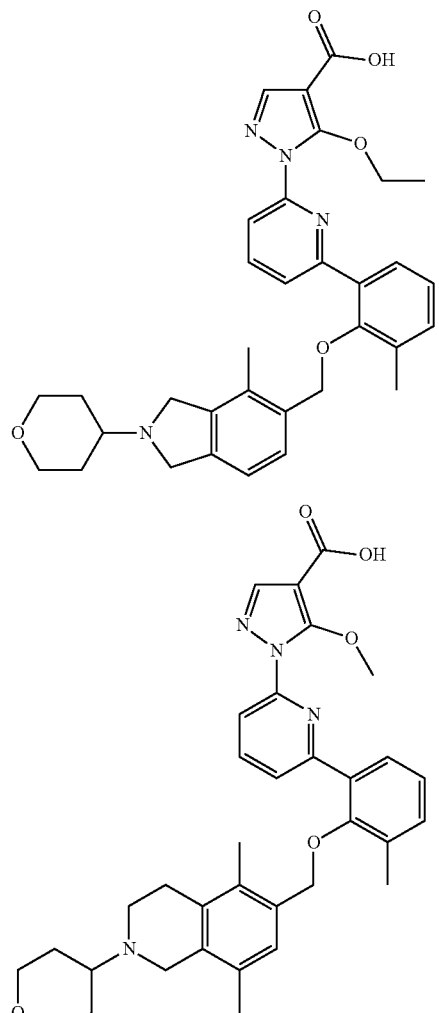 |
| 121 | 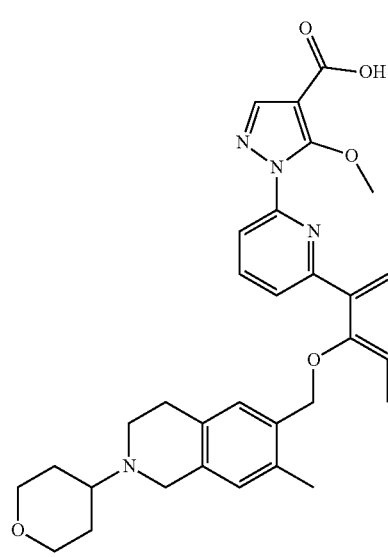 |

| Cpd No. | Structure |
|---|---|
| 122 | 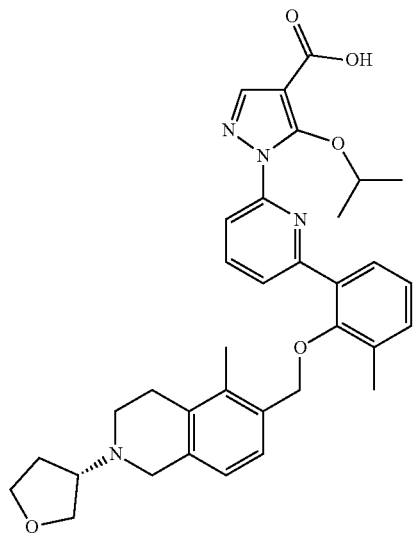 [SMILES: Cc1cccc(-c2cccc(-n3ncc(C(=O)O)c3OC(C)C)n2)c1OCc1ccc2c(c1C)CCN([C@H]1CCOC1)C2] |
| 123 | 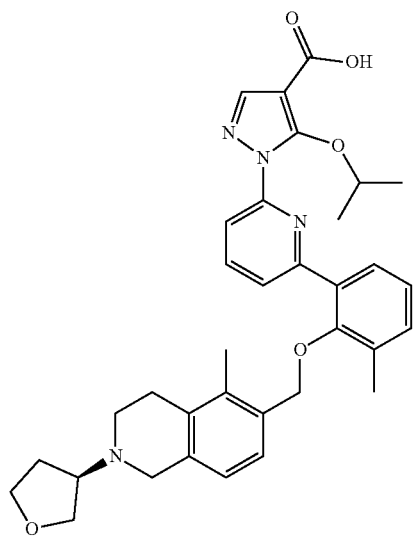 [SMILES: Cc1cccc(-c2cccc(-n3ncc(C(=O)O)c3OC(C)C)n2)c1OCc1ccc2c(c1C)CCN([C@@H]1CCOC1)C2] |
| Cpd No. | Structure |
|---|---|
| 124 | 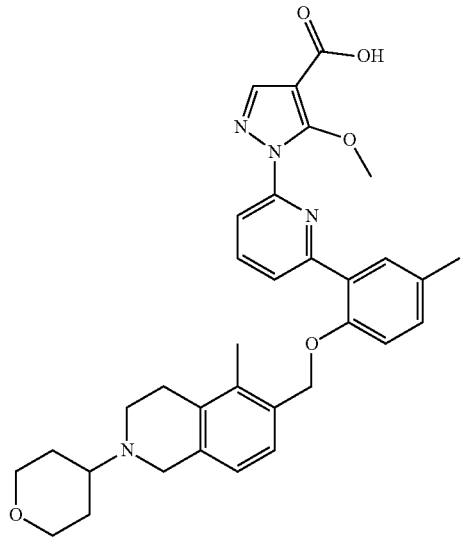 [SMILES: COc1c(C(=O)O)cnn1-c1cccc(-c2cc(C)ccc2OCc2ccc3c(c2C)CCN(C2CCOCC2)C3)n1] |
| 125 | 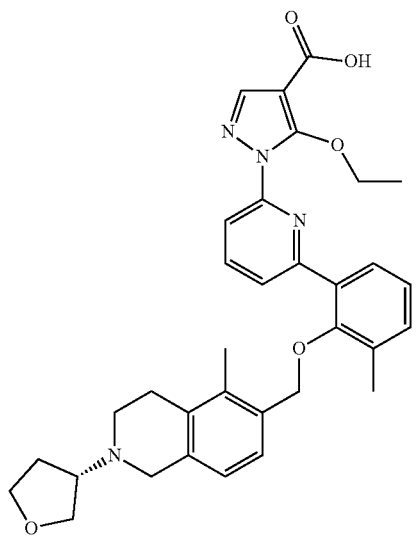 [SMILES: CCOc1c(C(=O)O)cnn1-c1cccc(-c2cccc(C)c2OCc2ccc3c(c2C)CCN([C@H]2CCOC2)C3)n1] |

| Cpd No. | Structure |
|---|---|
| 126 | 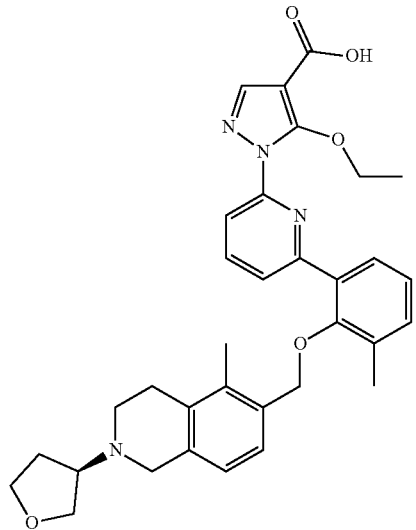 [SMILES: CCOc1c(C(=O)O)cnn1-c1cccc(-c2cccc(C)c2OCc2ccc3c(c2C)CCN([C@@H]2CCOC2)C3)n1] |
| 127 | 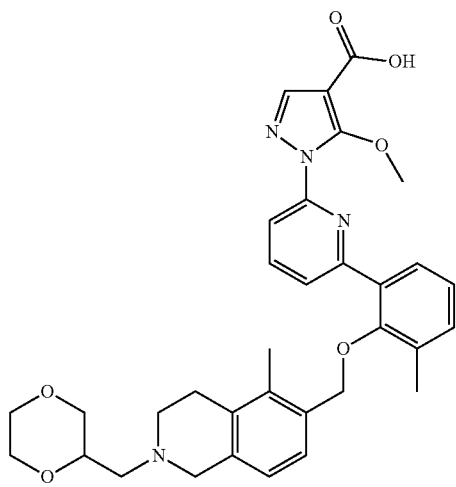 [SMILES: COc1c(C(=O)O)cnn1-c1cccc(-c2cccc(C)c2OCc2ccc3c(c2C)CCN(CC2COCCO2)C3)n1] |
| 128 | 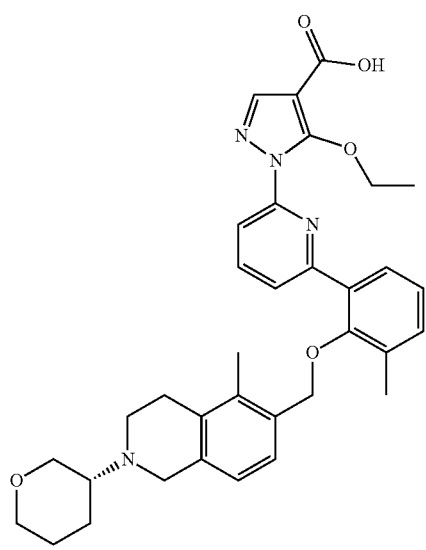 [SMILES: CCOc1c(C(=O)O)cnn1-c1cccc(-c2cccc(C)c2OCc2ccc3c(c2C)CCN([C@@H]2CCCOC2)C3)n1] |
| 129 | 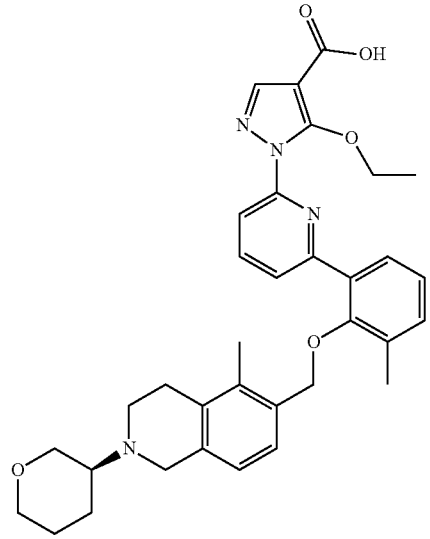 |
| 130 | 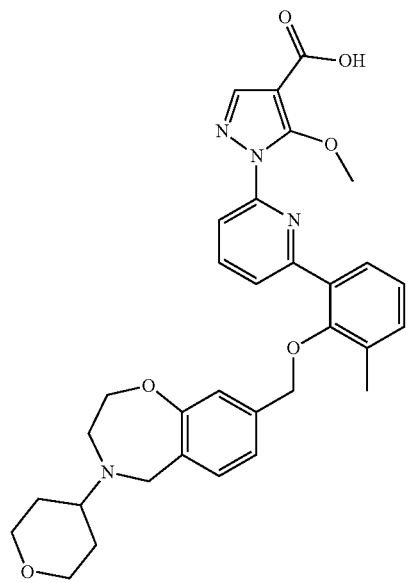 [SMILES: COc1c(C(=O)O)cnn1-c1cccc(-c2cccc(C)c2OCc2ccc3c(c2)OCCN(C2CCOCC2)C3)n1] |

-continued
| Cpd No. | Structure |
|---|---|
| 131 | 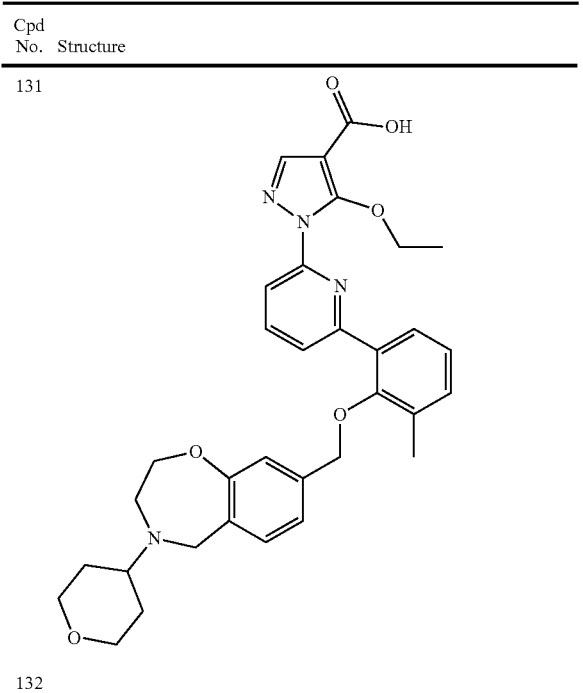 |
| 132 | 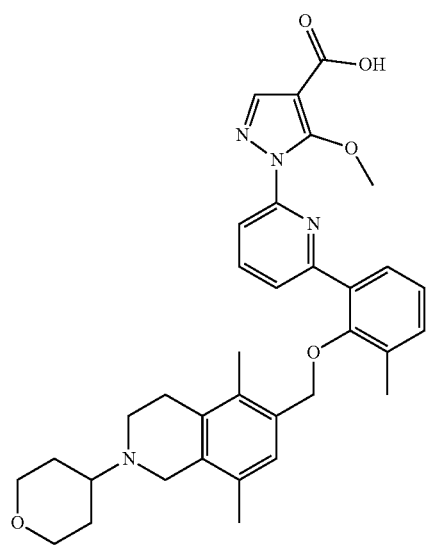 [SMILES: COc1c(C(=O)O)cnn1-c1cccc(-c2cccc(C)c2OCc2cc(C)c3c(c2C)CCN(C2CCOCC2)C3)n1] |
-continued
| Cpd No. | Structure |
|---|---|
| 133 | 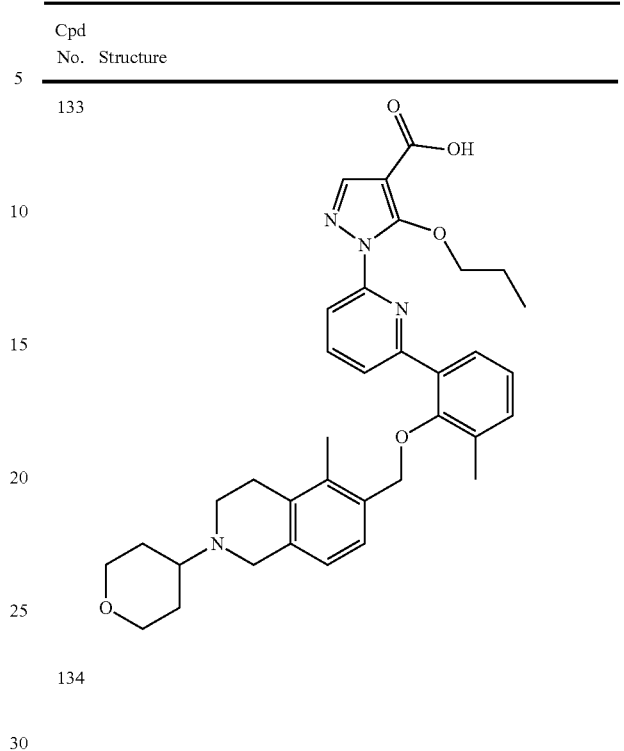 |
| 134 | 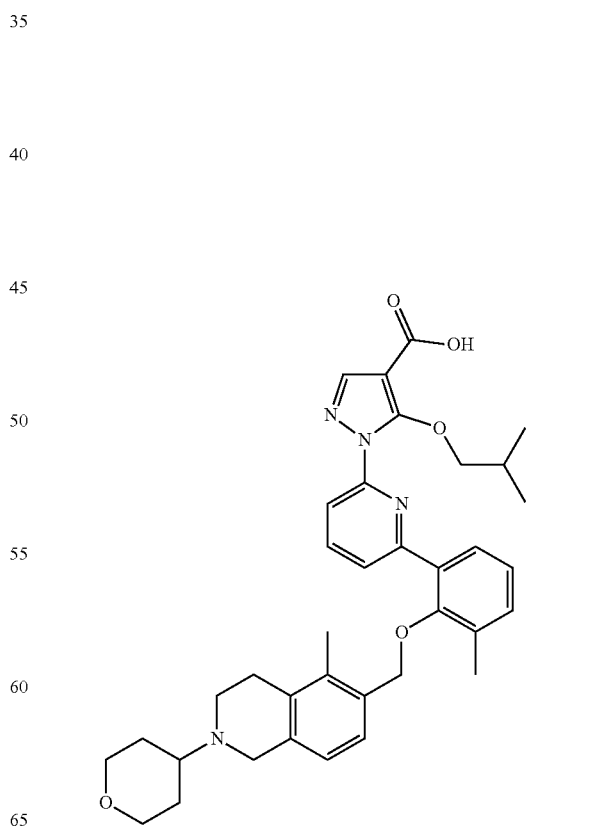 |

| Cpd No. | Structure |
|---|---|
| 135 | 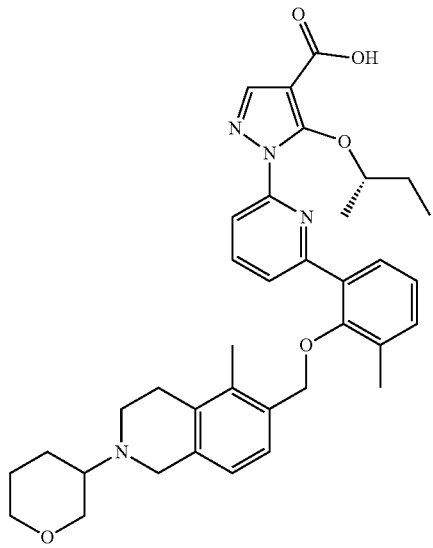 [SMILES: CC[C@H](C)Oc1c(C(=O)O)cnn1-c1cccc(-c2cccc(C)c2OCc2ccc3c(c2C)CCN(C2CCCOC2)C3)n1] |
| 136 | 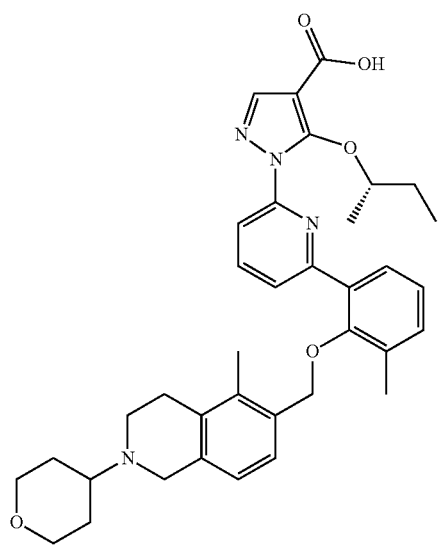 [SMILES: CC[C@H](C)Oc1c(C(=O)O)cnn1-c1cccc(-c2cccc(C)c2OCc2ccc3c(c2C)CCN(C2CCOCC2)C3)n1] |
| Cpd No. | Structure |
|---|---|
| 137 | 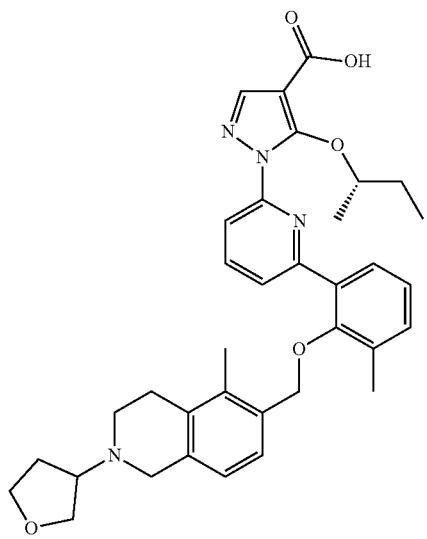 [SMILES: CC[C@H](C)Oc1c(C(=O)O)cnn1-c1cccc(-c2cccc(C)c2OCc2ccc3c(c2C)CCN(C2CCOC2)C3)n1] |
| 138 | 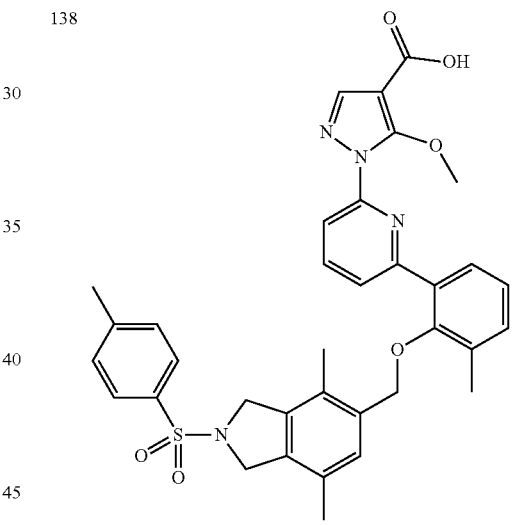 |
| 139 | 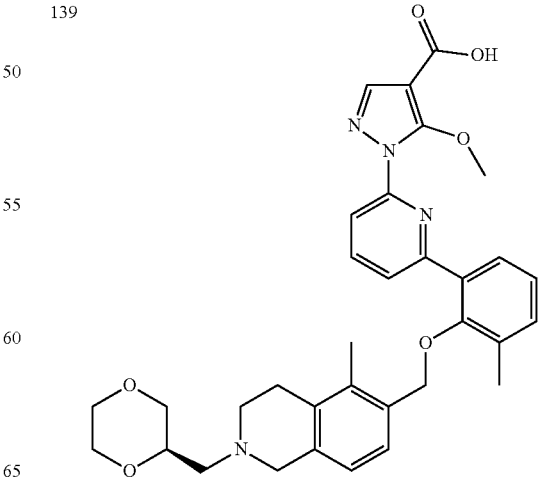 |

| Cpd No. | Structure |
|---|---|
| 140 | 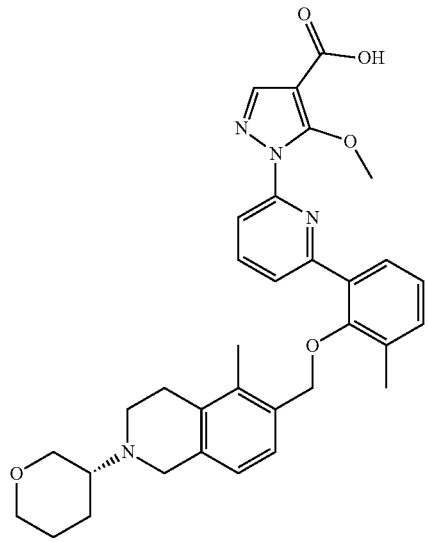 [SMILES: COc1c(C(=O)O)cnn1-c1cccc(-c2cccc(C)c2OCc2ccc3c(c2C)CCN([C@@H]2CCCOC2)C3)n1] |
| 141 | 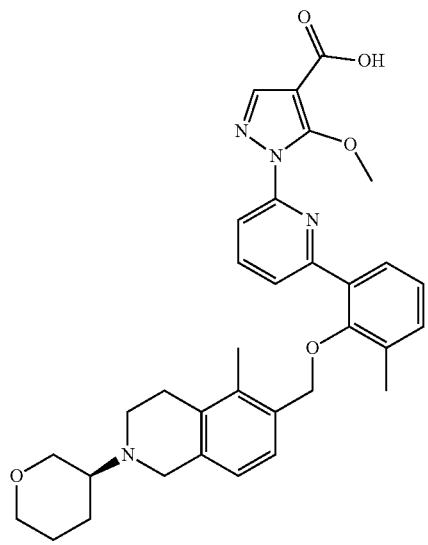 [SMILES: COc1c(C(=O)O)cnn1-c1cccc(-c2cccc(C)c2OCc2ccc3c(c2C)CCN([C@H]2CCCOC2)C3)n1] |
| 142 | 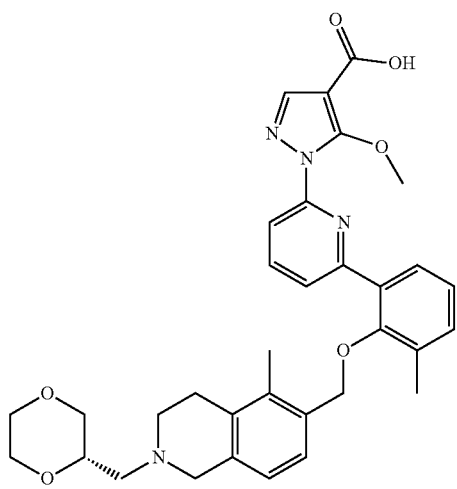 [SMILES: COc1c(C(=O)O)cnn1-c1cccc(-c2cccc(C)c2OCc2ccc3c(c2C)CCN(C[C@H]2COCCO2)C3)n1] |
| 143 | 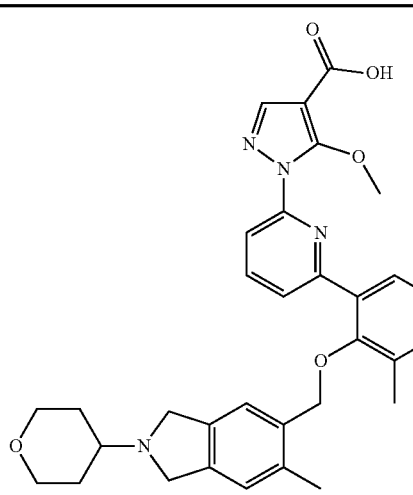 |
| 144 | 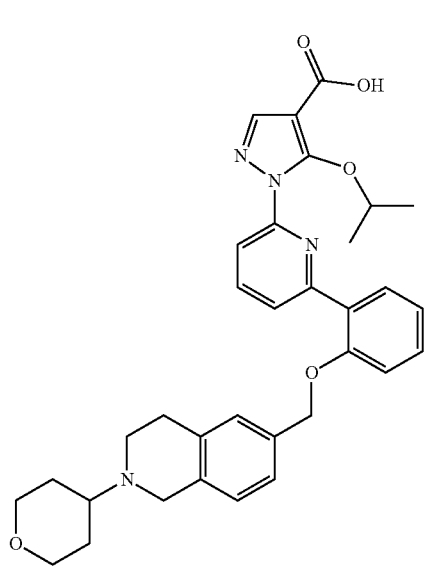 [SMILES: CC(C)Oc1c(C(=O)O)cnn1-c1cccc(-c2ccccc2OCc2ccc3c(c2)CCN(C2CCOCC2)C3)n1] |
| 145 | 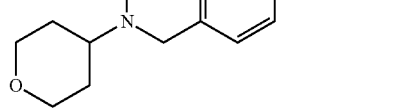 |

| Cpd No. | Structure |
|---|---|
| 146 | 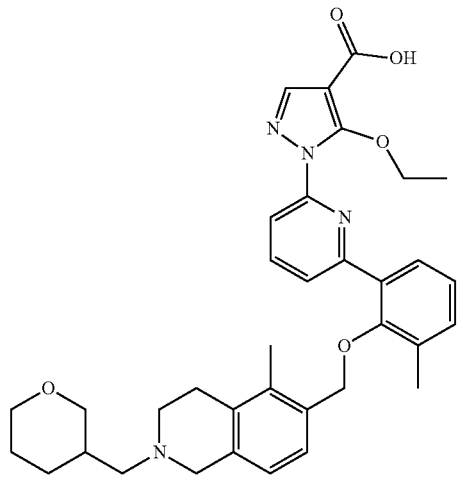 [SMILES: CCOc1c(C(=O)O)cnn1-c1cccc(-c2cccc(C)c2OCc2ccc3c(c2C)CCN(CC2CCCOC2)C3)n1] |
| 147 | 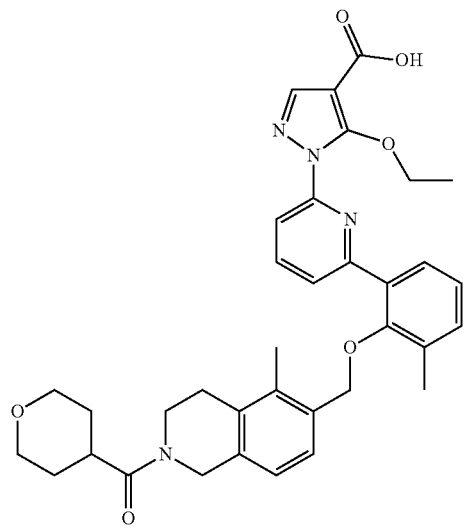 [SMILES: CCOc1c(C(=O)O)cnn1-c1cccc(-c2cccc(C)c2OCc2ccc3c(c2C)CCN(C(=O)C2CCOCC2)C3)n1] |
| 148 | 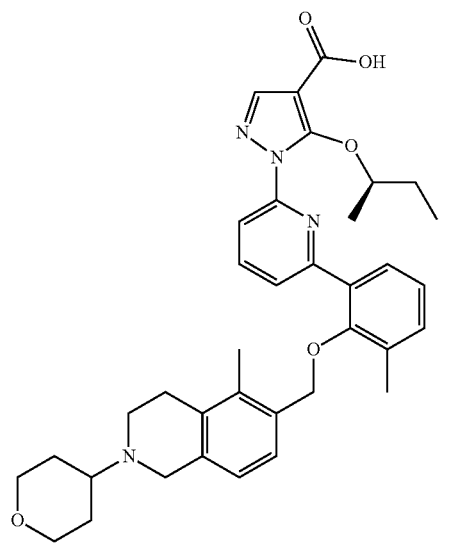 |
| Cpd No. | Structure |
|---|---|
| 149 | 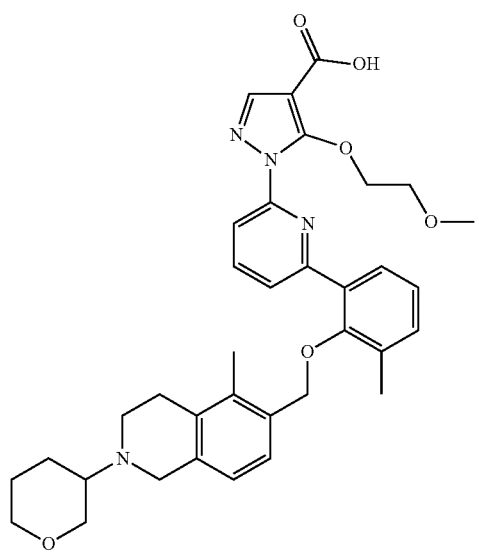 [SMILES: COCCOc1c(C(=O)O)cnn1-c1cccc(-c2cccc(C)c2OCc2ccc3c(c2C)CCN(C2CCCOC2)C3)n1] |
| 150 | 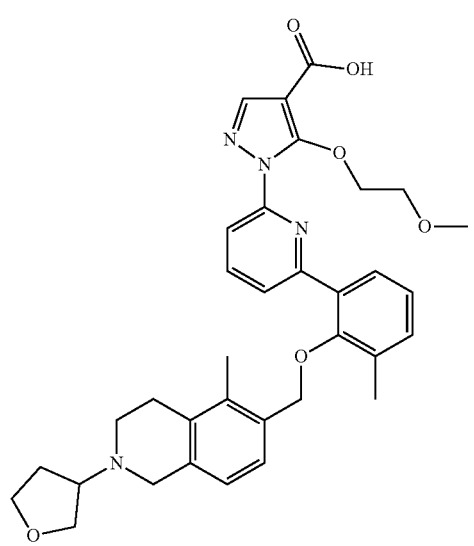 [SMILES: COCCOc1c(C(=O)O)cnn1-c1cccc(-c2cccc(C)c2OCc2ccc3c(c2C)CCN(C2CCOC2)C3)n1] |

-continued
| Cpd No. | Structure |
|---|---|
| 151 | 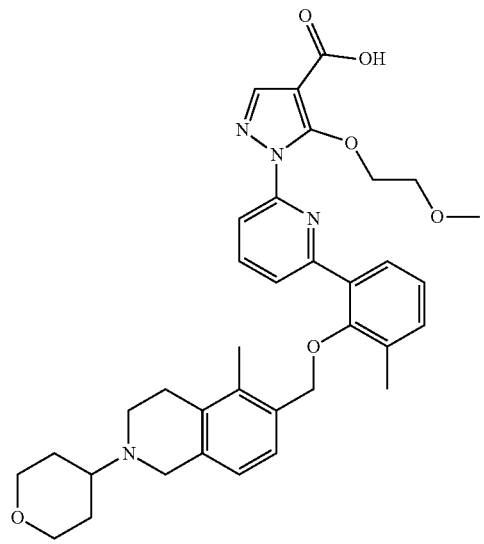 [SMILES: COCCOc1c(C(=O)O)cnn1-c1cccc(-c2cccc(C)c2OCc2ccc3c(c2C)CCN(C2CCOCC2)C3)n1] |
| 152 | 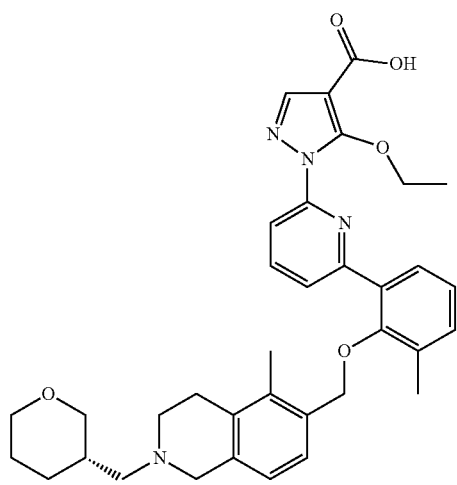 |
| 153 | 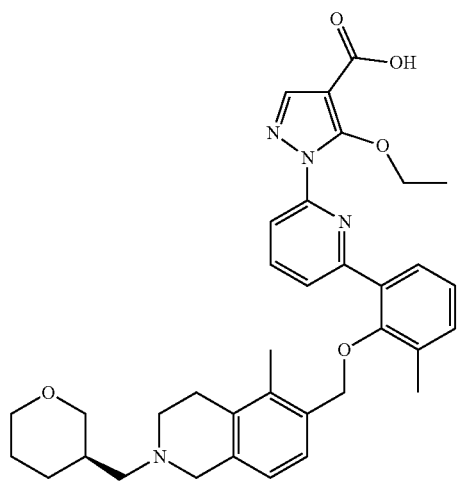 [SMILES: CCOc1c(C(=O)O)cnn1-c1cccc(-c2cccc(C)c2OCc2ccc3c(c2C)CCN(C[C@H]2CCCOC2)C3)n1] |
-continued
| Cpd No. | Structure |
|---|---|
| 154 | 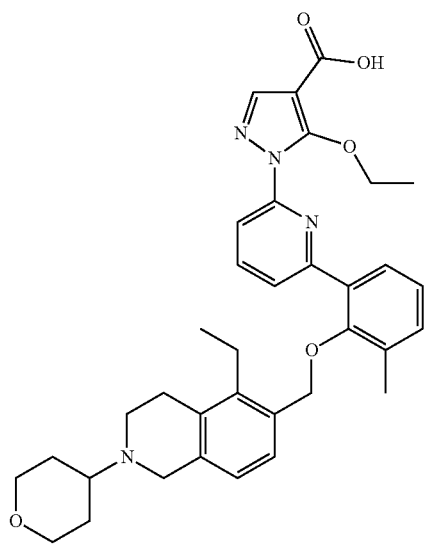 |
| 155 | 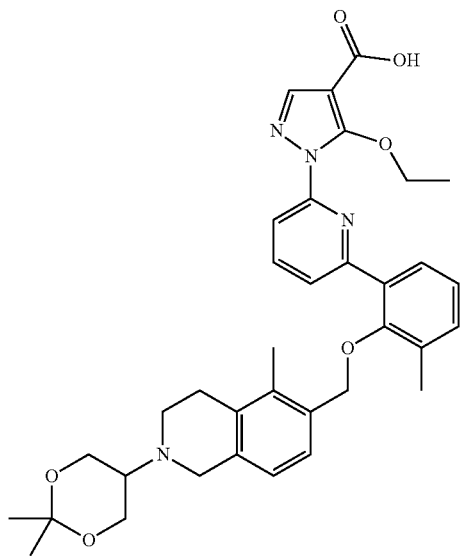 [SMILES: CCOc1c(C(=O)O)cnn1-c1cccc(-c2cccc(C)c2OCc2ccc3c(c2C)CCN(C2COC(C)(C)OC2)C3)n1] |

| Cpd No. | Structure |
|---|---|
| 156 | 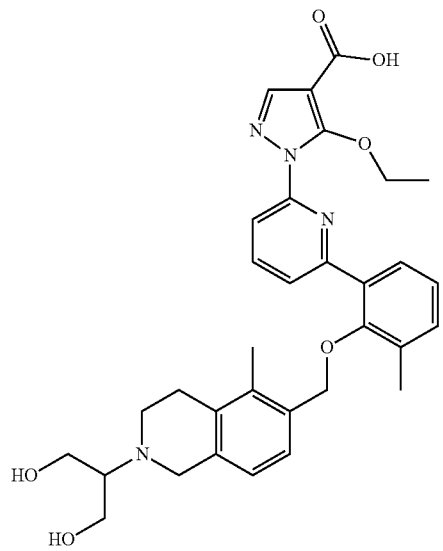 [SMILES: CCOc1c(C(=O)O)cnn1-c1cccc(-c2cccc(C)c2OCc2ccc3c(c2C)CCN(C(CO)CO)C3)n1] |
| 157 | 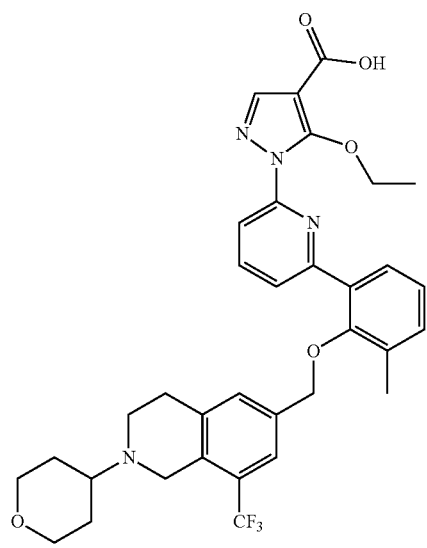 [SMILES: CCOc1c(C(=O)O)cnn1-c1cccc(-c2cccc(C)c2OCc2cc3c(c(C(F)(F)F)c2)CN(C2CCOCC2)CC3)n1] |
| Cpd No. | Structure |
|---|---|
| 158 | 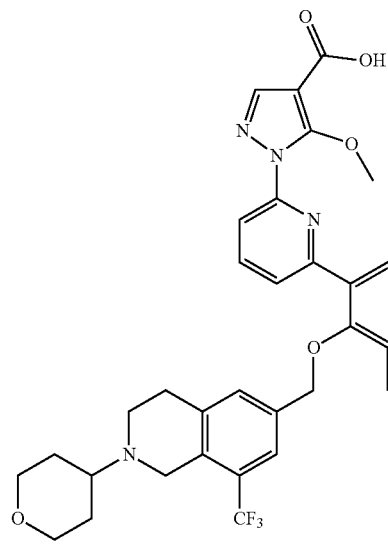 |
| 159 | 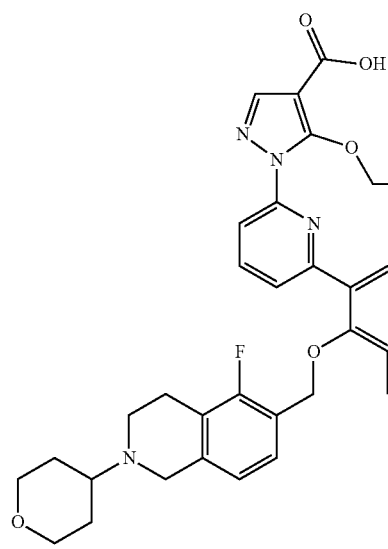 |
| 160 | 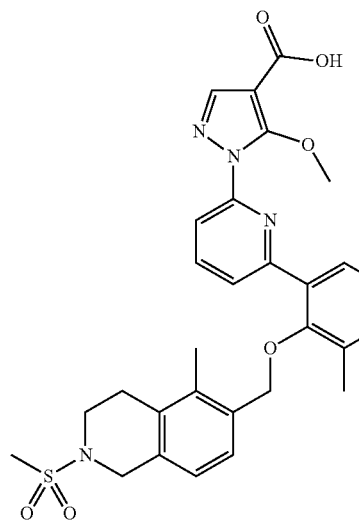 |

173
-continued
| Cpd No. | Structure |
|---|---|
| 161 | 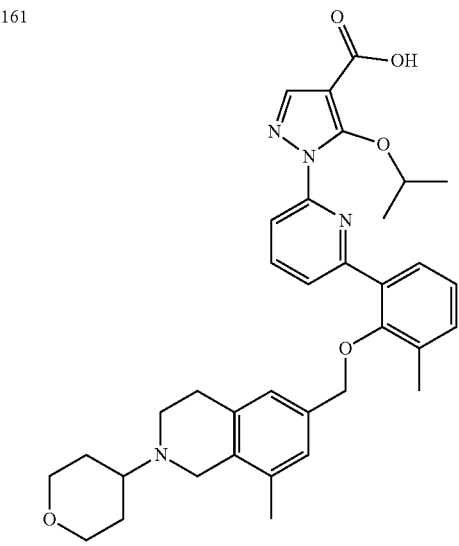 |
| 162 | 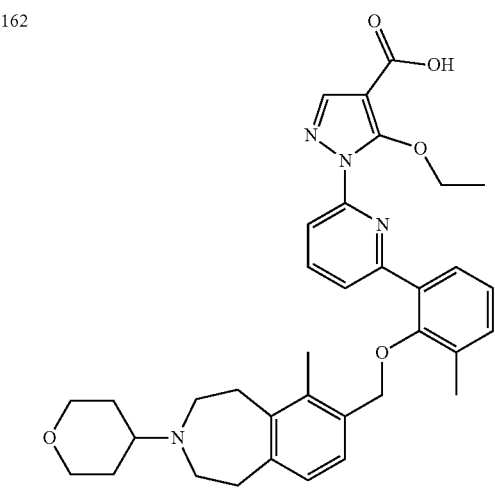 |
| 163 | 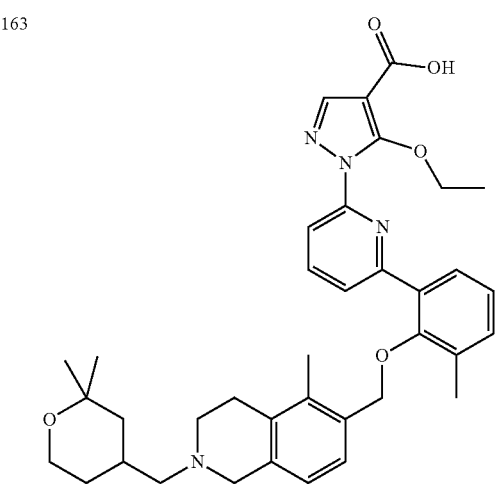 |
174
-continued
| Cpd No. | Structure |
|---|---|
| 164 | 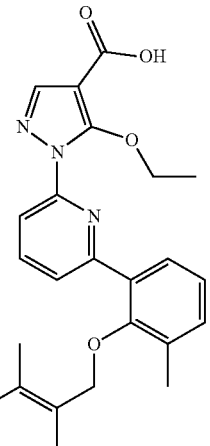 |
| 165 | 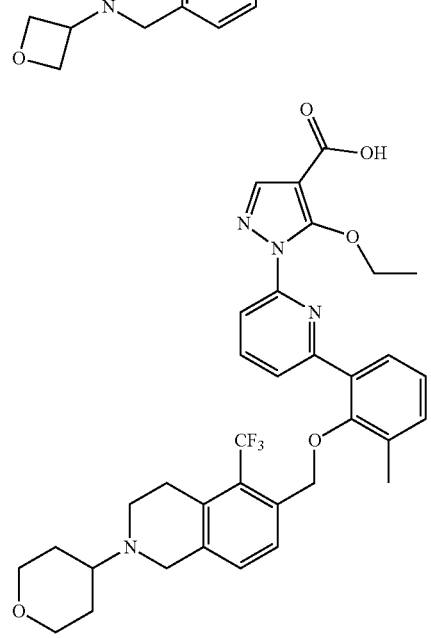 |
| 166 | 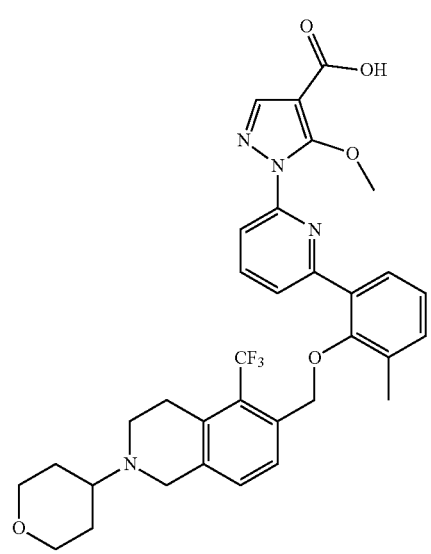 [SMILES: COc1c(C(=O)O)cnn1-c1cccc(-c2cccc(C)c2OCc2ccc3c(c2C(F)(F)F)CCN(C2CCOCC2)C3)n1] |

| Cpd No. | Structure |
|---|---|
| 167 | 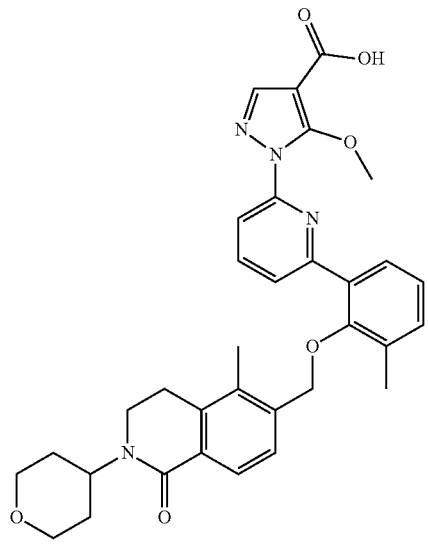 [SMILES: COc1c(C(=O)O)cnn1-c1cccc(-c2cccc(C)c2OCc2ccc3c(c2C)CCN(C2CCOCC2)C3=O)n1] |
| 168 | 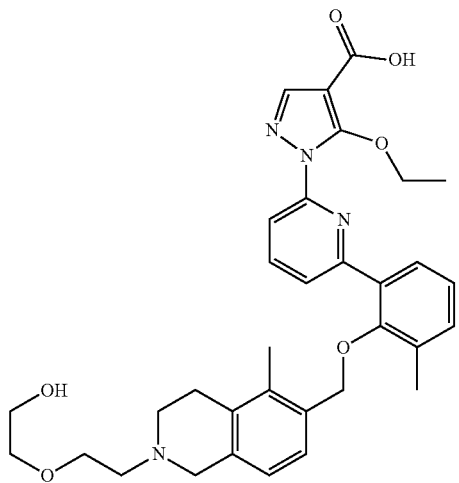 [SMILES: CCOc1c(C(=O)O)cnn1-c1cccc(-c2cccc(C)c2OCc2ccc3c(c2C)CCN(CCOCCO)C3)n1] |
| 169 | 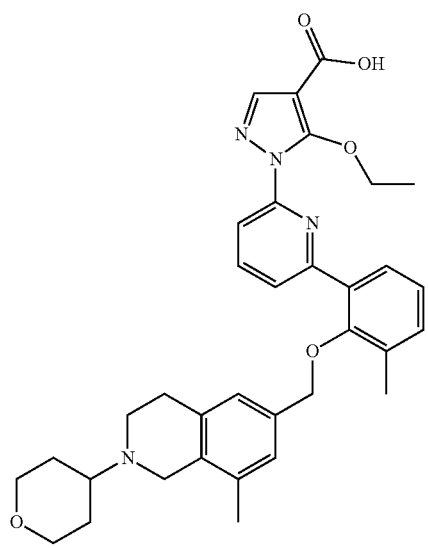 [SMILES: CCOc1c(C(=O)O)cnn1-c1cccc(-c2cccc(C)c2OCc2cc(C)c3c(c2)CCN(C2CCOCC2)C3)n1] |
| Cpd No. | Structure |
|---|---|
| 170 | 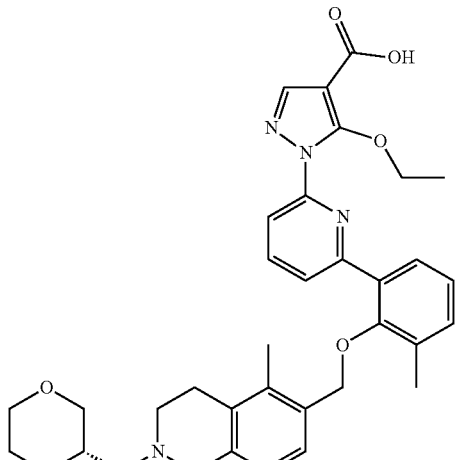 |
| 171 | 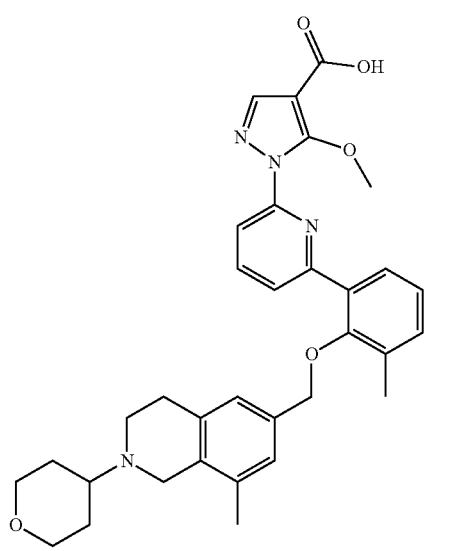 |
| 172 | 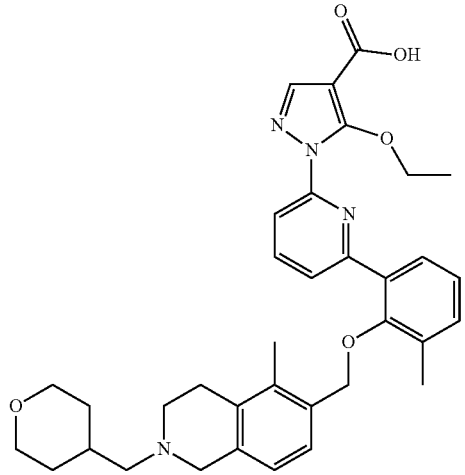 [SMILES: CCOc1c(C(=O)O)cnn1-c1cccc(-c2cccc(C)c2OCc2ccc3c(c2C)CCN(CC2CCOCC2)C3)n1] |

US 11,690,848 B2
-continued
| Cpd No. | Structure |
|---|---|
| 173 | 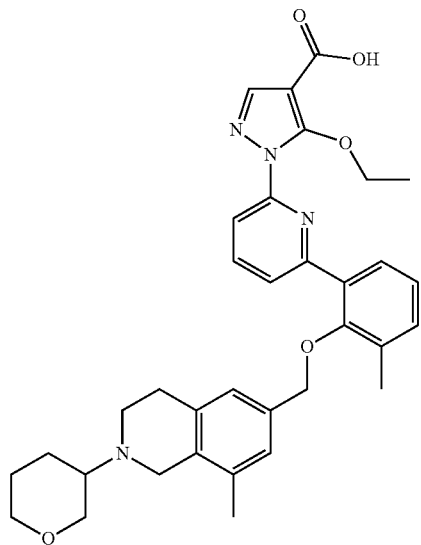 [SMILES: CCOc1c(C(=O)O)cnn1-c1cccc(-c2cccc(C)c2OCc2cc(C)c3c(c2)CCN(C2CCCOC2)C3)n1] |
| 174 | 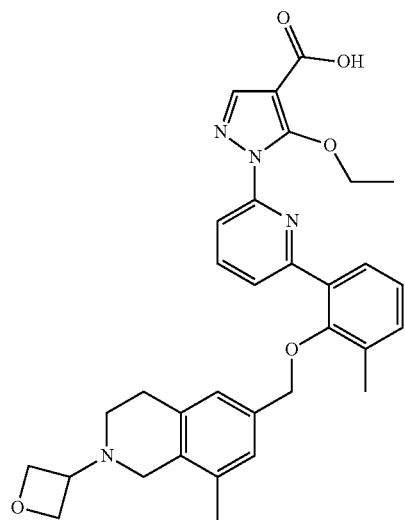 [SMILES: CCOc1c(C(=O)O)cnn1-c1cccc(-c2cccc(C)c2OCc2cc(C)c3c(c2)CCN(C2COC2)C3)n1] |
| 175 | 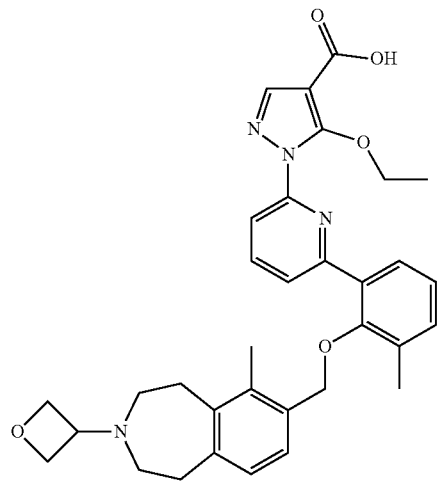 |
-continued
| Cpd No. | Structure |
|---|---|
| 176 | 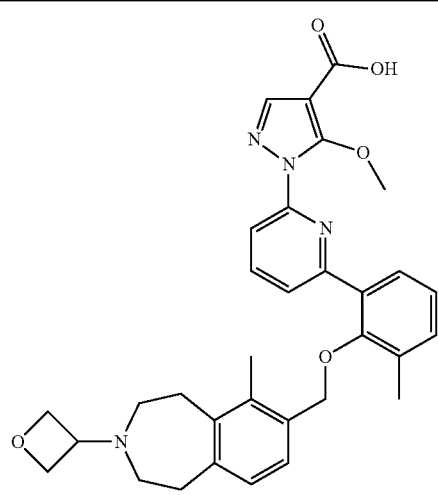 |
| 177 | 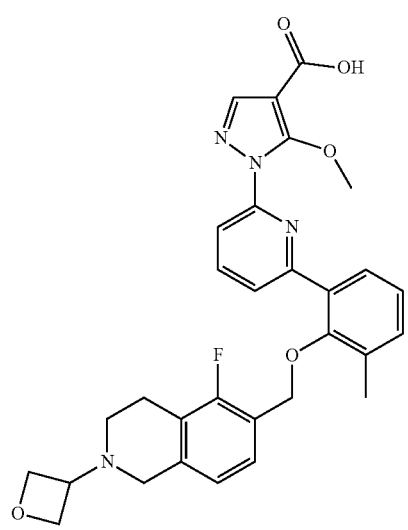 [SMILES: COc1c(C(=O)O)cnn1-c1cccc(-c2cccc(C)c2OCc2ccc3c(c2F)CCN(C2COC2)C3)n1] |
| 178 | 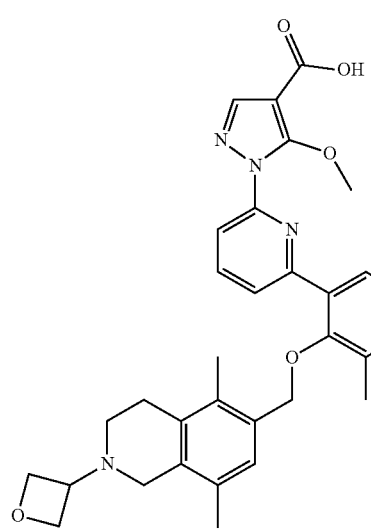 |

179
-continued
| Cpd No. | Structure |
|---|---|
| 179 | 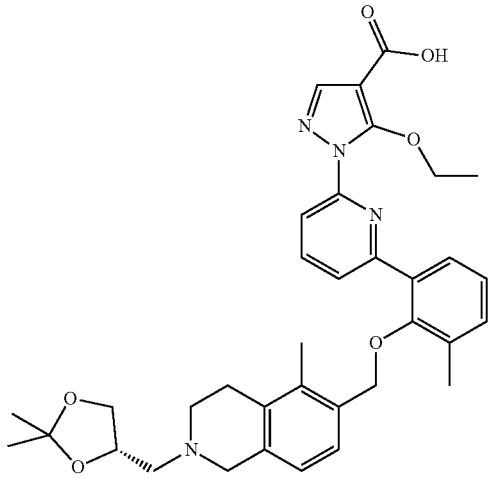 [SMILES: CCOc1c(C(=O)O)cnn1-c1cccc(-c2cccc(C)c2OCc2ccc3c(c2C)CCN(C[C@H]2COC(C)(C)O2)C3)n1] |
| 180 | 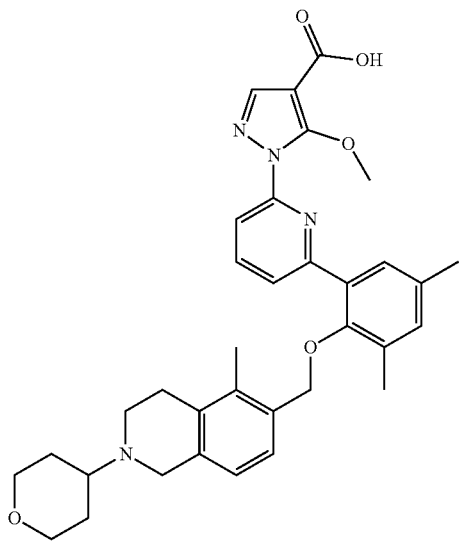 [SMILES: COc1c(C(=O)O)cnn1-c1cccc(-c2cc(C)cc(C)c2OCc2ccc3c(c2C)CCN(C2CCOCC2)C3)n1] |
| 181 | 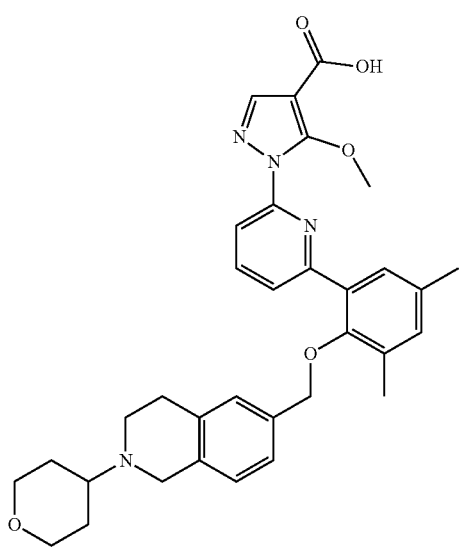 [SMILES: COc1c(C(=O)O)cnn1-c1cccc(-c2cc(C)cc(C)c2OCc2ccc3c(c2)CCN(C2CCOCC2)C3)n1] |
180
-continued
| Cpd No. | Structure |
|---|---|
| 182 | 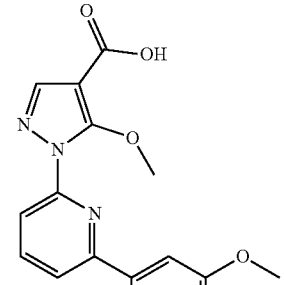 |
| 183 | 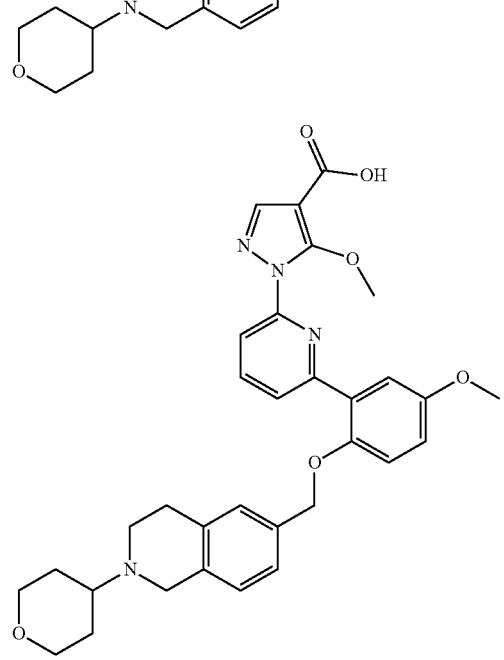 |
| 184 | 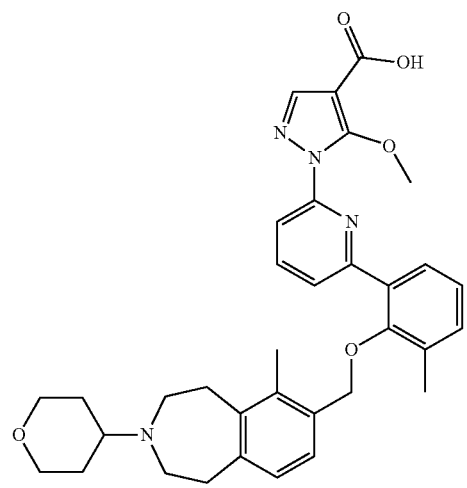 [SMILES: COc1c(C(=O)O)cnn1-c1cccc(-c2cccc(C)c2OCc2ccc3c(c2C)CCN(C2CCOCC2)CC3)n1] |

US 11,690,848 B2
181
-continued
| Cpd No. | Structure |
|---|---|
| 185 | 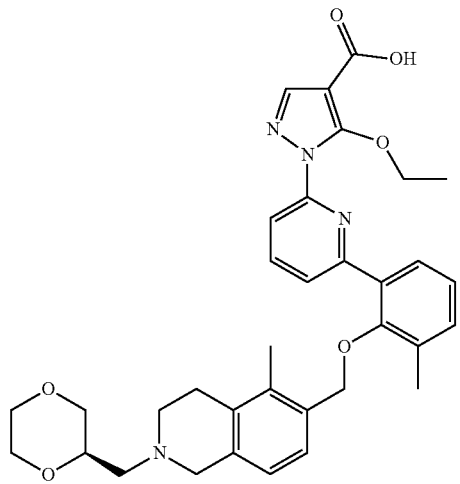 [SMILES: CCOc1c(C(=O)O)cnn1-c1cccc(-c2cccc(C)c2OCc2ccc3c(c2C)CCN(C[C@@H]2COCCO2)C3)n1] |
| 186 | 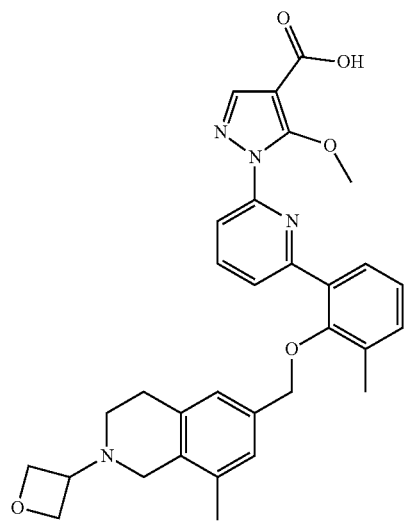 [SMILES: COc1c(C(=O)O)cnn1-c1cccc(-c2cccc(C)c2OCc2cc(C)c3c(c2)CCN(C2COC2)C3)n1] |
| 187 | 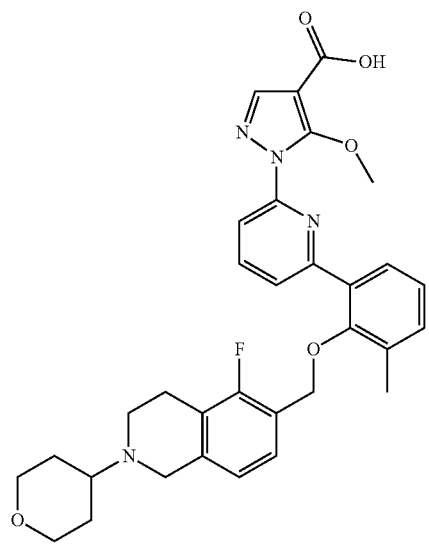 [SMILES: COc1c(C(=O)O)cnn1-c1cccc(-c2cccc(C)c2OCc2ccc3c(c2F)CCN(C2CCOCC2)C3)n1] |
182
-continued
| Cpd No. | Structure |
|---|---|
| 188 | 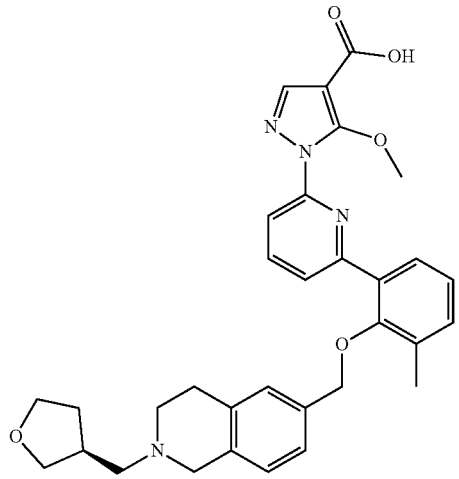 [SMILES: COc1c(C(=O)O)cnn1-c1cccc(-c2cccc(C)c2OCc2ccc3c(c2)CCN(C[C@@H]2CCOC2)C3)n1] |
| 189 | 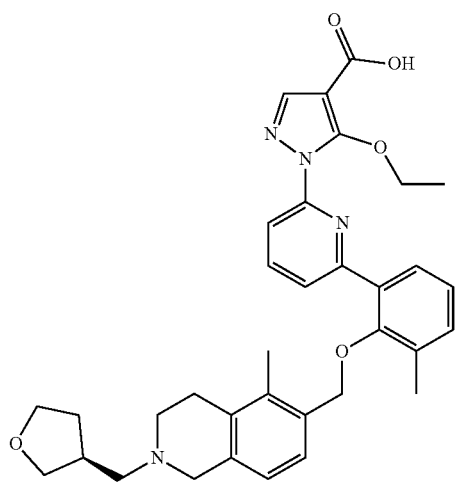 |
| 190 | 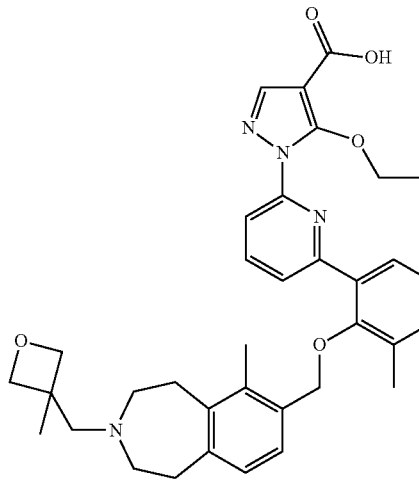 |

-continued

| Cpd No. | Structure |
|---|---|
| 191 | |
| 192 | |
| 193 | |

-continued

| Cpd No. | Structure |
|---|---|
| 194 | 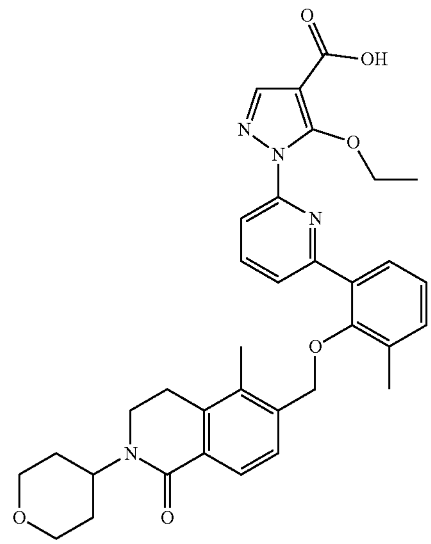 |
| 195 | 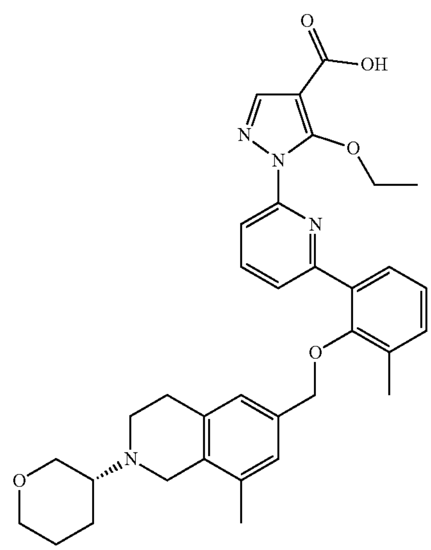 [SMILES: CCOc1c(C(=O)O)cnn1-c1cccc(-c2cccc(C)c2OCc2cc(C)c3c(c2)CCN([C@@H]2CCCOC2)C3)n1] |
| 196 | 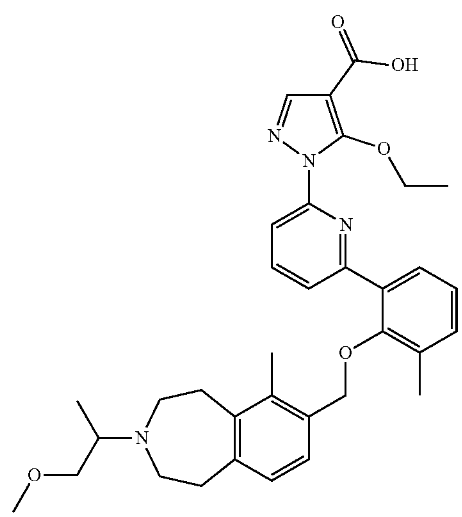 [SMILES: CCOc1c(C(=O)O)cnn1-c1cccc(-c2cccc(C)c2OCc2ccc3c(c2C)CCN(C(C)COC)CC3)n1] |

-continued
| Cpd No. | Structure |
|---|---|
| 197 | 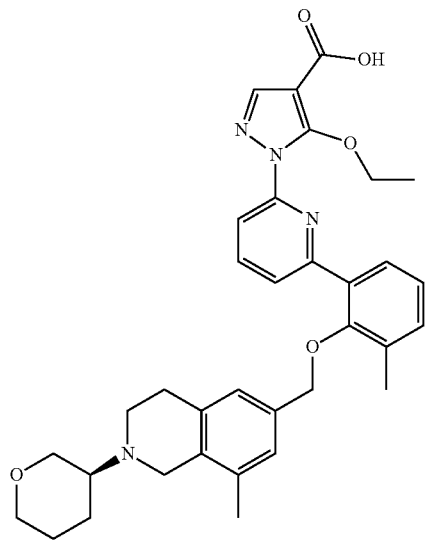 [SMILES: CCOc1c(C(=O)O)cnn1-c1cccc(-c2cccc(C)c2OCc2cc(C)c3c(c2)CCN([C@H]2CCCOC2)C3)n1] |
| 198 | 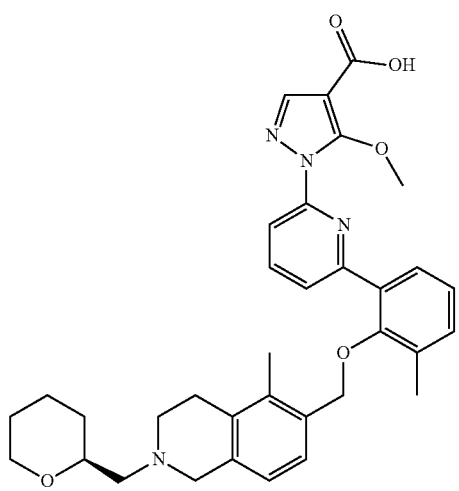 |
| 199 | 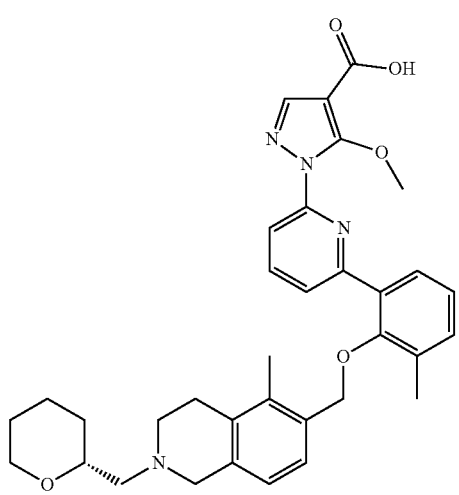 |
-continued
| Cpd No. | Structure |
|---|---|
| 200 | 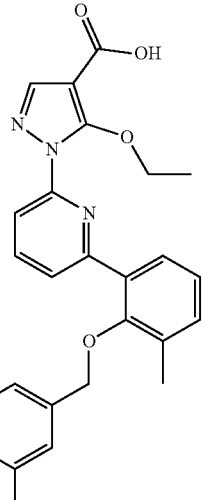 |
| 201 | 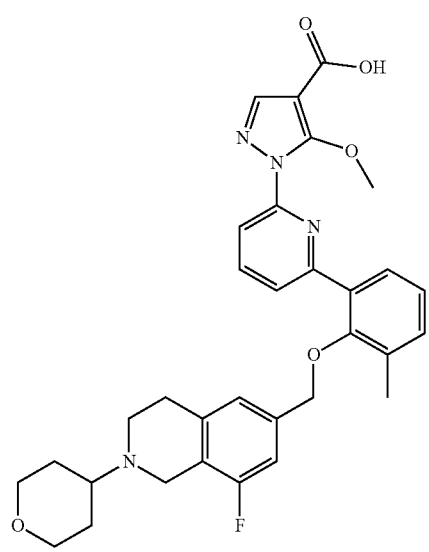 |
| 202 | 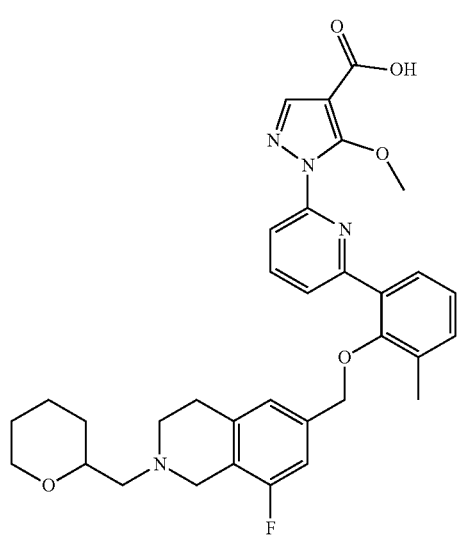 |

187
-continued
| Cpd No. | Structure |
|---|---|
| 203 | 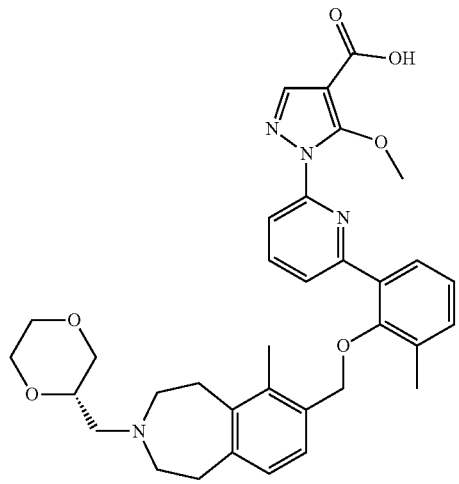 |
| 204 | 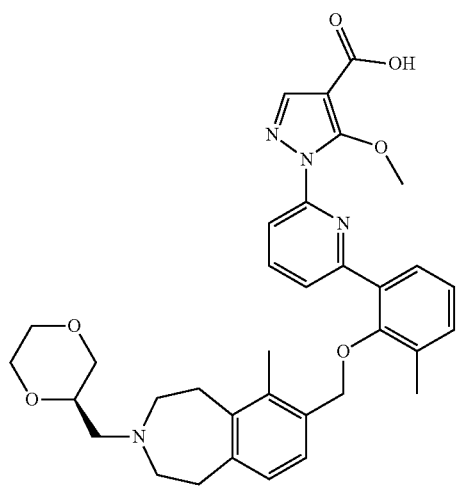 [SMILES: COc1c(C(=O)O)cnn1-c1cccc(-c2cccc(C)c2OCc2ccc3c(c2C)CCN(C[C@@H]2COCCO2)CC3)n1] |
| 205 | 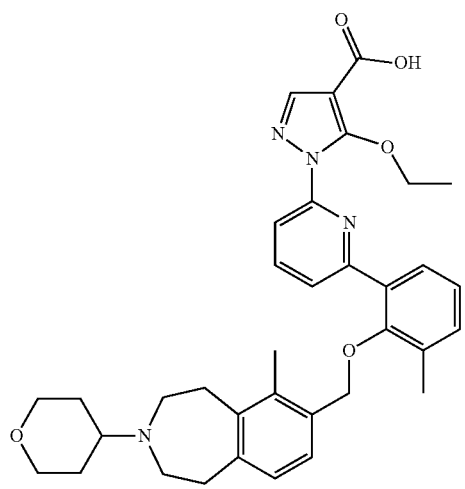 [SMILES: CCOc1c(C(=O)O)cnn1-c1cccc(-c2cccc(C)c2OCc2ccc3c(c2C)CCN(C2CCOCC2)CC3)n1] |
188
-continued
| Cpd No. | Structure |
|---|---|
| 206 | 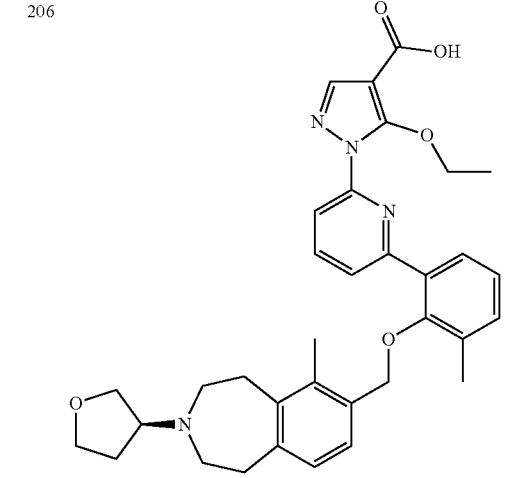 |
| 207 | 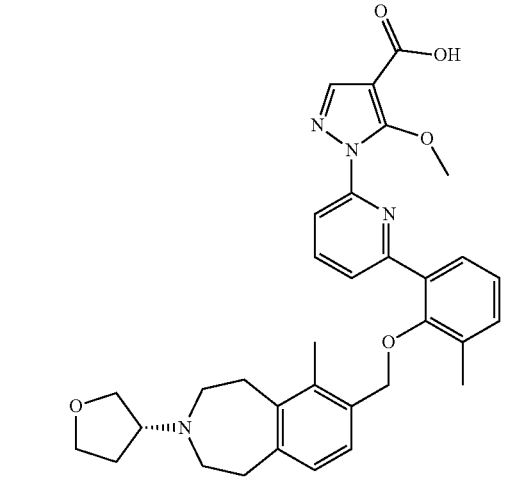 [SMILES: COc1c(C(=O)O)cnn1-c1cccc(-c2cccc(C)c2OCc2ccc3c(c2C)CCN([C@@H]2CCOC2)CC3)n1] |
| 208 | 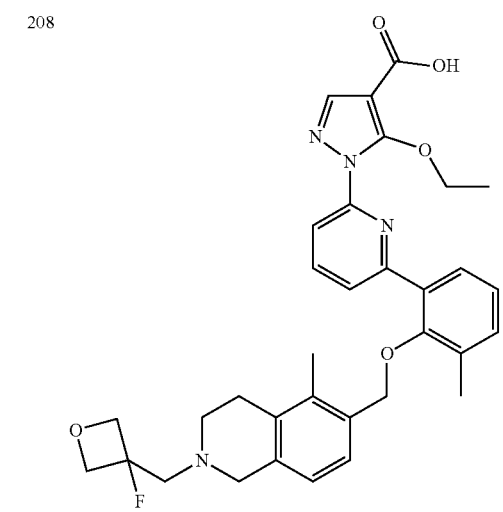 |

| Cpd No. | Structure |
|---|---|
| 209 | 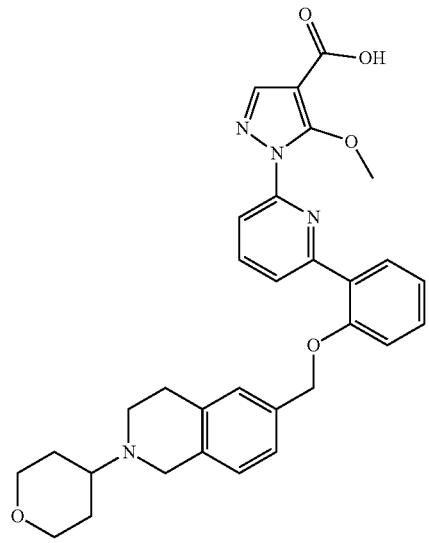 [SMILES: COc1c(C(=O)O)cnn1-c1cccc(-c2ccccc2OCc2ccc3c(c2)CCN(C2CCOCC2)C3)n1] |
| 210 | 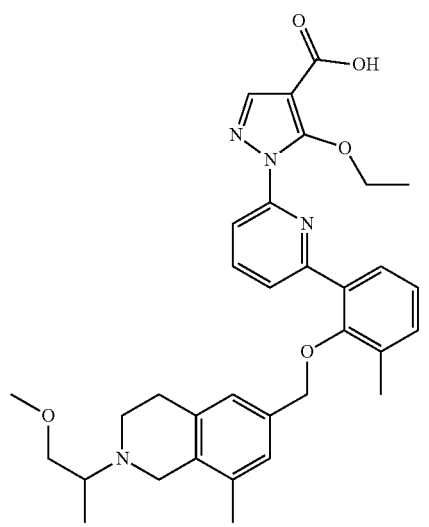 [SMILES: CCOc1c(C(=O)O)cnn1-c1cccc(-c2cccc(C)c2OCc2cc(C)c3c(c2)CCN(C(C)COC)C3)n1] |
| 211 | 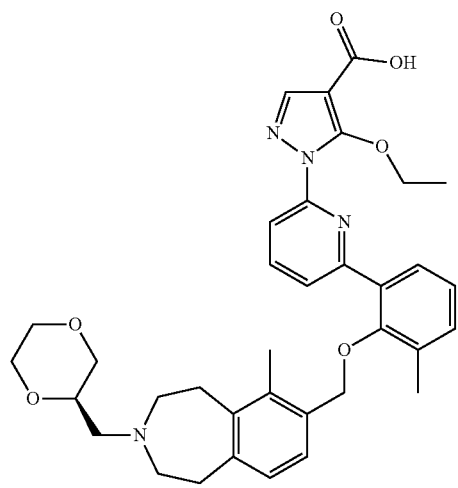 |
| Cpd No. | Structure |
|---|---|
| 212 | 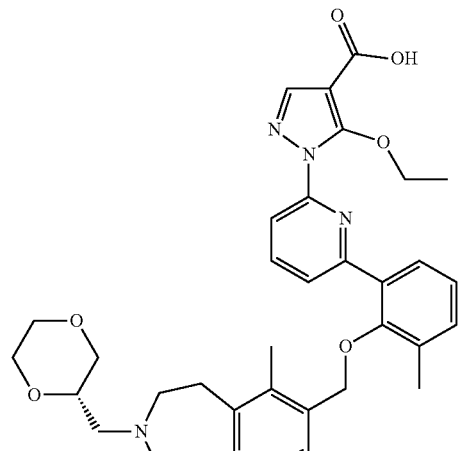 |
| 213 | 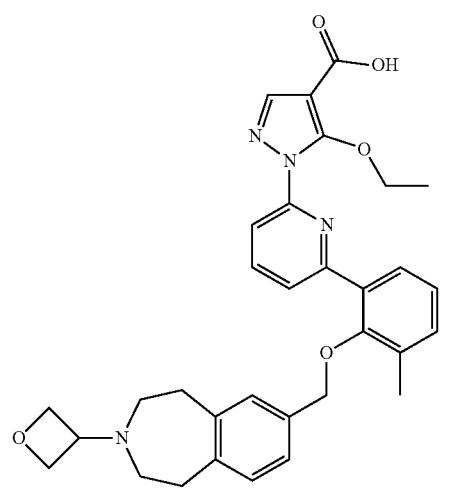 [SMILES: CCOc1c(C(=O)O)cnn1-c1cccc(-c2cccc(C)c2OCc2ccc3c(c2)CCN(C2COC2)CC3)n1] |
| 214 | 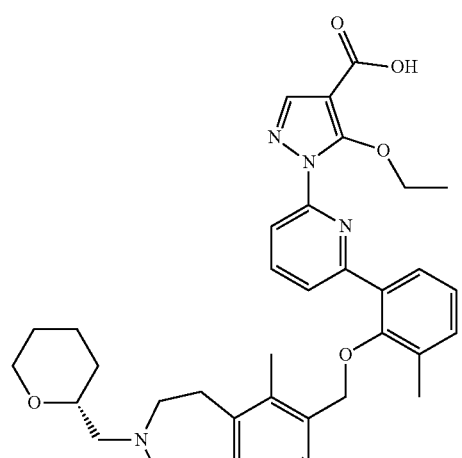 |

-continued
| Cpd No. | Structure |
|---|---|
| 215 | 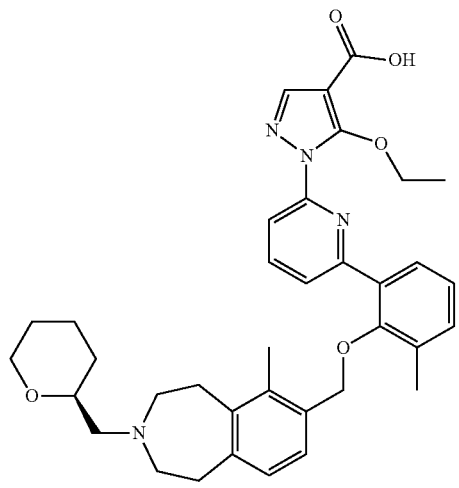 |
| 216 | 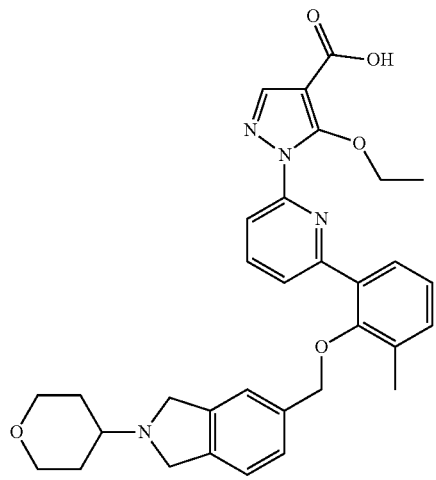 [SMILES: CCOc1c(C(=O)O)cnn1-c1cccc(-c2cccc(C)c2OCc2ccc3c(c2)CN(C2CCOCC2)C3)n1] |
| 217 | 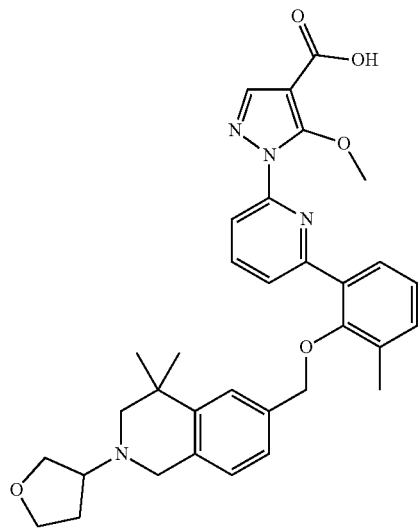 [SMILES: COc1c(C(=O)O)cnn1-c1cccc(-c2cccc(C)c2OCc2ccc3c(c2)C(C)(C)CN(C2CCOC2)C3)n1] |
-continued
| Cpd No. | Structure |
|---|---|
| 218 | 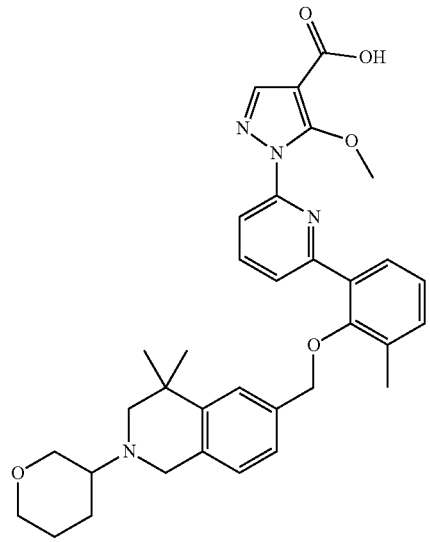 [SMILES: COc1c(C(=O)O)cnn1-c1cccc(-c2cccc(C)c2OCc2ccc3c(c2)C(C)(C)CN(C2CCCOC2)C3)n1] |
| 219 | 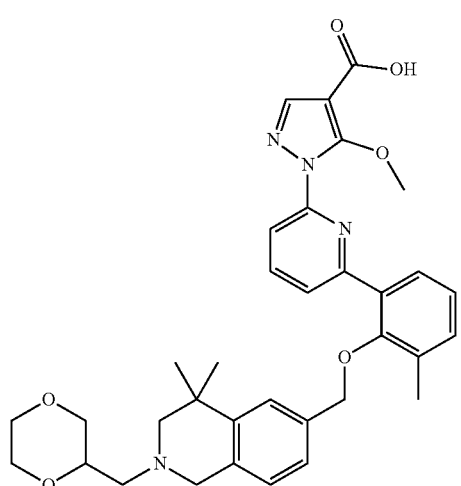 |
| 220 | 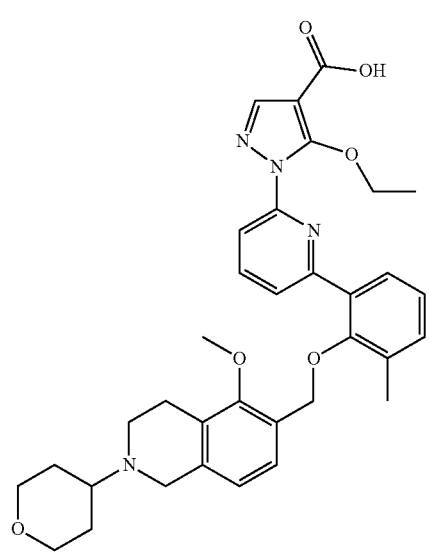 [SMILES: CCOc1c(C(=O)O)cnn1-c1cccc(-c2cccc(C)c2OCc2ccc3c(c2OC)CCN(C2CCOCC2)C3)n1] |

| Cpd No. | Structure |
|---|---|
| 221 | 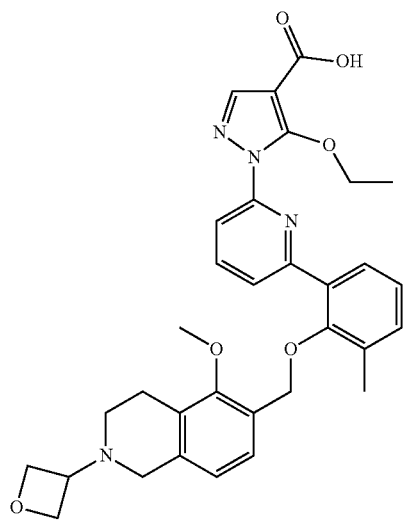 [SMILES: CCOc1c(C(=O)O)cnn1-c1cccc(-c2cccc(C)c2OCc2ccc3c(c2OC)CCN(C2COC2)C3)n1] |
| 222 | 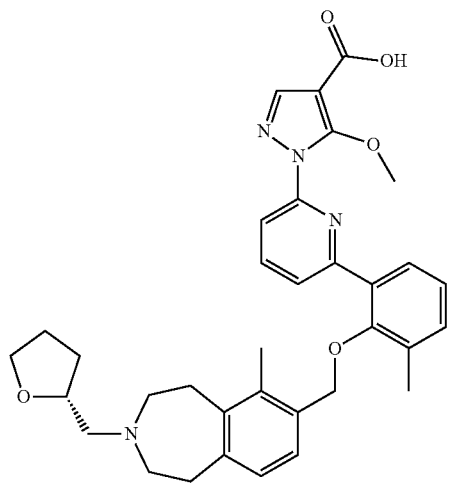 [SMILES: COc1c(C(=O)O)cnn1-c1cccc(-c2cccc(C)c2OCc2ccc3c(c2C)CCN(C[C@H]2CCCO2)CC3)n1] |
| 223 | 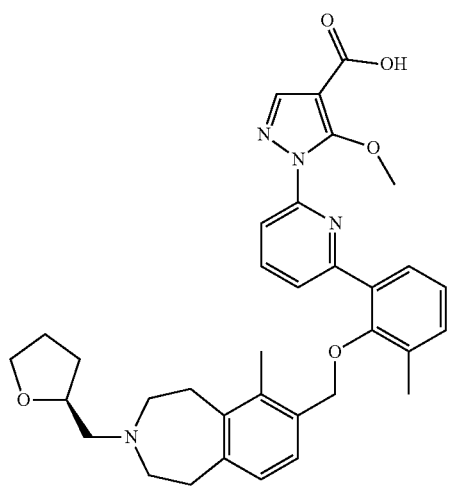 [SMILES: COc1c(C(=O)O)cnn1-c1cccc(-c2cccc(C)c2OCc2ccc3c(c2C)CCN(C[C@@H]2CCCO2)CC3)n1] |
| 224 | 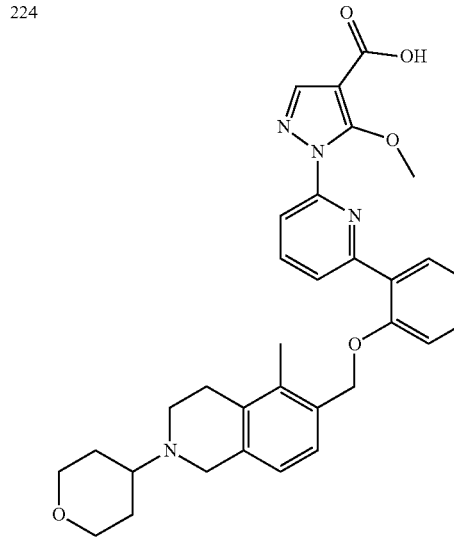 |
| 225 | 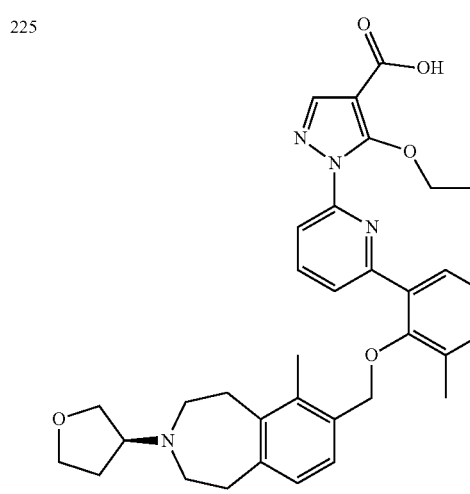 |
| 226 | 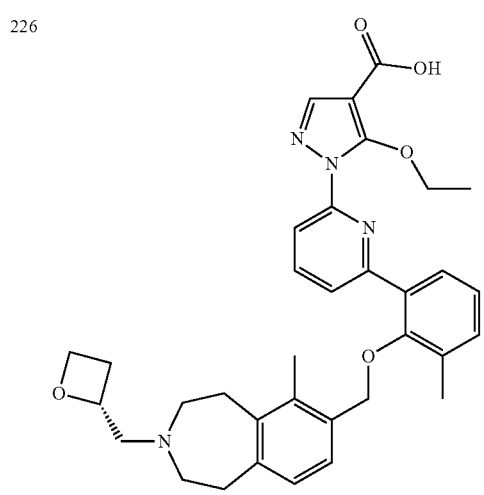 |

| Cpd No. | Structure |
|---|---|
| 227 | 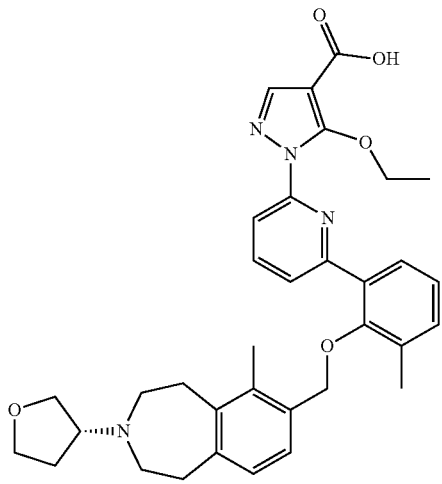 [SMILES: CCOc1c(C(=O)O)cnn1-c1cccc(-c2cccc(C)c2OCc2ccc3c(c2C)CCN([C@@H]2CCOC2)CC3)n1] |
| 228 | 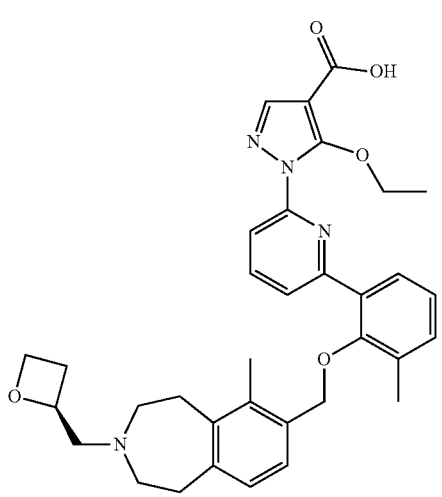 [SMILES: CCOc1c(C(=O)O)cnn1-c1cccc(-c2cccc(C)c2OCc2ccc3c(c2C)CCN(C[C@@H]2CCO2)CC3)n1] |
| 229 | 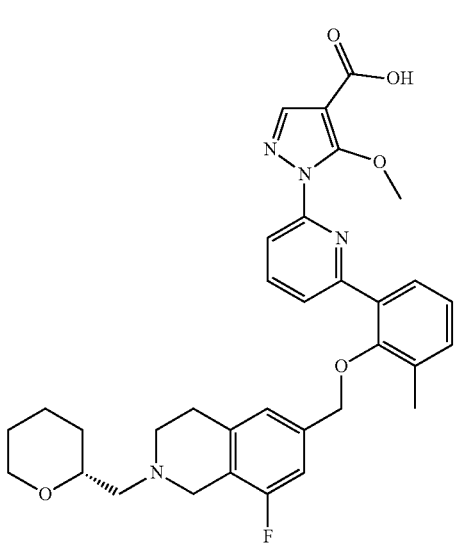 |
| 230 | 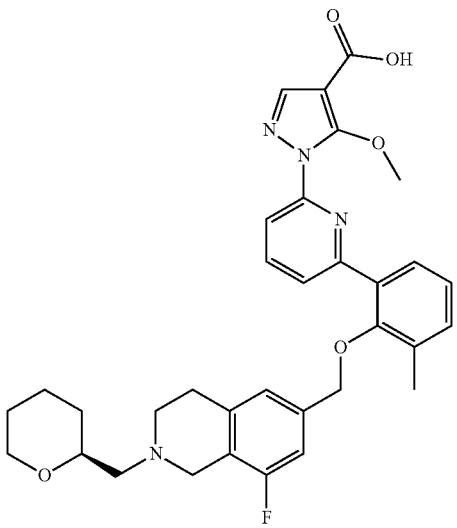 |
| 231 | 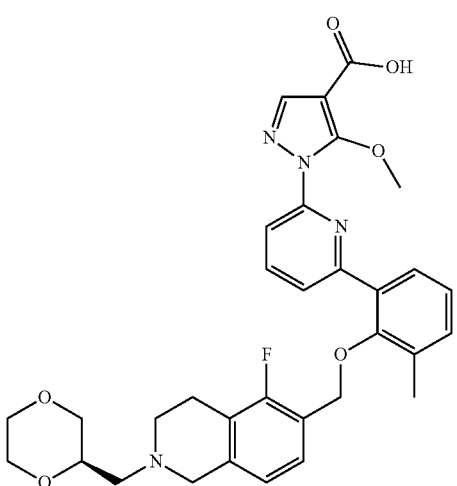 |
| 232 | 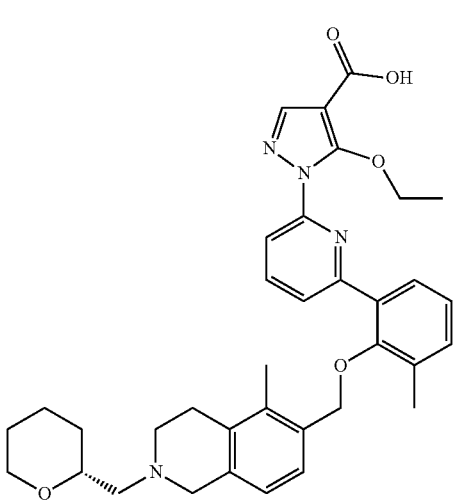 |

-continued
| Cpd No. | Structure |
|---|---|
| 233 | 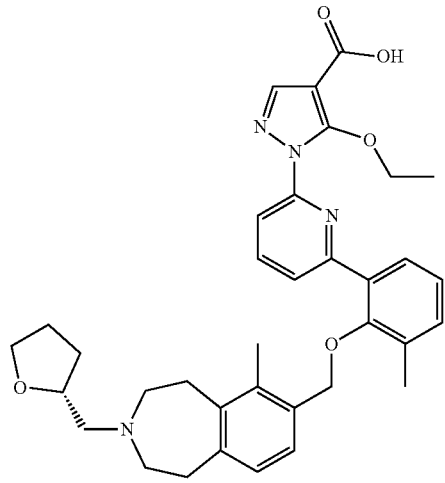 [SMILES: CCOc1c(C(=O)O)cnn1-c1cccc(-c2cccc(C)c2OCc2ccc3c(c2C)CCN(C[C@H]2CCCO2)CC3)n1] |
| 234 | 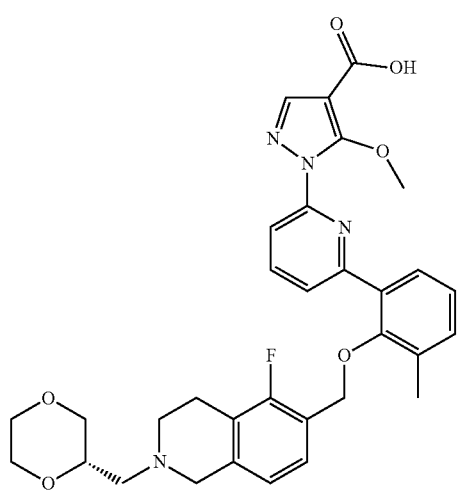 [SMILES: COc1c(C(=O)O)cnn1-c1cccc(-c2cccc(C)c2OCc2ccc3c(c2F)CCN(C[C@H]2COCCO2)C3)n1] |
| 235 | 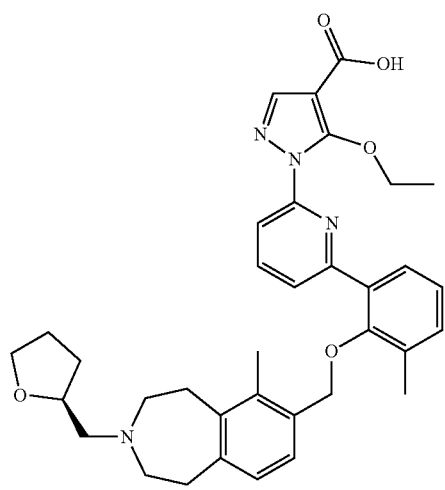 [SMILES: CCOc1c(C(=O)O)cnn1-c1cccc(-c2cccc(C)c2OCc2ccc3c(c2C)CCN(C[C@@H]2CCCO2)CC3)n1] |
-continued
| Cpd No. | Structure |
|---|---|
| 236 | 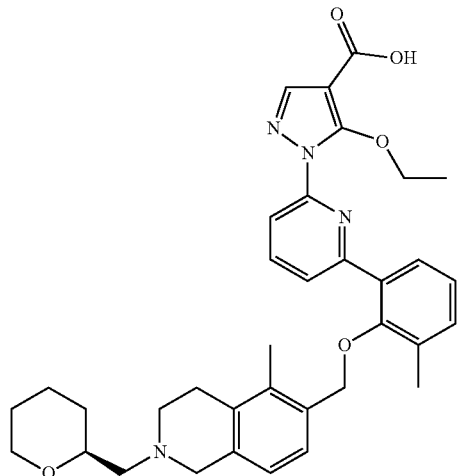 |
| 237 | 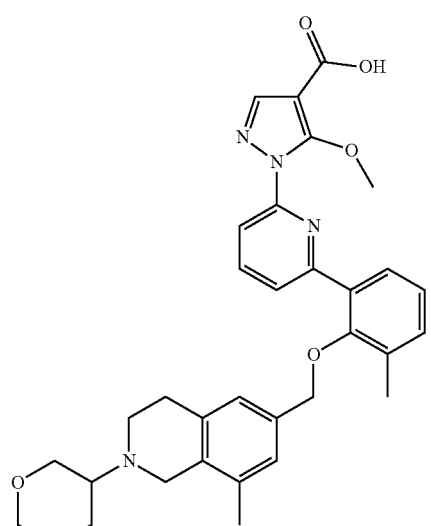 |
| 238 | 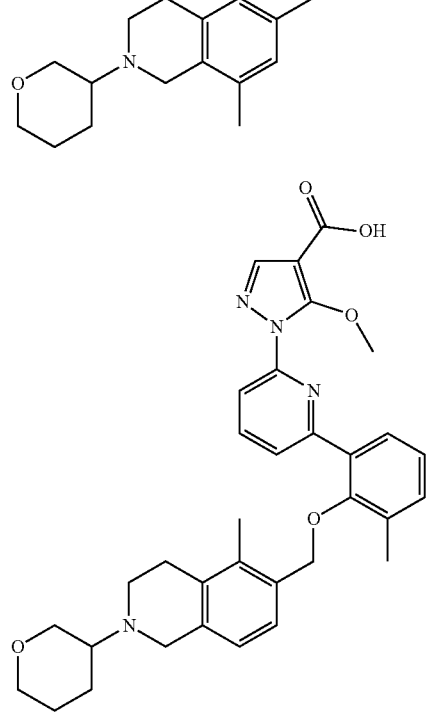 |

| Cpd No. | Structure |
|---|---|
| 239 | 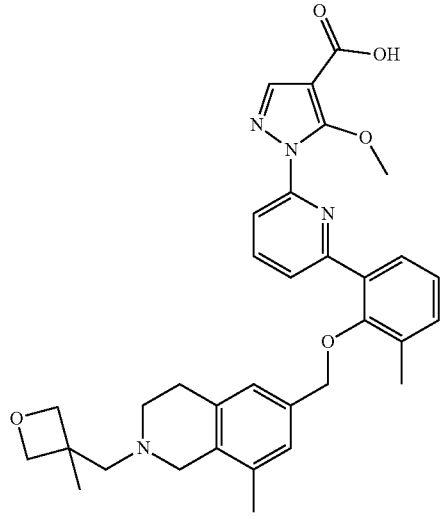 [SMILES: COc1c(C(=O)O)cnn1-c1cccc(-c2cccc(C)c2OCc2cc(C)c3c(c2)CCN(CC2(C)COC2)C3)n1] |
| 240 | 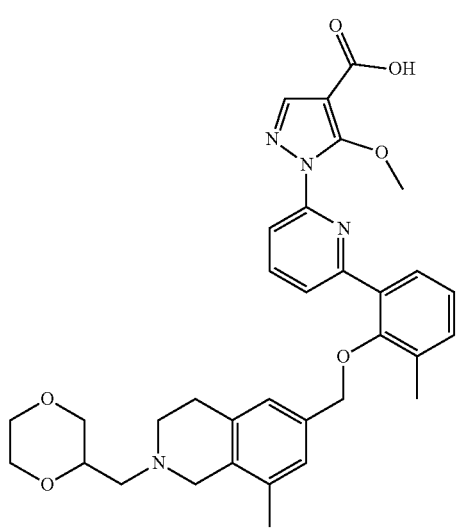 [SMILES: COc1c(C(=O)O)cnn1-c1cccc(-c2cccc(C)c2OCc2cc(C)c3c(c2)CCN(CC2COCCO2)C3)n1] |
| 241 | 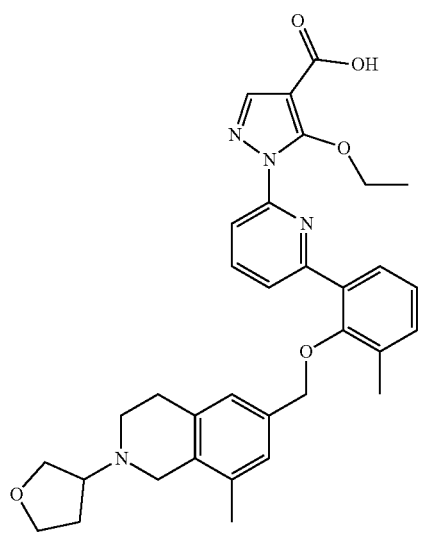 [SMILES: CCOc1c(C(=O)O)cnn1-c1cccc(-c2cccc(C)c2OCc2cc(C)c3c(c2)CCN(C2CCOC2)C3)n1] |
| 242 | 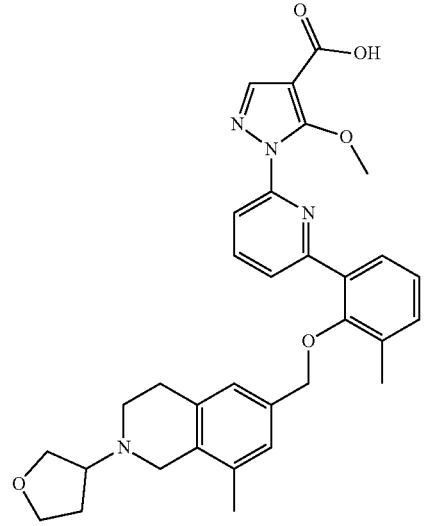 |
| 243 | 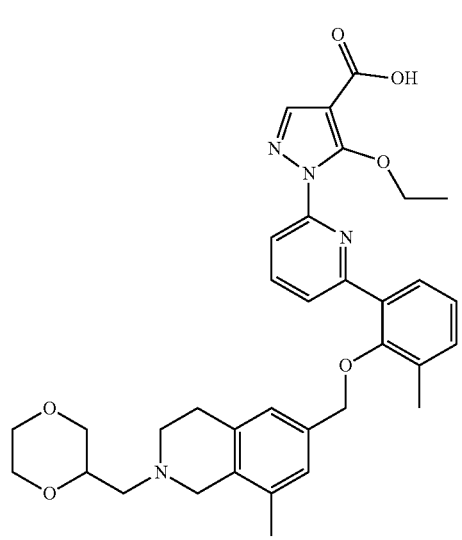 |
| 244 | 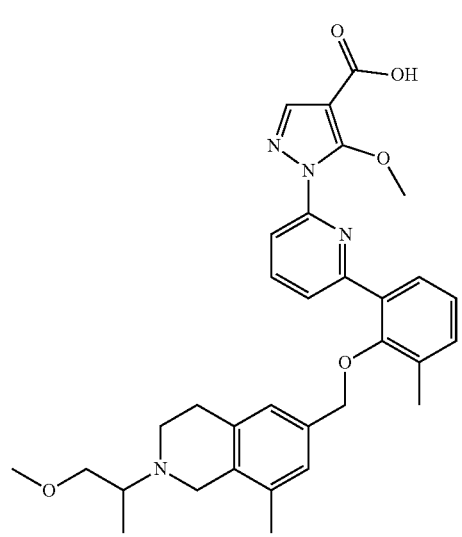 [SMILES: COCC(C)N1CCc2cc(COc3c(C)cccc3-c3cccc(-n4ncc(C(=O)O)c4OC)n3)cc(C)c2C1] |

201
-continued
| Cpd No. | Structure |
|---|---|
| 245 | 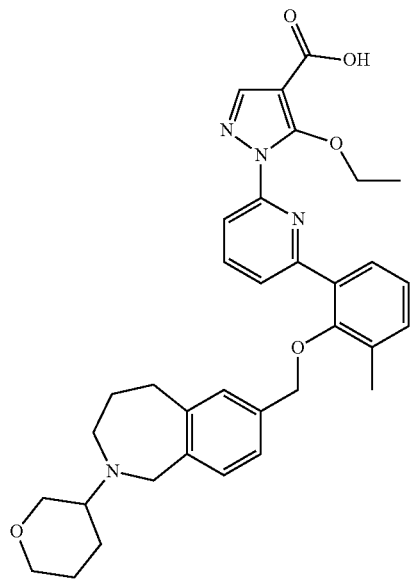 [SMILES: CCOc1c(C(=O)O)cnn1-c1cccc(-c2cccc(C)c2OCc2ccc3c(c2)CCCN(C2CCCOC2)C3)n1] |
| 246 | 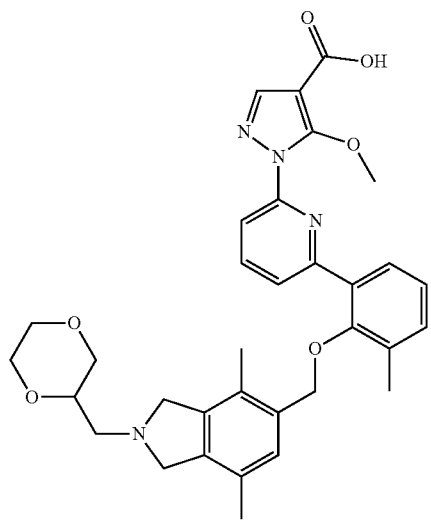 [SMILES: COc1c(C(=O)O)cnn1-c1cccc(-c2cccc(C)c2OCc2cc(C)c3c(c2C)CN(CC2COCCO2)C3)n1] |
| 247 | 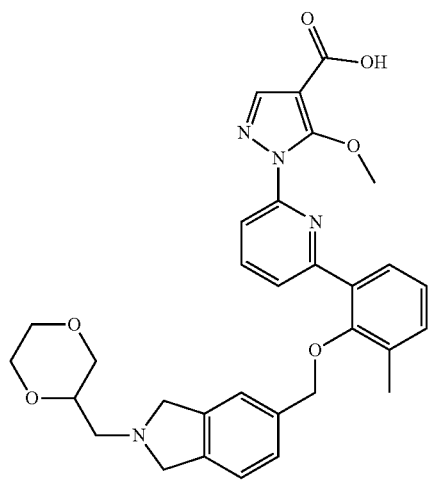 [SMILES: COc1c(C(=O)O)cnn1-c1cccc(-c2cccc(C)c2OCc2ccc3c(c2)CN(CC2COCCO2)C3)n1] |
202
-continued
| Cpd No. | Structure |
|---|---|
| 248 | 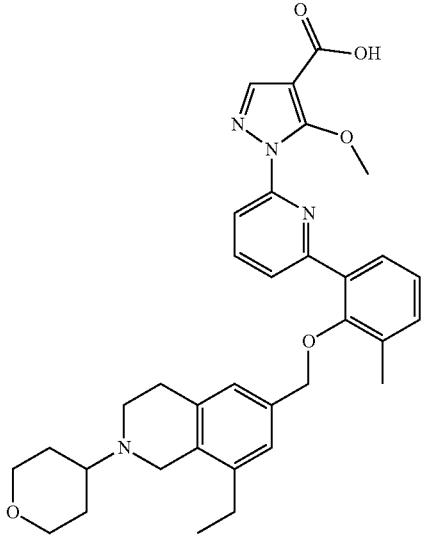 [SMILES: CCc1cc(COc2c(C)cccc2-c2cccc(-n3ncc(C(=O)O)c3OC)n2)cc2c1CN(C1CCOCC1)CC2] |
| 249 | 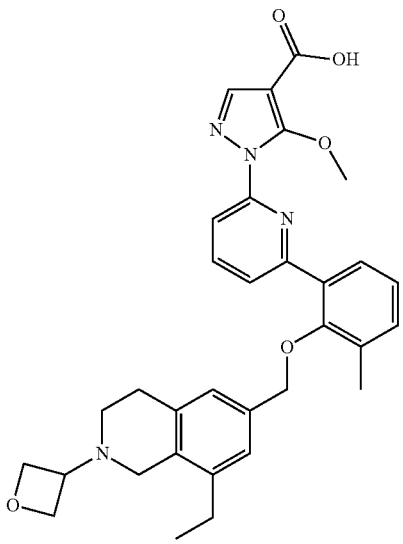 [SMILES: CCc1cc(COc2c(C)cccc2-c2cccc(-n3ncc(C(=O)O)c3OC)n2)cc2c1CN(C1COC1)CC2] |

| Cpd No. | Structure |
|---|---|
| 250 | 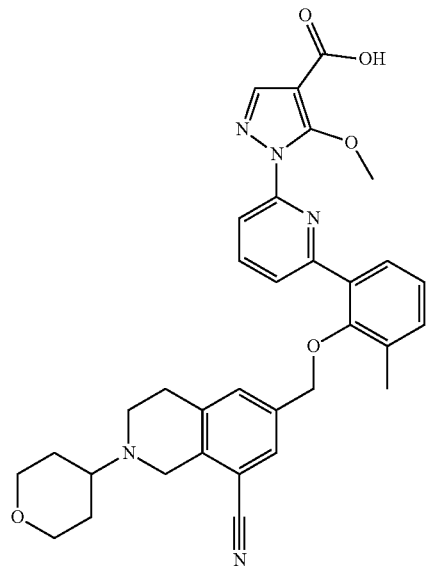 [SMILES: COc1c(C(=O)O)cnn1-c1cccc(-c2cccc(C)c2OCc2cc(C#N)c3c(c2)CCN(C2CCOCC2)C3)n1] |
| 251 | 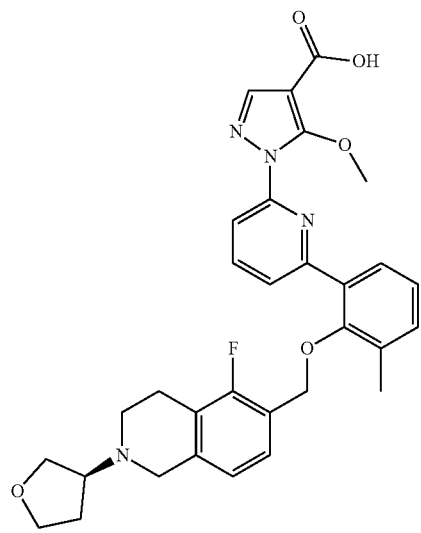 [SMILES: COc1c(C(=O)O)cnn1-c1cccc(-c2cccc(C)c2OCc2ccc3c(c2F)CCN([C@H]2CCOC2)C3)n1] |
| Cpd No. | Structure |
|---|---|
| 252 | 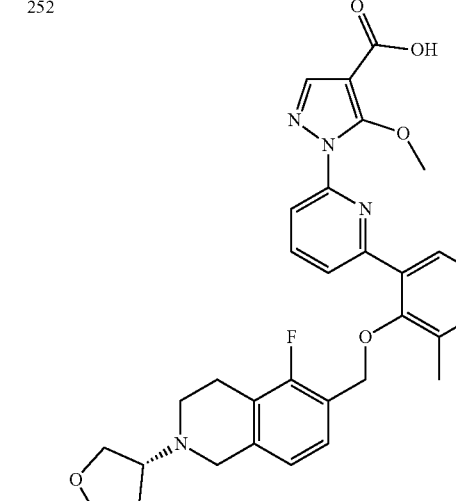 |
| 253 | |
| 254 | |
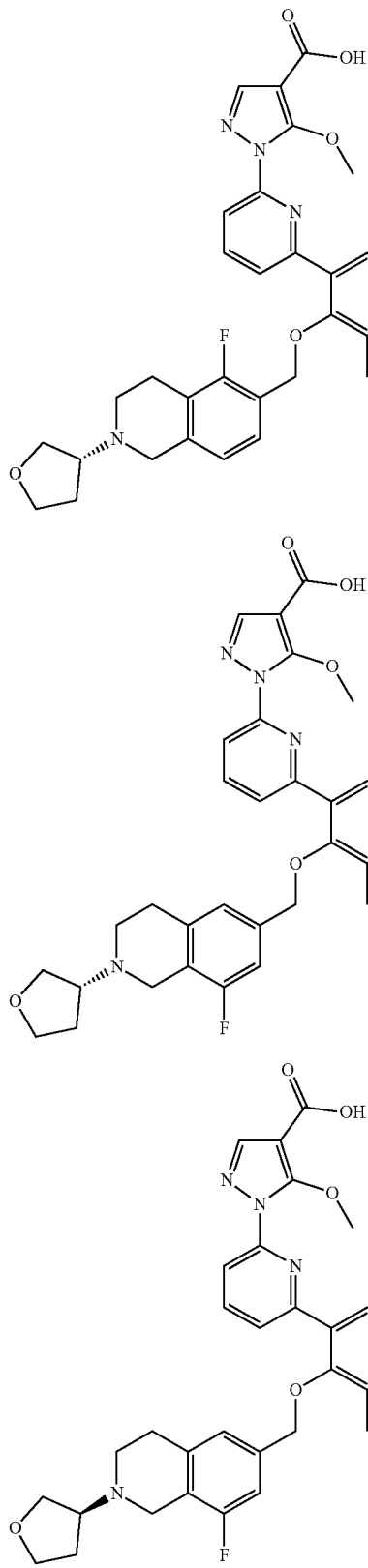

| Cpd No. | Structure |
|---|---|
| 255 | 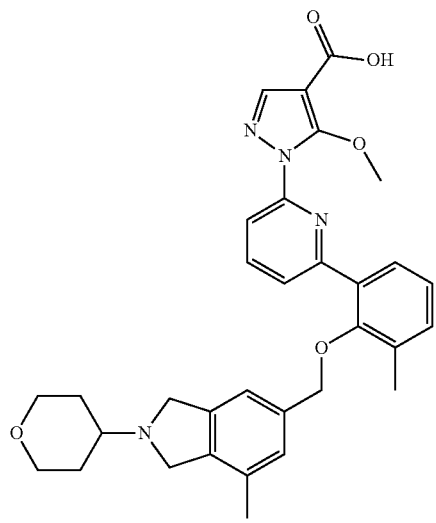 [SMILES: COc1c(C(=O)O)cnn1-c1cccc(-c2cccc(C)c2OCc2cc(C)c3c(c2)CN(C2CCOCC2)C3)n1] |
| 256 | 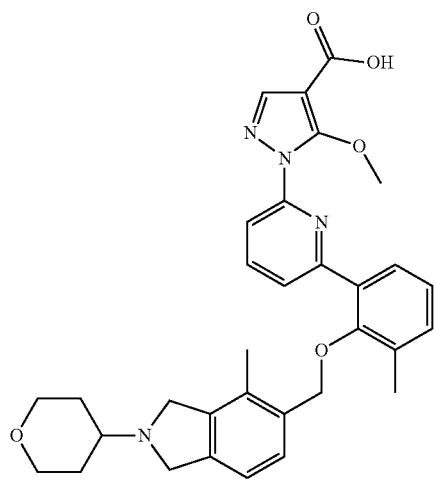 [SMILES: COc1c(C(=O)O)cnn1-c1cccc(-c2cccc(C)c2OCc2ccc3c(c2C)CN(C2CCOCC2)C3)n1] |
| 257 | 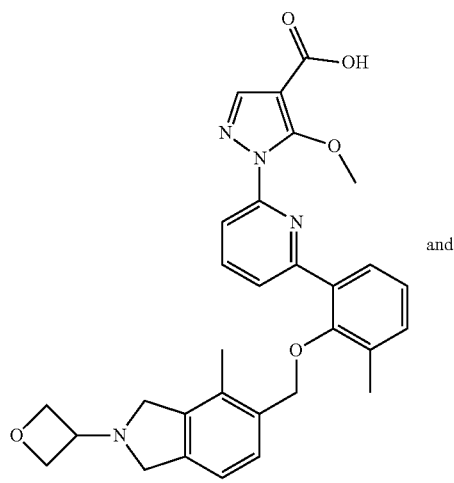 [SMILES: COc1c(C(=O)O)cnn1-c1cccc(-c2cccc(C)c2OCc2ccc3c(c2C)CN(C2COC2)C3)n1] |
| Cpd No. | Structure |
|---|---|
| 258 | 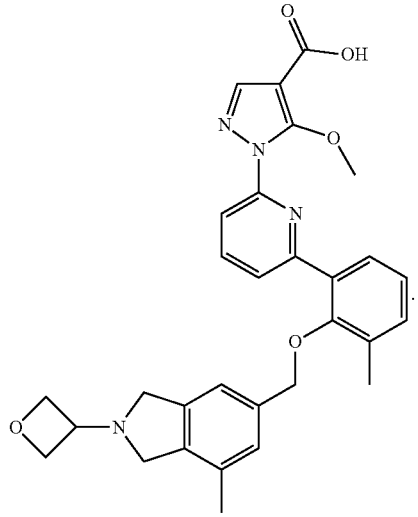 [SMILES: COc1c(C(=O)O)cnn1-c1cccc(-c2cccc(C)c2OCc2cc(C)c3c(c2)CN(C2COC2)C3)n1] |
11. The method of claim 10, wherein the compound is selected from the group consisting of:
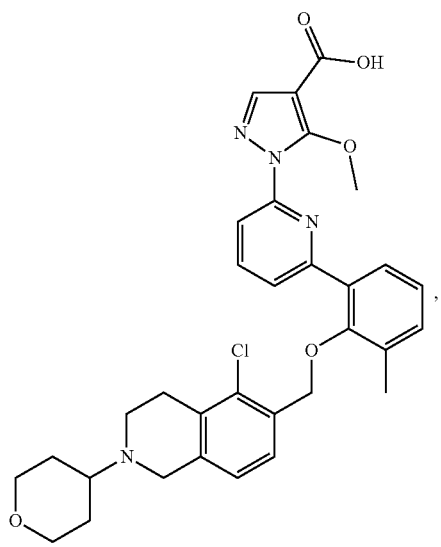

207
-continued
27
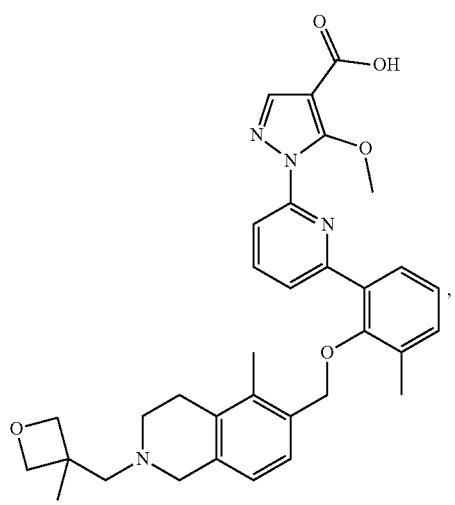
84
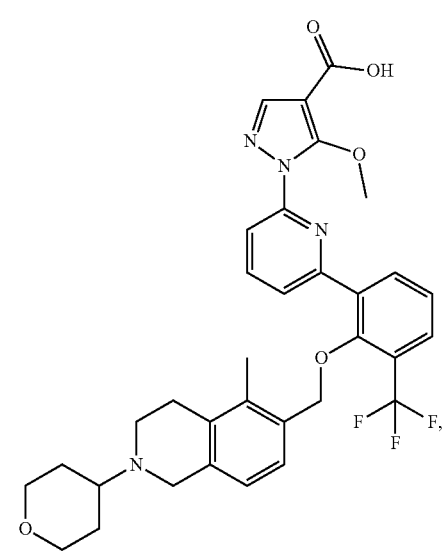
114
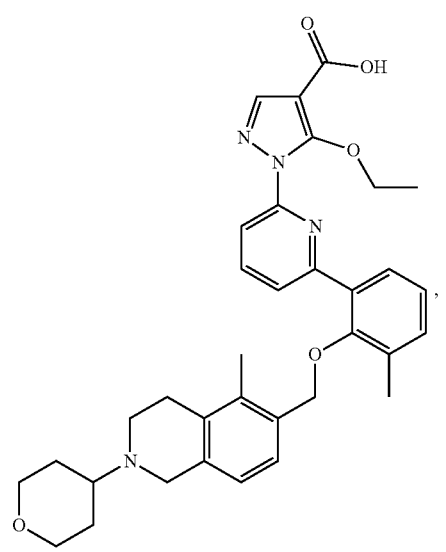
208
-continued
133
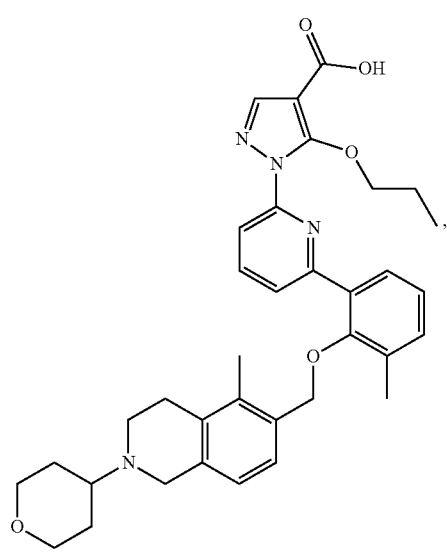
134
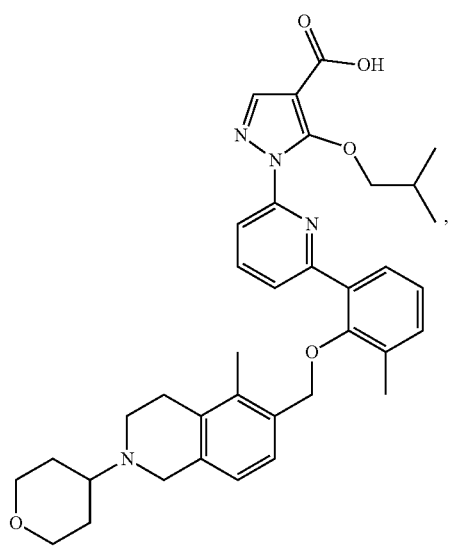
136
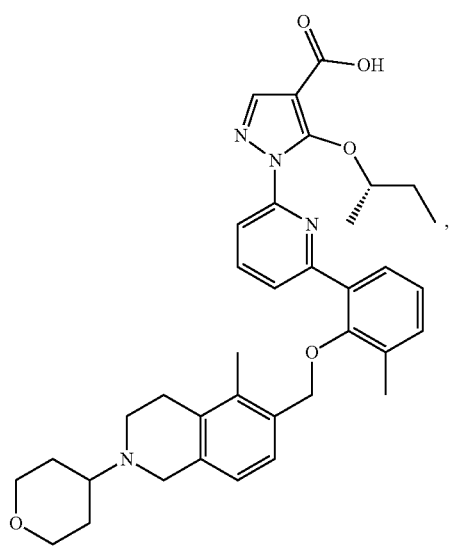

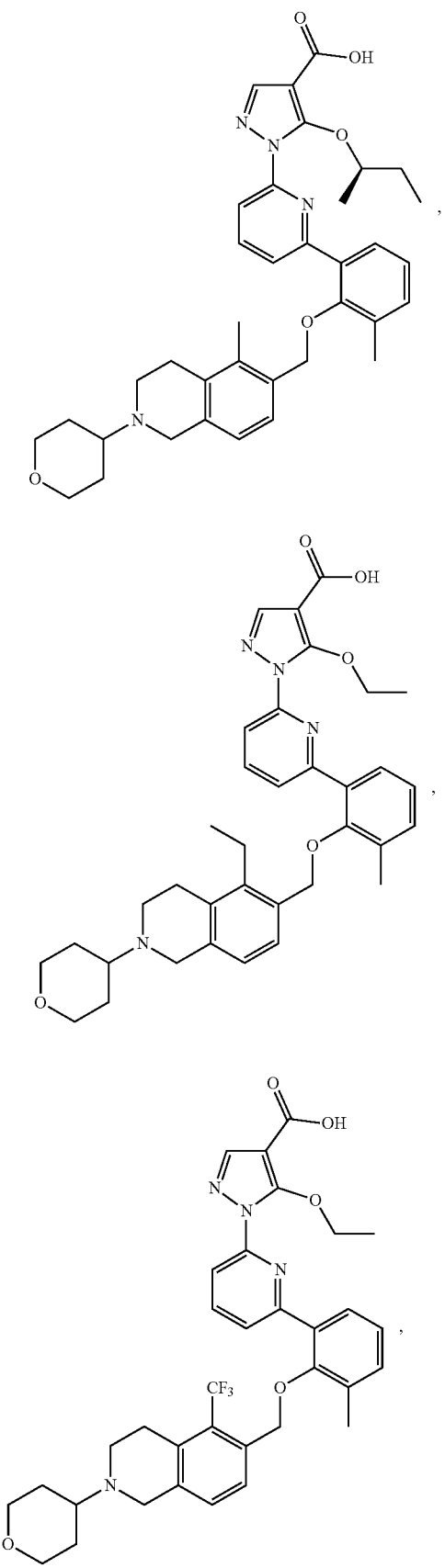
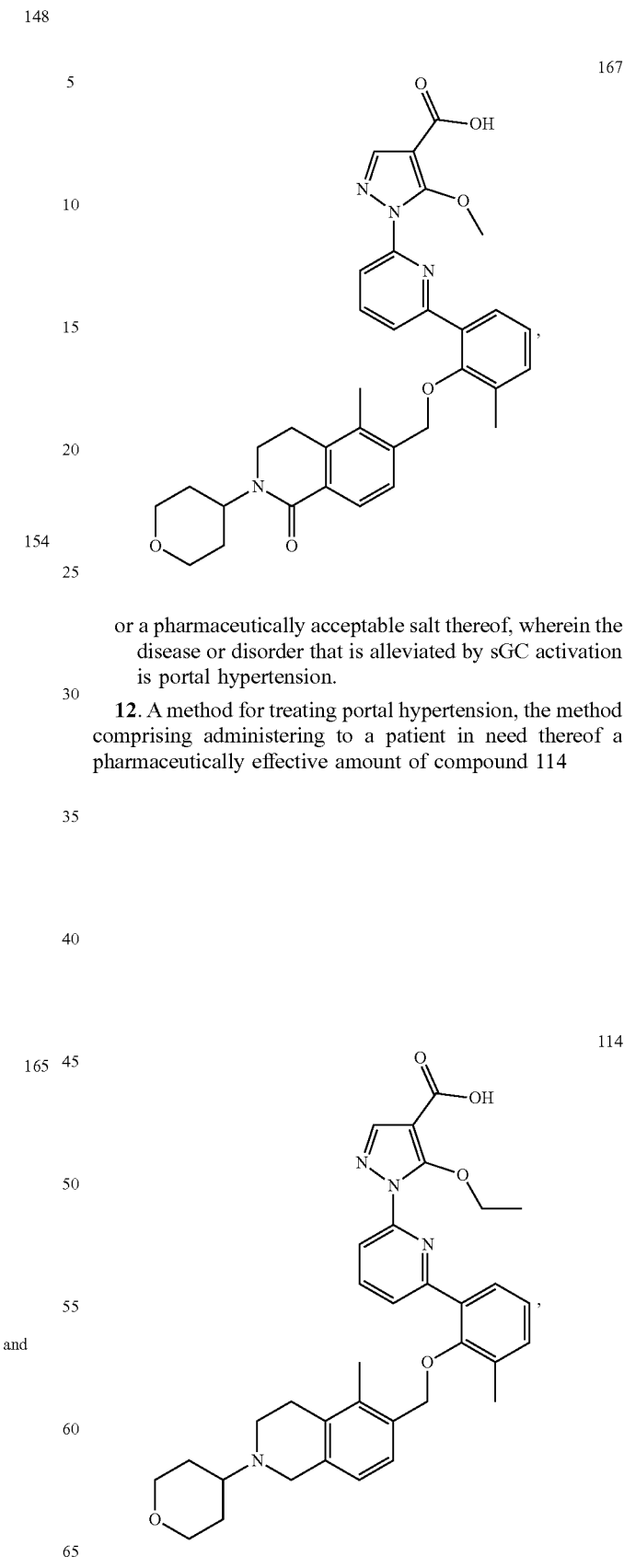
or a pharmaceutically acceptable salt thereof, wherein the disease or disorder that is alleviated by sGC activation is portal hypertension.
12. A method for treating portal hypertension, the method comprising administering to a patient in need thereof a pharmaceutically effective amount of compound 114
or a pharmaceutically acceptable salt thereof.

13. A method for treating portal hypertension, the method comprising administering to a patient in need thereof a pharmaceutically effective amount of compound 114
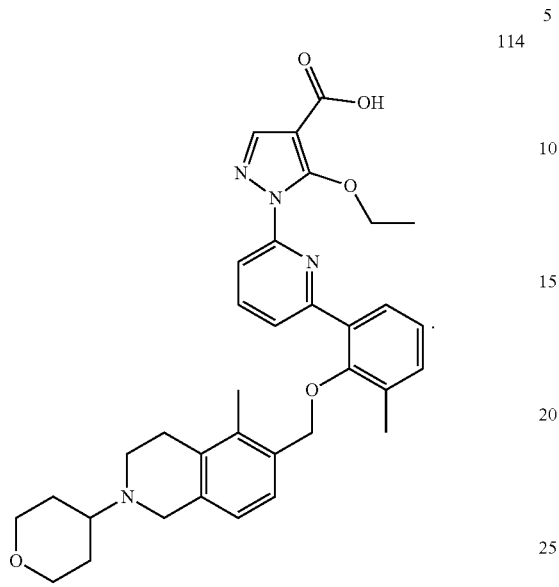
* * * * *